United States Patent [19]
Chang et al.

[11] Patent Number: 5,656,634
[45] Date of Patent: Aug. 12, 1997

[54] N-ARYL AND N-HETEROARYLAMIDE AND UREA DERIVATIVES AS INHIBITORS OF ACYL COENZYME A: CHOLESTEROL ACYL TRANSFERASE (ACAT)

[75] Inventors: George Chang, Ivoryton; Ernest S. Hamanaka, Gales Ferry; Peter A. McCarthy, Pawcatuck; Thien V. Truong, Old Saybrook; Frederick J. Walker, Preston, all of Conn.

[73] Assignee: Pfizer Inc., New York, N.Y.

[21] Appl. No.: 251,075

[22] Filed: May 31, 1994

Related U.S. Application Data

[60] Division of Ser. No. 916,651, Jul. 20, 1992, Pat. No. 5,362,878, which is a continuation-in-part of Ser. No. 648,677, Mar. 21, 1991, abandoned.

[51] Int. Cl.⁶ .......... A61K 31/44; C07D 213/38; C07D 239/42
[52] U.S. Cl. .......... 514/255; 514/352; 546/309; 544/332; 544/329; 544/322
[58] Field of Search .......... 546/309; 544/332, 544/329, 322; 514/255, 352

[56] References Cited

U.S. PATENT DOCUMENTS

| | | | |
|---|---|---|---|
| 3,969,362 | 7/1976 | Takahashi | 424/263 |
| 4,743,605 | 5/1988 | Hoefle | 514/269 |
| 5,142,094 | 8/1992 | O'Brien | 544/319 |

Primary Examiner—Alan L. Rotman
Assistant Examiner—D. Margaret M. Mach
Attorney, Agent, or Firm—Peter C. Richardson; Paul H. Ginsburg; Seymour G. Bekelnitzky

[57] ABSTRACT

Compounds of the formula

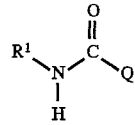

the pharmaceutically acceptable salts thereof, wherein Q and $R^1$ are as defined below, and novel carboxylic acid and acid halide intermediates used in the synthesis of such compounds. The compounds of formula I are inhibitors of acyl coenzyme A: cholesterol acyltransferase (ACAT) and are useful as hypolipidemic and antiatherosclerosis agents.

7 Claims, No Drawings

N-ARYL AND N-HETEROARYLAMIDE AND UREA DERIVATIVES AS INHIBITORS OF ACYL COENZYME A: CHOLESTEROL ACYL TRANSFERASE (ACAT)

This is a division of application Ser. No. 07/916,651, filed on Jul. 20, 1992 now U.S. Pat. No. 5,362,878, which is a continuation-in-part of application Ser. No. 07/648,677 filed Mar. 21, 1991 abandoned which is a continuation-in-part of PCT patent application PCT/US Ser. No. 89/04033, filed Sep. 15, 1989.

BACKGROUND OF THE INVENTION

The present invention relates to new N-aryl and N-heteroarylamide and urea derivatives, pharmaceutical compositions comprising such compounds, novel carboxylic acid and acid halide intermediates used in the synthesis of such compounds and the use of such compounds to inhibit intestinal absorption of cholesterol, lower serum cholesterol and reverse the development of atherosclerosis. The compounds are inhibitors of acyl coenzyme A: cholesterol acyltransferase (ACAT).

Cholesterol that is consumed in the diet (dietary cholesterol) is absorbed as free cholesterol by the mucosal cells of the small intestine. It is then esterified by the enzyme ACAT, packaged into particles known as chylomicrons, and released into the bloodstream. Chylomicrons are particles into which dietary cholesterol is packaged and transported in the bloodstream. By inhibiting the action of ACAT, the compounds of this invention prevent intestinal absorption of dietary cholesterol and thus lower serum cholesterol levels. They are therefore useful in preventing atherosclerosis, heart attacks and strokes.

By inhibiting the action of ACAT, the compounds of the present invention also enable cholesterol to be removed from the walls of blood vessels. This activity renders such compounds useful in slowing or reversing the development of atherosclerosis as well as in preventing heart attacks and strokes.

Other inhibitors of ACAT are referred to in U.S. Pat. Nos. 4,716,175 and 4,743,605 (a divisional of the '175 patent) and in the European Patent Applications having publication numbers 0 242 610, 0 245 687 and 0 252 524. Certain ureas and thioureas as antiatherosclerosis agents are referred to in U.S. Pat. No. 4,623,662.

SUMMARY OF THE INVENTION

The present invention relates to compounds of the formula

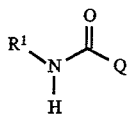

I wherein Q is —$CR^2R^3R^4$ or —$NR^{17}R^{18}$;

$R^1$ is

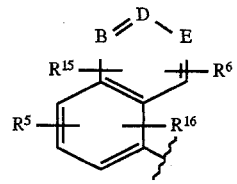

XXIV

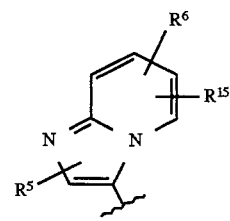

XXV

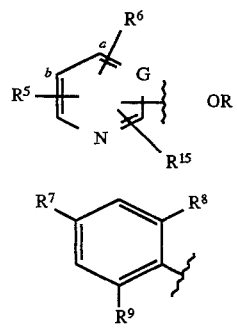

XXVI

OR

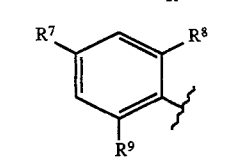

XXVII $R^2$, $R^3$ and $R^4$ may be the same or different, and (a) are selected from the group consisting of hydrogen, ($C_1$–$C_4$) alkyl, A, $XR^{10}$, phenyl-($C_1$–$C_7$) alkyl, and ($C_5$–$C_6$) cycloalkyl-($C_1$–$C_6$) alkyl, with the proviso that at least one of $R^2$, $R^3$ and $R^4$ must be A, and with the proviso that when $R^1$ is a group of the formula XXVII or a group of the formula XXVI wherein G is nitrogen and wherein neither $R^5$, $R^6$ nor $R^{15}$ is $NR^{19}R^{20}$, ($C_1$–$C_6$) alkylthio, ($C_5$–$C_7$) cycloalkylthio, phenyl ($C_1$–$C_4$) alkylthio, phenylthio or heteroalkylthio, either at least one of $R^2$, $R^3$ and $R^4$ must be $XR^{10}$, or two of $R^2$, $R^3$ and $R^4$ must be A; or (b) $R^2$ and $R^3$ together with the carbon to which they are attached form a cyclic or bicyclic system selected from the group consisting of ($C_3$–$C_7$) cycloalkyl, ($C_3$–$C_7$) cycloalkenyl, ($C_6$–$C_{14}$) bicycloalkyl, ($C_6$–$C_{14}$) bicycloalkenyl, and aryl-fused systems containing 8 to 15 carbon atoms, one ring of any of said aryl-fused systems being aromatic and the ring containing the carbon to which $R^2$ and $R^3$ are attached being non-aromatic, one of the carbons of said aromatic ring being optionally replaced by sulfur or oxygen, one or more carbons of said non-aromatic ring being optionally replaced by sulfur or oxygen, one or two carbons of said cycloalkyl or bicycloalkyl groups being optionally replaced by sulfur or oxygen, and said cyclic or bicyclic system being optionally substituted with one to five substituents independently selected from the group consisting of phenyl, substituted phenyl, ($C_1$–$C_6$) alkyl and A, with the proviso that one and only one of said substituents is A, and one and only one of said substituents is phenyl or substituted phenyl, said substituted phenyl being substituted with one or more substituents independently selected from the group consisting of ($C_1$–$C_6$) alkyl, ($C_1$–$C_6$) alkylthio, halogen and trifluoromethyl; and $R^4$ is hydrogen, $XR^{10}$ or A;

with the proviso that when $R^1$ is a group of the formula XXVII or a group of the formula XXVI wherein G is nitrogen and wherein neither $R^5$, $R^6$ nor $R^{15}$ is $NR^{19}R^{20}$, ($C_1$–$C_6$) alkylthio, ($C_5$–$C_7$) cycloalkylthio, phenyl ($C_1$–$C_4$)

alkylthio, phenylthio or heteroalkylthio, $R^2$ and $R^3$, together with the carbon to which they are attached, do not form a ($C_3C_7$) cycloalkyl ring containing only carbon atoms;

A is a hydrocarbon containing 4 to 16 carbons and 0, 1 or 2 double bonds;

X is O, S, SO, $SO_2$, NH, $NR^{23}CO$ or $NSO_2R^{24}$, wherein $R^{23}$ is hydrogen or ($C_1$–$C_6$) alkyl and $R^{24}$ is ($C_1$–$C_6$) alkyl, phenyl or ($C_1$–$C_3$) alkyl-phenyl;

$R^5$, $R^6$, $R^{15}$ and $R^{16}$ are each independently selected from the group consisting of hydrogen, fluoro, chloro, bromo, iodo, ($C_1$–$C_4$)alkyl, ($C_1$–$C_4$) haloalkyl, ($C_1$–$C_4$) alkoxy, ($C_1$–$C_6$) alkylthio, ($C_5$–$C_7$) cycloalkylthio, phenyl ($C_1$–$C_4$) alkylthio, substituted phenylthio, heteroarylthio, heteroaryloxy, and $NR^{19}R^{20}$, wherein $R^{19}$ and $R^{20}$ are the same or different and are selected from the group consisting of hydrogen, ($C_1$–$C_4$) alkyl, phenyl, substituted phenyl, ($C_1$–$C_4$) acyl, aroyl, and substituted aroyl, wherein said substituted phenyl and substituted aroyl groups are substituted with one or more substituents independently selected from the group consisting of ($C_1$–$C_6$) alkyl, ($C_1$–$C_6$) alkoxy, ($C_1$–$C_6$) alkylthio, halogen and trifluoromethyl, or $R^{19}$ and $R^{20}$, together with the nitrogen to which they are attached, form a piperidine or morpholine ring; and wherein $R^5$, $R^6$, $R^{15}$ and $R^{16}$, when attached to a bicyclic system, may be attached to either ring of such system, with the proviso that no more than 3 non-hydrogen substituents may be attached to any one ring of such system;

$R^7$, $R^8$ and $R^9$ are the same or different; $R^7$ is selected from the group consisting of hydrogen, ($C_1$–$C_4$) alkoxy, ($C_1$–$C_4$) alkylthio, methyl and fluoro; and $R^8$ and $R^9$ are each independently selected from the group consisting of ($C_1$–$C_4$) alkoxy, ($C_1$–$C_4$) alkylthio, methyl, and fluoro;

$R^{10}$ is selected from the group consisting of ($C_4$–$C_{12}$) cycloalkyl, ($C_4$–$C_{12}$) straight or branched alkyl, ($C_4$–$C_{12}$) cycloalkyl-($C_1$–$C_6$) alkyl, phenyl-($C_1$–$C_6$) alkyl, (substituted phenyl)-($C_1$–$C_6$) alkyl, ($C_1$–$C_6$) alkyl-phenyl, ($C_1$–$C_6$) alkyl-(substituted phenyl), substituted thiazoles, substituted benzothiazoles, and substituted pyridines; wherein the substituents on the substituted phenyl, substituted thiazoles, substituted benzothiazoles and substituted pyridines are selected from the group consisting of ($C_1$–$C_4$) alkoxy, ($C_1$–$C_4$) alkylthio, ($C_1$–$C_6$) alkyl, halo and trifluoromethyl;

B, D, E and G are selected from the group consisting of nitrogen and carbon, with the proviso that one or more of B, D and E is nitrogen, and with the proviso that when G is nitrogen, the group XXVI is attached to the nitrogen of formula I at the 4 or 5 position of the pyrimidine ring (designated by a and b);

and $R^{17}$ and $R^{18}$ are each independently selected from the group consisting of ($C_4$–$C_{12}$) straight or branched alkyl, phenyl-($C_1$–$C_4$) alkyl, and ($C_1$–$C_6$) alkylphenyl-($C_1$–$C_6$) alkyl;

with the proviso that when Q is $NR^{17}R^{18}$, $R^1$ is a group of the formula XXVI or XXIV, or a group of the formula XXVII wherein $R^7$, $R^8$ and $R^9$ are each methoxy.

Examples of said aryl-fused and heteroaryl-fused systems are:

1,2,3,4-tetrahydronapthalene, 5,6,7,8,9-pentahydrobenzocycloheptene, 5,6,7,8,9,10-hexahydrobenzocyclooctene, 4,5,6-trihydro-1-thiapentalene, 4,5,6-trihydro-2-thiapentalene, 4,5,6,7-tetrahydrobenzo[b]thiophene, 4,5,6,7-tetrahydrobenzo[c]thiophene, 4,5,6-trihydro-1-oxapentalene, 4,5,6,7-tetrahydrobenzo[b]furan, 4,5,6-trihydro-1-azapentalene, 4,5,6,7-tetrahydrobenzo[b]pyrrole, 4,5,6-trihydro-1-oxa-3-azapentalene, 4,5,6,7-tetrahydrobenzo[d]oxazole, 4,5,6-trihydro-1-thia-3-azapentalene 4,5,6,7-tetrahydrobenzo[d]thiazole, 4,5,6-trihydro-1-oxa-2-azapentalene, 4,5,6,7-tetrahydrobenzo[d]oxazole, 4,5,6-trihydro-1-thia-2-azapentalene, 4,5,6,7-tetrahydrobenzo[d]thiazole, 4,5,6-trihydro-1,2-diazapentalene, 4,5,6,7-tetrahydrobenzo[d]pyrazole, 4,6-diazaindane and 5,6,7,8-tetrahydroquinazoline.

Unless otherwise indicated, the term "halo", as used herein, includes fluoro, chloro, bromo and iodo.

Unless otherwise indicated, the term "alkyl", as used herein, may be straight, branched or cyclic, and may include straight and cyclic moieties as well as branched and cyclic moieties.

Unless otherwise indicated, the term "one or more substituents", as used herein, refers to from one to the maximum number of substituents possible based on the number of available bonding sites.

The term "one or more carbons of said non-aromatic ring", as used herein, refers to from one to all of the carbon atoms that are part of the non-aromatic ring of any of the aryl-fused systems described above, and not part of the aromatic ring of said aryl-fused system.

The term "one or more carbons of said aromatic ring", as used herein, refers to from one to all of the carbon atoms that are part of the aromatic ring of any of the aryl-fused and heteroaryl-fused systems described above, or are part of both said aromatic and non-aromatic rings of said aryl-fused and heteroaryl-fused system.

The compounds of formula I may have optical centers and therefore may occur in different stereoisomeric configurations. The invention includes all stereoisomers of such compounds of formula I, including mixtures thereof.

The present invention also relates to compounds of the formula

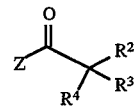

II wherein Z is hydroxy, halo or other acylation functional group such as acyloxy wherein said acyl group is $R^2R^3R^4C$ (═O)— or different; $R^2$, $R^3$ and $R^4$ are each independently selected from the group consisting of ($C_6$–$C_{16}$) alkyl, ($C_6$–$C_{16}$) alkenyl containing 1 or 2 double bonds, phenyl-($C_1$–$C_6$) alkyl, ($C_5$–$C_6$) cycloalkyl-($C_1$–$C_6$) alkyl, $XR^{10}$, and hydrogen, with the proviso that at least one of $R^2$, $R^3$ and $R^4$ is ($C_6$–$C_{16}$) alkyl or ($C_6$–$C_{16}$) alkenyl containing 1 or 2 double bonds; or $R^2$ and $R^3$, together with the carbon to which they are attached, form a cyclic or bicyclic ring system selected from the group consisting of

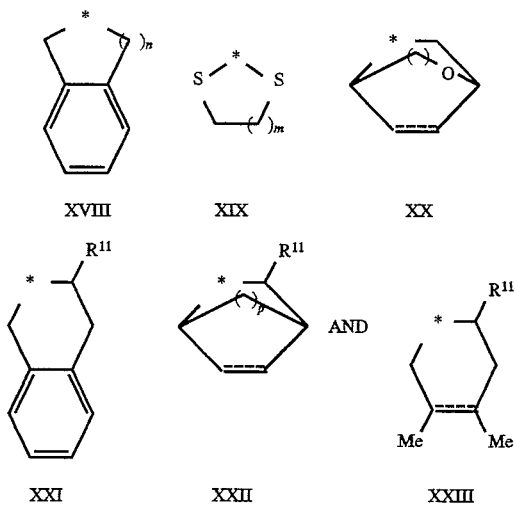

XVIII  XIX  XX

XXI  XXII  XXIII and aryl-fused and heteroaryl-fused systems containing 8 to 15 carbon atoms, one ring of any of said aryl-fused and heteroaryl-fused systems being aromatic and the other ring containing the carbon to which $R^2$ and $R^3$ are attached being non-aromatic, one of the carbons of said aromatic ring being optionally replaced by sulfur or oxygen, one or more carbons of said non-aromatic ring being optionally replaced by sulfur or oxygen, and one or more carbons of said aromatic ring being optionally replaced by nitrogen;

and wherein $R^4$ is hydrogen, A or $XR^{10}$; A is a hydrocarbon containing 4 to 16 carbons and 0, 1 or 2 double bonds; X is oxygen or sulfur; $R^{10}$ is selected from the group consisting of $(C_4-C_{12})$ cycloalkyl, $(C_4-C_{12})$ straight or branched alkyl, $(C_4-C_{12})$ cycloalkyl-$(C_1-C_6)$ alkyl, phenyl-$(C_1-C_6)$ alkyl, (substituted phenyl)-$(C_1-C_6)$ alkyl, $(C_1-C_6)$ alkyl-phenyl, $(C_1-C_6)$ alkyl-(substituted phenyl), substituted thiazoles, substituted benzothiazoles, and substituted pyridines, wherein the substituents on the substituted phenyl, substituted thiazoles, substituted benzothiazoles and substituted pyridines are selected from the group consisting of $(C_1-C_4)$ alkoxy, $(C_1-C_4)$ alkylthio, $(C_1-C_6)$ alkyl, halo and trifluoromethyl; $R^{11}$ is $(C_6-C_{12})$ alkyl or $(C_6-C_{12})$ alkenyl containing 1 or 2 double bonds; n and m are each independently 1 or 2; o and p are each independently 0, 1 or 2; each broken line represents an optional double bond; and each asterisk represents the carbon to which $R^2$ and $R^3$ are attached; with the proviso that when $R^2$ and $R^3$ form any of ring systems XVIII, XIX and XX, $R^4$ is A or $XR^{10}$, and when $R^2$ and $R^3$ form any of ring systems XXI, XXII and XXIII, $R^4$ is hydrogen; and with the proviso that when $R^2$ and $R^3$ do not form a ring system, no more than one of $R^2$, $R^3$ and $R^4$ is hydrogen. The compounds of formula II are intermediates used in the synthesis of compounds of the formula I.

Specific compounds of the formula II are: 2-(hexylthio) octanoic acid, 2-(hexylthio)nonanoic acid, 2-(hexylthio) decanoic acid, 2-(heptylthio)octanoic acid, 2-(heptylthio) nonanoic acid, 2-(heptylthio)decanoic acid, 2-nonylindan-2-yl carboxylic acid, 2-decylindan-2-yl carboxylic acid, 2-octyl-1,2,3,4-tetrahydronaphth-2-yl carboxylic acid and 2-nonyl-1,2,3,4-tetrahydronaphth-2-yl carboxylic acid.

The present invention also relates to compounds of the formula

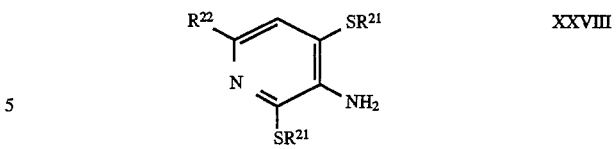

XXVIII wherein
$R^{21}$ is $(C_1-C_3)$ alkyl and $R^{22}$ is hydrogen or $(C_1-C_3)$ alkyl.

Preferred compounds of formula I are those wherein $R^1$ is 2,4,6-trifluorophenyl, 2,4,6-trimethoxyphenyl, 6-methoxyquinolin-5-yl, 6-methylthioquinolin-5-yl, 6-methoxyisoquinolin-5-yl, 6-methylthioisoquinolin-5-yl, 6-methylthio-8-acetaminoquinolin-5-yl, 2-methyl-4,6-di(methylthio)pyrimidin-5-yl, and 6-methyl-2,4-di(methylthio)pyridin-3-yl.

Other preferred compounds of formula I are those wherein:

$R^2$ is hexylthio, $R^3$ is octyl and $R^4$ is hydrogen; or $R^2$ and $R^3$ together with the carbon to which they are attached form an indan-2-yl ring, and $R^4$ is 2-decyl; or $R^2$ and $R^3$ together with the carbon to which they are attached form a 1,2,3,4-tetrahydronaphth-2-yl ring and $R^4$ is nonyl.

Specific preferred compounds of formula I are:

N-(2,4,6-trifluorophenyl)-2-(hexylthio) octanoic amide;

N-(2,4,6-trimethoxyphenyl)-2-(hexylthio) octanoic amide;

N-(2,4,6-trimethoxyphenyl)-2-(6-ethoxybenzothiazol-2-yl)decanoic amide;

N-(6-methoxyquinolin-5-yl)-2-(hexylthio) decanoic amide;

N-(6-methylthioquinolin-5-yl)-2-(hexylthio) decanoic amide;

N-(6-methoxyisoquinolin-5-yl)-2-(hexylthio) decanoic amide;

N-(6-methylthio-8-acetaminoquinolin-5-yl)-2-(hexylthio) decanoic amide;

N-(6-methylthioisoquinolin-5-yl)-2-(hexylthio) decanoic amide;

N-(6-methylisoquinolin-5-yl)-2-(hexylthio) decanoic amide;

N-(6-methylthioquinolin-5-yl)-2-(4-(3-methylpropyl)phenoxy) nonanoic amide;

(2S)-N-[2,4-bis(methylthio)-6-methylpyridin-3-yl]-2-hexylthiodecanoic amide;

(2S)-N-[2-methyl-4,6-bis(methylthio)pyrimidin-5-yl]-2-hexylthiodecanoic amide;

(2S)-N-[6-(methylthio)quinolin-5-yl]-2-hexylthiodecanoic amide;

N-[4,6-bis(methylthio)-2-methylpyrimidin-5-yl]-2-hexylthiodecanoic amide;

N-[2,4-bis(methylthio)-6-methylpyridin-3-yl]-2-hexylthiodecanoic amide;

N-[4,6-bis(methylthio)-2-methylpyrimidin-5-yl]-2,2-dimethyldocecanoic amide;

N-[2,4-bis(methylthio)-6-methylpyridin-3-yl]-2,2-dimethyldodecanoic amide;

N'-[2,4-bis(methylthio)-6-methylpyridin-3-yl]-N-[4-(3-methylbutyl)benzyl]-N-cycloheptylurea;

N'-[2,4-bis(methylthio)-6-methylpyridin-3-yl]-N-[4-(3-methylbutyl)benzyl]-N-heptylurea;

N'-[4,6-bis(methylthio)-2-methylpyrimidin-5-yl]-N-[4-(3-methylbutyl)benzyl]-N-cycloheptylurea;

N'-[4,6-bis(methylthio)-2-methylpyrimidin-5-yl]-N-[4-(3-methylbutyl)benzyl]-N-heptylurea;

N-[4,6-bis(methylthio)-2-methylpyrimidin-5-yl]-4,5-dimethyl-trans-2-heptylcyclohex-4-ene-carboxamide;

N-[4,6-bis(methylthio)-2-methylpyrimidin-5-yl]-2-heptylnonanoic amide;

N-[4,6-bis(methylthio)-2-methylpyrimidin-5-yl] pentadecanoic amide;

N-[2,4-bis(methylthio)-6-methylpyridin-3-yl-] pentadecanoic amide;

N-[2,4-bis(methylthio)-6-methylpyridin-3-yl]-(Z)-9-octadecenoic amide;

N-[4,6-bis(methylthio)-2-methylpyrimidin-5-yl]-(Z)-9-octadecenoic amide;

N-[4,6-bis(methylthio)-2-methylpyrimidin-5-yl]-trans-3-nonyl-1,2,3,4-tetrahydro-2-naphthoic amide;

N-[4,6-bis(methylthio)pyrimidin-5-yl]-trans-3-nonyl-1,2,3,4-tetrahydro-2-naphthoic amide;

N-(2,4,6-trimethoxyphenyl)-2-nonyl-1,2,3,4-tetrahydro-napth-2-yl carboxamide;

N-(2,4,6-trifluorophenyl)-2-nonyl-1,2,3,4-tetrahydro-napth-2-yl carboxamide;

N-(2,4,6-trifluorophenyl)-2-nonylindan-2-yl carboxamide;

N-(2,4,6-trimethoxyphenyl)-6-trans-heptyl-3,4-dimethyl-cyclohex-2-enylcarboxamide;

N-(2,4,6-trimethoxyphenyl)-2-nonylbicyclo[2.2.1]-hept-5-en-2-yl carboxamide;

N-(6-methylthioquinolin-5-yl)-2-octyl-1,3-dithian-2-yl carboxamide;

N-(2-methyl-4,6-dimethylthiopyrimidin-5-yl)-2-hexylthiodecanoic amide;

N-(2,4,6-trimethoxyphenyl)-N'-(4-(3-methylbutyl)phenylmethyl)-N'-heptylurea;

N-(2,4,6-trimethoxyphenyl)-N'-(4-(2,2-dimethylpropyl)phenylmethyl)-N'-heptylurea;

N-(isoquinolin-5-yl)-N'-(4-(3-methylbutyl)phenylmethyl)-N'-heptylurea;

N-(quinolin-5-yl)-N'-(4-(3-methylbutyl)phenylmethyl)-N'-heptylurea; and

N-(6-methoxyquinolin-5-yl)-N'-(4-(3-methylbutyl)phenylmethyl)-N'-heptylurea.

Other compounds of formula I are:

N-(2-methoxy-6-methylphenyl)-2-(4-propylphenyl)sulfonylundecanoic amide;

N-(3-methyl-6-trifluoromethylquinolin-5-yl)-2-(2,5-dimethylphenoxy)decanoic amide;

N-(6,7-(methylenedioxy)isoquinolin-5-yl)-2-(thiazol-2-yl)methoxynonanoic amide;

N-(2,6-dimethoxyphenyl)-2,2-di(isopropylthio)-octanoic amide;

N-(3-chloro-8-isobutylquinolin-5-yl)-2-(3-ethoxyphenyl)thio-2-propylheptanoic amide;

N-(4-methyl-6,7-difluoroisoquinolin-5-yl)-1-methyl-5-octyl-2,7-dioxabicyclo[2.2.1]heptan-5-yl carboxamide;

N-(2,4,6-trimethoxyphenyl)-2-propylthiohexadec9-enoic amide;

N-(6-isopropylthioquinolin-5-yl)-2-(4-ethylthiophenoxy)non anoic amide; N-(6-methoxyisoquinolin-5-yl)-2-[5-chlorobenzthiazol-2-yl) thiodectanoic amide;

N-(2,4,6-trifluorophenyl)-2-[(3,5-dimethylbenzoyl)amino]octanoic amide;

N-(8-acetamino-6-methoxyquinolin-5-yl)-2-hexylthiodecanoic amide;

N-(8-amino-6-methoxyquinolin-5-yl)-2-hexylthiodecanoic amide;

N-(8-amino-6-methylthioquinolin-5-yl)-2-hexylthiodecanoic amide;

N-(8-(2,2-dimethylpropionyl)amino-6-methoxyquinolin-5-yl)-2-hexylthiodecanoic amide;

N-(8-(2,2-dimethylpropionyl)amino-6-methoxyquinolin-5-yl)-2-hexylthiodecanoic amide;

N-(6-methylthioquinolin-5-yl)-2-hexyloxydecanoic amide;

N-(8-acetamino-6-methylthioquinolin-5-yl)-2-hexyloxydecanoic amide;

N-(6-methylthioquinolin-5-yl)-2-heptylnonanoic amide;

N-(8-acetamino-6-methylthioquinolin-5-yl)-2-heptylnonanoic amide;

N-(8-acetaminoquinolin-5-yl)-2-hexylthiodecanoic amide;

N-(8-aminoquinolin-5-yl)-2-hexylthiodecanoic amide;

N-(6-acetaminoquinolin-5-yl)-2-hexylthiodecanoic amide;

N-(6-aminoquinolin-5-yl)-2-hexylthiodecanoic amide;

N-(4,6-dimethylthiopyrimidin-5-yl)-2-hexylthiodecanoic amide;

N-(4,6-diethylthiopyrimidin-5-yl)-2-hexylthiodecanoic amide;

N-(4-methoxy-6-ethylthiopyrimidin-5-yl)-2-hexylthiodecanoic amide;

N-(4-ethoxy-6-methylthiopyrimidin-5-yl)-2-hexylthiodecanoic amide;

N-(4-ethoxy-6-ethylthiopyrimidin-5-yl)-2-hexylthiodecanoic amide;

N-(4-methoxy-6-ethoxyethylthiopyrimidin-5-yl)-2-hexylthiodecanoic amide;

N-(4-methoxy-6-butylthiopyrimidin-5-yl)-2-hexylthiodecanoic amide;

N-(2,4-dimethylthio-6-methylpyrimidin-5-yl)-2-heptylnonanoic amide;

N-(2-amino-4-methoxy-6-methylthiopyrimidin-5-yl)-hexylthiodecanoic amide;

N-(2-acetamino-4-methoxy-6-methylthiopyrimidin-5-yl)-2-hexylthiodecanoic amide;

N-[4-methoxy-6-(2-furylmethylthio)pyrimidin-5-yl]-2-hexylthiodecanoic amide;

N-[4-methoxy-6-(2-propylthio)pyrimidin-5-yl]-2-hexylthiodecanoic amide;

N-(2-butylthio-4-methylpyridin-3-yl)-2-hexylthiodecanoic amide;

N-[2-(4-methoxyphenylthio)-4-methylpyridin-3-yl]-2-hexylthiodecanoic amide;

N-[2-(2-furylmethylthio)-4-methylpyridin-3-yl]-2-hexylthiodecanoic amide;

N-(2-ethylthio-4-methylpyridin-3-yl)-2-hexylthiodecanoic amide;

N-(6-methoxyquinolin-5-yl)-9-octadecenoic amide;
N-(6-fluoroquinolin-5-yl)-9-octadecenoic amide;
N-(6-methylthioquinolin-5-yl)-9-octadecenoic amide;
N-(8-acetamino-6-methylthio-quinolin-5-yl)-9-octadecanoic amide;

N-(2-ethylthio-4-methylpyridin-3-yl)-4,5-dimethyl-trans-2-nonylcyclohex-4-enecarboxamide; and N-(4,6-dimethylthiopyrimidin-5-yl)-2-decylindane-2-carboxamide.

The present invention also relates to all radiolabelled forms of the compounds of the formulae I, II and XXVIII. Such radiolabelled compounds are useful as research and diagnostic tools in metabolism pharmacokinetic studies and in binding assays in both animals and man.

The present invention also relates to a pharmaceutical composition for inhibiting ACAT, inhibiting intestinal absorption of cholesterol, reversing or slowing the development of atherosclerosis, or lowering the concentration of serum cholesterol in a mammal, including a human, comprising an amount of a compound of the formula I, or a pharmaceutically acceptable salt thereof, effective in inhibiting ACAT, inhibiting intestinal absorption of cholesterol, reversing or slowing the development of atherosclerosis, or lowering the concentration of serum cholesterol, and a pharmaceutically acceptable carrier.

The present invention also relates to a method for inhibiting ACAT, inhibiting intestinal absorption of cholesterol, reversing or slowing the development of atherosclerosis, or lowering the concentration of serum cholesterol in a mammal, including a human, comprising administering to a mammal an amount of a compound of the formula I, or a pharmaceutically acceptable salt thereof, effective in inhibiting ACAT, inhibiting intestinal absorption of cholesterol, reversing or slowing the development of atherosclerosis, or lowering the concentration of serum cholesterol.

Examples of pharmaceutically acceptable acid addition salts of the compounds of formula I salts are the salts of hydrochloric acid, p-toluenesulfonic acid, fumaric acid, citric acid, succinic acid, salicyclic acid, oxalic acid, hydrobromic acid, phosphoric acid, methanesulfonic acid, tartaric acid, di-p-toluoyl tartaric acid, and mandelic acid.

DETAILED DESCRIPTION OF THE INVENTION

Reaction schemes 1–4 below illustrate the synthesis of the compounds of this invention. The compounds of formula I designated in the reaction schemes by the formulae IA, IB, IC, and ID, depending on the method by which they prepared. Scheme 5 below illustrates the synthesis of certain 5-aminoquinolines and 5-aminoisoquinolines used as reactants in scheme 1–4.

Except where otherwise stated, Q, $R^1$, $R^2$, $R^3$, $R^4$, $R^5$, $R^6$, $R^7$, $R^8$, $R^9$, $R^{10}$, $R^{11}$, $R^{15}$, $R^{16}$, $R^{17}$, $R^{18}$, n, m, o, p, X, A, B, D, and G in the reaction schemes and discussion that follows are defined as above.

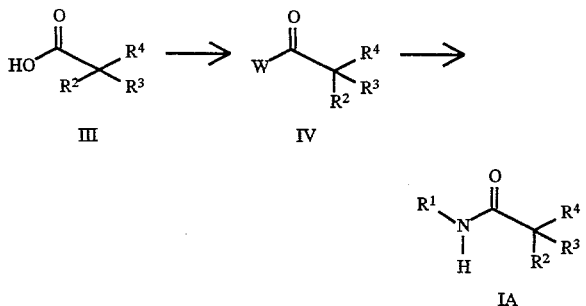

Scheme 1 represents the synthesis of amides of the present invention having the formula IA, i.e., compounds of the formula I wherein Q is —$CR^2R^3R^4$, from the corresponding carboxylic acid having the formula III. An acid of formula III is first converted to the corresponding acid halide of formula IV, wherein W is chloro or bromo, by reacting it with a chlorinating or brominating agent. Examples of suitable chlorinating and brominating agents are oxalyl chloride, oxalyl bromide, thionyl chloride, thionyl bromide, phosphorous trichloride, phosphorous tribromide, phosphorous pentachloride, phosphorous pentabromide, phosphorous oxychloride, and phosphorous oxybromide. This reaction is typically carried out in the absence of a solvent or, alternatively, in the presence of a halogenated hydrocarbon solvent such as methylene chloride, for from about 0.5 to 48 hours (preferably from about 2 to 18 hours) at a temperature from about 0°–250° C. (preferably at the reflux temperature of the reaction mixture). The acid halide so formed is then converted to the corresponding amide of the formula IA by reacting it with an amine of the formula $R^1NH_2$ and an acid scavenger such as dimethylaminopyridine, pyridine or triethylamine. This reaction is typically carried out in the absence of a solvent or in the presence of an inert solvent such as tetrahydrofuran or methylene chloride for from about 0.25 to 144 hours (preferably from about 2 to 72 hours) at a temperature from about −78° to 350° C. (preferably from about −20 to the reflux temperature of the reaction mixture).

Compounds of the formula I, wherein Q is $-CR^2R^3R^4$, $R^2$ is $XR^{10}$, one of $R^3$ and $R^4$ is hydrogen and the other is selected from hydrogen, $(C_1-C_4)$ alkyl or A, i.e., compounds of the formula IB, may be prepared as illustrated in scheme 2. Referring to scheme 2, a carboxylic acid of the formula V, wherein one of $R^3$ and $R^4$ is hydrogen and the other is selected from hydrogen, $(C_1-C_4)$ alkyl or A, is reacted for about 3 hours with thionyl chloride using no solvent, at the reflux temperature of the reaction mixture. Bromine and a catalytic amount of iodine are then added to the reaction mixture, and the resulting mixture is brought to reflux. After refluxing for about 18 hours, ethanol is added and the mixture is refluxed for about 1 more hour to produce a bromoester of the formula VI, wherein $R^3$ and $R^4$ are defined as they are for formula V above. The bromoester of formula VI is then converted to an ester having the same formula as formula VI except that the substituent −Br is replaced by the substituent $-XR^{10}$, (hereinafter referred to as formula VI'), by reacting it with a compound of the formula $HXR^{10}$ and a base such as potassium carbonate or sodium hydride in an aprotic, polar solvent such as dimethylformamide, acetone or tetrahydrofuran, for about 0.5 to 48 hours (preferably from about 4 to 18 hours) at a temperature from about −78° to 350° C. (preferably from about 0° C. to the reflux temperature of the reaction mixture). An acid of the formula VII, wherein $R^3$ and $R^4$ are defined as they are for formulas V and VI above, is then prepared by reacting the ester having formula VI' with a hydroxide such as sodium hydroxide. This reaction is typically carried out overnight in an lower alcohol solvent such as methanol or ethanol, at a temperature from about −78° to 350° C. (preferably from about 20° C. to the reflux temperature of the reaction mixture).

The acid of formula VII so prepared is then converted to an amide of the formula IB, wherein $R^3$ and $R^4$ are defined as they are for formulae V, VI and VII above, by the acid to amide synthesis illustrated in scheme 1 and described above.

Compounds of the formula IB, may be prepared, alternatively, by the following method. A compound of the formula V, as illustrated in scheme 2 and defined above, is reacted with thionyl chloride followed by bromine and a catalytic amount of iodine as described above, but quenching the reaction with water instead of ethanol, to form a compound of the formula $HOOCCBrR^3R^4$, wherein $R^3$ and $R^4$ are defined as they are for formula V. This compound is then converged, sequentially, to the corresponding acid chloride of the formula $ClCOCBrR^3R^4$ and the corresponding amide of the formula $R^1NHCOCBrR^3R^4$, wherein $R^3$ and $R^4$ are defined as they are for formula V, by the acid to amide synthesis illustrated in scheme 1 and described above. The amide of the formula $R^1NHCOCBrR^3R^4$ so formed is then reacted with a compound of the formula $HXR^{10}$ and a base such as potassium carbonate and sodium hydride to form a compound having the formula IB, wherein $R^3$ and $R^4$ are defined as they are for formula V. This reaction is typically carried out in an aprotic, polar solvent such as dimethylformamide, acetone or tetrahydrofuran, for from about 0.5 to 48 hours (preferably from about 4 to 18 hours). The reaction may be carried out at temperatures ranging from about −78° to 350° C. (preferably from about 0° C. to the reflux temperature of the reaction mixture).

Scheme 3 illustrates the preparation of compounds of formula I, wherein Q is $CR^2R^3R^4$, $R^4$ is hydrogen or A, and $R^2$ and $R^3$, together with the carbon to which they are attached, form the bicyclic ring system

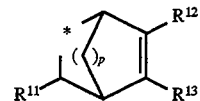

wherein the asterisk designates the carbon to which $R^2$ and $R^3$ are attached, and each of $R^{12}$ and $R^{13}$ are independently selected from the group consisting of hydrogen and $(C_1-C_4)$ alkyl, or $R^{12}$ and $R^{13}$, together with the carbons to which they are attached, form a benzene ring.

As illustrated in scheme 3, a Diels-Alder reaction is carried out between an acid of the formula XIII, wherein $R^{11}$ is A, hydrogen, phenyl or substituted phenyl, and wherein $R^{11}$ and the carboxyl group are trans to each other, and a diene of the formula IX, wherein $R^{12}$ and $R^{13}$ are as defined above. This reaction is typically carried out in a hydrocarbon solvent such as toluene, using a catalytic amount of an antioxidant such as hydroquinone. The reagents are generally reacted for about 1 to 10 days (preferably for about 3 to 5 days) in a sealed, high pressure apparatus at a temperature from about room temperature to 350° C. (preferably from about 100° to 150° C.). The reaction yields an acid of the formula X, which can be converted to the corresponding amide of the formula IC, wherein the carbons to which $R^{12}$ and $R^{13}$ are attached are bonded by a carbon-carbon double bond, by the acid to amide synthesis illustrated in scheme 1 and described above. The amide of formula IC so formed can be converted to an amide of the formula IC, wherein the carbons to which $R^{12}$ and $R^{13}$ are attached are bonded by a carbon-carbon single bond, by reacting it with a reducing agent such as hydrogen. Typically, the reduction is carried out using hydrogen gas in a high pressure apparatus, in an inert solvent such as acetic acid, and in the presence of a hydrogenation catalyst such as palladium on carbon. The reduction maybe carried out at temperatures ranging from about −20° to 250° C. (preferably at room temperature). Fifty p.s.i. of hydrogen is the preferred pressure, through pressures greater than or equal to 1 atmosphere are suitable. The corresponding compound of formula IC, wherein the carboxyl group and $R^{11}$ are cis to each other, may be prepared in a similar manner, but using the corresponding cis isomer of the acid of formula XIII.

When the procedure of scheme 3 described above is used to prepare a compound of formula IC wherein $R^{12}$ and $R^{13}$, together with the carbon to which they are attached, form a benzene ring, the diene of formula IX is generally generated in situ in the presence of the acid of formula XIII or its ester by heating a mixture of 1,3-dihydrobenzo[c]thiophene 2,2-dioxide and such acid or ester. This reaction is typically carried out at a temperature of from about 235° to 300° C. (preferably from about 250° to 265° C.) under nitrogen for approximately from 0.5 to 24 hours (preferably for about 2 hours).

Scheme 4 illustrates the preparation of compounds of the formula I, wherein Q is —$CR^2R^3R^4$, $R^4$ is ($C_1$–$C_4$) alkyl or A, and $R^2$ and $R^3$ are each independently selected from the group consisting of hydrogen, ($C_1$–$C_4$) alkyl, A or $XR^{10}$; or $R^2$ and $R^3$, together with the carbon to which they are attached, form a cyclic or bicyclic system selected from the group consisting of ($C_3$–$C_7$) cycloalkyl, ($C_6$–$C_{14}$) bicycloalkyl, one or two carbons of said cycloalkyl and bicycloalkyl groups being optionally replaced with oxygen or sulfur; and aryl-fused and heteroaryl-fused systems containing 8 to 15 carbon atoms, one ring of any of said aryl-fused and heteroaryl-fused systems being aromatic and the ring containing the carbon to which $R^2$ and $R^3$ are attached being non-aromatic, one of the carbons of said aromatic ring being optionally replaced by sulfur or oxygen, one or more carbons of said non-aromatic ring being optionally replaced by sulfur or oxygen, and one or more carbons of said aromatic ring being optionally replaced by nitrogen. It also illustrates the preparation of compounds of the formula I, wherein Q is —$CR^2R^3R^4$, $R^4$ is $XR^{10}$, and $R^2$ and $R^3$, together with the carbon to which they are attached, form a cyclic or bicyclic system as defined immediately above. All compounds of the invention illustrated in scheme 4 are designated by the formula ID and are prepared by the following procedure.

An acid of the formula XI, wherein $R^2$ and $R^3$ are each independently selected from the group consisting of hydrogen, ($C_1$–$C_4$) alkyl, A or $XR^{10}$, or $R^2$ and $R^3$ together with the carbon to which they are attached, form a cyclic or bicyclic system as defined immediately above, is reacted with a base such as lithium diisopropylamide or hexamethyldisilazide, with or without an additive such as hexamethylphosphorous triamide, in a dry inert solvent such as tetrahydrofuran, and then reacted with a compound of the formula $R^4$Hal, wherein Hal is halogen and $R^4$ is ($C_1$–$C_7$) alkyl or A. The reaction is typically carried out at a temperature from about −78° to 40° C. (preferably from about −78° C. to room temperature) for about 0.5 to 48 hours (preferably for about 1.5 to 17 hours: 0.5 to 1 hour to generate the dianion of formula XI and 1 to 16 hours for the alkylation). The product of the reaction is an acid of the formula XII, wherein $R^2$ and $R^3$ are as defined immediately above, and $R^4$ is ($C_1$–$C_7$) alkyl or A. The acid of formula XII so formed may be converted to the corresponding amide of the formula ID, wherein $R^2$ and $R^3$ are as defined immediately above and $R^4$ is ($C_1$–$C_7$) alkyl or A, by the acid to amide synthesis illustrated in scheme 1 and described above.

Compounds of the formula ID, wherein $R^4$ is $XR^{10}$, are prepared by the same procedure as that described above for the preparation of compounds of the formula ID wherein $R^4$ is ($C_1$–$C_7$) alkyl or A, with one modification. The dianion of formula XI is reacted with a compound of formula $R^{10}SSR^{10}$ instead of Hal$R^4$. This reaction produces an acid of the formula XII, wherein $R^4$ is $XR^{10}$. The acid of the formula XII so formed can then be converted to the corresponding amide of formula ID by the acid to amide synthesis illustrated in scheme 1 and described above.

The aminopyrimidine and aminopyridine intermediates used in the present invention are known in the literature or may be prepared by methods known in the art from intermediates that are known in the literature or commercially available. References for the preparation of many of the pyrimidine and pyridine intermediates can be found in the monographs "The Pyrimidines", ed. by D. J. Brown (1962) and "Pyridine and its Derivatives", ed. by R. A. Abramovitch (1961), Interscience Publishers, Inc., New York, N.Y., and their supplements. The preparation of certain of these intermediates is described in greater detail below.

2,6-Disubstituted-5-amino-pyrimidine derivatives may be prepared by reacting the appropriately substituted 4,6-dihydroxypyrimidine with a nitrating agent such as fuming nitric acid in acetic acid at a temperature from about 15° C. to about 40° C. for a period of about 1 to about 5 hours. The resulting 5-nitropyrimidines are converted to the 2,4-dichloro-5nitropyrimidine intermediates using a chlorinating agent such as phosphoryl chloride, alone or in the presence of a base, preferably diethylaniline, at a temperature from about 100° to about 115° C. for a period of about 0.5 to about 2 hours. Procedures for carrying out these transformations are described in *J. Chem. Soc.*, 3832 (1954).

The 2,6-bis(alkylthio)-5-nitropyrimidine derivatives may be prepared by reacting the appropriate dichloro intermediate with two equivalents of sodium alkylthiolate in a solvent such as dimethylformamide or, preferably, methanol, for about 4 to about 16 hours at a temperature from about 0° to about 30° C., preferably at ambient temperature. Monosubstitution of the dichloro intermediate is then accomplished by using one equivalent of nucleophile, at a reaction temperature of about 0° to about 100° C., depending on the reactivity of the nucleophile, in an inert solvent such as dimethyl-formamide or tetrahydrofuran, for a period of about 4 to about 16 hours.

The resulting monochloro derivative is then reacted with one equivalent of a different nucleophile to yield a disubstituted derivative with different substitutents on the carbon atoms at positions 2 and 4. The 2,6-disubstituted-5-nitropyrimidine is reduced using a reducing agent such as stannous chloride in concentrated hydrochloric acid or hydrogen gas with an appropriate catalyst, to yield the corresponding 5-aminopyrimidine derivative.

The novel pyridines of formula XXVIII and other 2,4-disubstituted-3-aminopyridine derivatives may be prepared by reacting the appropriate 2,4-dihydroxypyridine with a nitrating agent such as concentrated nitric acid at 80°–100° C. for 15–60 minutes. For example, the preparation of 2,4-dihydroxy-6-methyl-3-nitropyridine is described in *J. Heterocyclic Chem.*, 1970, 7, 389. The resulting 2,4-dihydroxy-3-nitro-pyridine is sequentially converted to the 2,4-dichloro-3-nitropyridine, 2,4-disubstituted-3-nitropyridine and 2,4-disubstituted-3-aminopyridine derivatives, using reaction conditions similar to those described above for the pyrimidine series.

The preparation of certain 5-aminoquinolines and 5-aminoisoquinolines used as reactants in scheme 1 is illustrated in scheme 5. Referring to scheme 5, 5-aminoquinolines and isoquinolines of the formulae XV and XVII may be prepared as follows. A quinoline or isoquinoline of the formula XIII is nitrated at the 5 position, respectively, by reacting it with a nitrating agent such as nitric acid or potassium nitrate with or without an acid catalyst such as sulfuric acid, for from about 2 to 16 hours at a temperature from about 0°–100° C. The nitro compound of formula XIV so formed is then reduced using a reducing agent such as stannous chloride, iron, zinc, or hydrogen gas with an appropriate catalyst, with or without an acid catalyst such as hydrochloric acid, for from about 2 to 16 hours at a temperature from about 0°–100° C., to yield the corresponding 5-aminoquinoline or 5-aminoisoquinoline of formula XV.

Compounds of the formula XVII, wherein $R^5$ is —$SR^{14}$ and is attached to the quinoline or isoquinoline ring at the 6 position, and wherein $R^{14}$ is ($C_1$–$C_6$) alkyl, ($C_5$–$C_7$) cycloalkyl, phenyl ($C_1$–$C_4$) alkyl, phenyl, substituted phenyl, heteroaryl, or substituted heteroaryl, may be prepared as follows. A compound of the formula XIV, wherein $R^5$ is —Cl and is attached to the quinoline or the isoquinoline ring at the 6 position, is reacted with a compound of the formula $R^{14}SH$, wherein $R^{14}$ is as defined above, and a base such as sodium hydride, or such compound of the formula XIV is reacted with a compound of the formula $R^{14}SNa$, wherein $R^{14}$ is as defined above, in an inert solvent such as tetrahydrofuran, for about 4 to 16 hours at a temperature of from about −10° C. to room temperature. The preferred temperature is −10° C. This reaction yields a compound of the formula XVI, which is then converted to the corresponding 5-aminoquinoline or isoquinoline of the formula XVII by the method described above for reduction of compounds of formula XIV.

An alternated and preferred method of making compounds of the formula I wherein Q is —$CR^2R^3R^4$, $R^2$ is hydrogen, $R^3$ is A, $R^4$ is alkylthio, phenylthio or heteroalkylthio, and $R^1$ is a group of the formulat XXIV or XXVII is described in Examples 261–263. Variations of this procedure are described in greater detail in The U.S. patent application of Kelly et al., assigned in common and filed concurrently with the present application.

The urea compounds of the formula I, wherein Q is —$NR^{17}R^{18}$, may be prepared by reacting a secondary amine of the formula $NHR^{17}R^{18}$ with a compound of the formula $R^1NCO$. The reaction is typically carried out at ambient temperature in a hydrocarbon solvent such as hexane. Secondary amines of the formula $NHR^{17}R^{18}$ may be prepared by a variety of methods well known in the art. (See, e.g., *Vogel's Textbook of Practical Organic Chemistry*, Longmen, Inc., New York, pp. 564–575 (4 ed. 1978).

Except where otherwise noted, pressure is not critical in any of the above reactions. Preferred temperatures for the above reactions were stated where known. In general, the preferred temperature for each reaction is the lowest temperature at which product will be formed. The preferred temperature for a particular reaction may be determined by monitoring the reaction using thin layer chromatography.

The novel compounds of formula I and the pharmaceutically acceptable salts thereof are useful as inhibitors of acyl coenzyme A: cholesterol acyltransferase (ACAT). As such they inhibit intestinal absorption of cholesterol in mammals and are useful in the treatment of high serum cholesterol in mammals, including humans. As used herein, treatment is meant to include both the prevention and alleviation of high serum cholesterol. The compound may be administered to a subject in need of treatment by a variety of conventional routes of administration, including orally, parenterally and topically. In general, these compounds will be administered orally or parenterally at dosages between about 0.5 and about 30 mg/kg body weight of the subject to be treated per day, preferably from about 0.08 to 5 mg/kg. For an adult human of approximately 70 kg of body weight, the usual dosage would, therefore, be about 3.5 to about 2000 mg per day. However, some variation in dosage will necessarily occur depending on the condition of the subject being treated and the activity of the compound being employed. The person responsible for administration will, in any event, determine the appropriate dose for the individual subject.

A compound of formula I or a pharmaceutically acceptable salt thereof may be administered alone or in combination with pharmaceutically acceptable carriers, in either single or multiple doses. Suitable pharmaceutical carriers include inert solid diluents or fillers, sterile aqueous solution and various organic solvents. The resulting pharmaceutical compositions are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of a compound of formula I or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. Such solutions are especially suitable for intravenous, intramuscular, subcutaneous and intraperitioneal administration. In this connection, the sterile aqueous media employed are all readily available by standard techniques known to those skilled in the art.

The activity of the compounds of the present invention as ACAT inhibitors may be determined by a number of standard biological or pharmacological tests. For example, the following procedure was used to determine the ACAT inhibiting activity of compounds of formula I. ACAT was assayed in microsomes isolated from chow fed Sprague-Dawley rats according to Bilheimer, J. T., Meth. Enzymol., 111, ps 286–293 (1985), with minor modifications. Microsomes from rat liver were prepared by differential centrifugation and washed with assay buffer prior to use. The assay mixture contained 25 ul of BSA (40 mg/ml), 30 ul of rat liver microsome solution (100 ug microsomal protein), 20 ul of assay buffer (0.1M $K_2PO_4$, 1.0 mM reduced Glutathione, pH 7.4), 20 ug of cholesterol in 100 ul of a 0.6% Triton WR-1339 solution in assay buffer, and 5 ul of test compound dissolved in 100% DMSO (total volume=180 ul). The assay mixture was incubated for 30 min at 37° C. The reaction was started by the addition of 20 ul of 14° C.-Oleoyl-CoA (1000 uM, 2,000 dpm/nmol) and run for 15 min at 37° C. The reaction was stopped by the addition of 1 ml ETOH. The lipids were extracted into 4 ml hexane. A 3 ml aliquot was dried under $N_2$, and resuspended in 100 ul of chloroform. 50 ul of chloroform were spotted on a heat activated TLC plate and developed in hexane: diethyl ether: acetic acid (85:15:1, v:v:v). Incorporation of radioactivity into cholesteryl esters was quantified on a Berthold LB2842 Linear TLC Analyzer. ACAT inhibition was calculated relative to a DMSO control assay.

The activity of the compounds of formula I in inhibiting intestinal absorbtion of cholesterol may be determined by the procedure of Melchoir and Harwell, *J. Lipid. Res.*, 26, 306–315 (1985).

The present invention is illustrated by the following examples. It will be understood, however, that the invention is not limited to the specific details of these examples. Melting points are uncorrected. Proton nuclear magnetic resonance spectra ($^1$H NMR) and $C^{13}$ nuclear magnetic resonance spectra ($C^{13}$ NMR) were measured for solutions in deuterochoroform (CDCl$_3$) and peak positions are expressed in parts per million (ppm) downfield from tetramethylsilane (TMS). The peak shapes are denoted as follows: s, singlet; d, doublet; t, triplet; q, quartet; m, multiplet; br, broad; c, complex.

EXAMPLE 1

Ethyl 2-(4-n-Propylphenylthio)nonanoate 1.6 g (0.033 mole) sodium hydride (50% dispersion in mineral oil) was added to a solution of 5.0 g (0.033 mole) 4-propylthiophenol in 25 ml anhydrous dimethylformamide. After 15 minutes, 8.8 g (0.033 mole) ethyl 2-bromononanoate (prepared according to *J. Labelled Compounds Radiopharm.* 14, 713 (1978)) was added and the resulting mixture was stirred at room temperature overnight. The reaction mixture was then diluted with 150 ml ethyl acetate and the resulting mixture was washed with 5×60 ml water and then with 60 ml saturated aqueous sodium chloride solution. The ethyl acetate solution was dried over anhydrous sodium sulfate, filtered and concentrated in vacuo. The resulting oil was chromatographed on 600 g silica gel, eluting with 7:3 hexane/methylene chloride to yield 9.0 g (81% yield) of the desired product as an oil.

$^1$H NMR(CDCl$_3$): 0.88δ(c,6H); 1.1–1.5 (c,total 12H) including 1.12 (t,3H); 1.54–1.93 (c,4H); 2.54 (t,2H); 3.56 (q, 1H); 4.07 (q, 2H); 7.1 (d, 2H); 7.36 (d, 2H).

EXAMPLE 1A

2-Hexythiodecanoic Acid 17.3 g (0.36 mol) sodium hydride (50% dispersion in mineral oil) was added portionwise with stirring (gas evolution) to a solution of 26.8 ml. (0.19 mol) hexanethiol in 500 ml. anhydrous dimethylformamide. The mixture was stirred at room temperature for 30 min., then 45.2 g (0.18 mol) 2-bromodecanoic acid was added dropwise with stirring, keeping the temperature of the reaction mixture below 45° C. The reaction mixture was stirred at room temperature under nitrogen overnight. The mixture was then diluted with 500 ml. water and the pH of the resulting mixture was adjusted to 1.5 with 6N aqueous hydrochloric acid solution. This mixture was extracted with 3×400 ml. ethyl acetate and the combined ethyl acetate extracts were washed with 5×700 ml. water and 1×500 ml. brine. The ethyl acetate solution was dried over anhydrous sodium sulfate, filtered and concentrated in vacuo. The resulting oil was chromatographed on 2 kg. silica gel, eluting with methylene chloride to yield 35 g (67% yield) of the desired product as an oil.

EXAMPLE 1B

Resolution of 2-hexylthiodecanoic acid

2-Hexylthiodecanoyl chloride was prepared by the procedure of Example 4A. A solution of 2-hexylthiodecanoyl chloride (2.39 g., 7.8 mmol) in 20 ml methylene chloride was added slowly with stirring under nitrogen to a solution of (R)-(−)-2-phenylglycinol (1.08 g, 7.9 mmol) and 4-dimethylaminopyridine (0.96 g, 7.9 mmol) in 80 ml methylene chloride at 5° C. The reaction mixture was stirred at room temperature overnight. Methylene chloride (100 ml.) was then added and the resulting solution was washed sequentially with 100 ml 1N aqueous hydrochloric acid solution, 100 ml water, 100 ml saturated aqueous sodium bicarbonate solution and 100 ml brine. The organic phase was dried over anhydrous sodium sulfate and concentrated in vacuo to a solid residue (3.1 g). The diastereomers were separated by column chromatography on 800 g silica gel using 1:1 hexane-diethyl ether as eluant. The less polar diastereomer (1.09 g, $[\alpha]_D^{RT}=-9.85$ (CH$_3$OH); mp 98°–100° C.) and 0.99 g of the more polar diastereomer ($[\alpha]_D^{RT}=-9.46$ (CH$_3$OH) mp 105°–108° C.) were obtained along with 0.36 g of a mixture of diastereomers (total yield 76%). A solution of the less polar diastereomer (900 mg, 2.2 mmol) in 42 ml 1,4-dioxane and 42 ml 6N aqueous sulfuric acid solution was heated at 105° C. under nitrogen for 15 hours. The reaction mixture was cooled to room temperature, diluted with 80 ml water and the resulting mixture was extracted with 4×60 ml ethyl acetate. The combined ethyl acetate extracts were washed with 60 ml brine, dried over anhydrous sodium sulfate and concentrated in vacuo to yield (S)-(−)-2-hexylthiodecanoic acid as an oil (634 mg., 99.6% yield); $[\alpha]_D^{RT}=-59.5$ (CH$_3$OH).

In a similar manner, hydrolysis of the more polar diastereomer yielded 98.4% of (R)-(+)-2-hexylthiodecanoic acid as an oil; $[\alpha]_D^{RT}=+54.0$(CH$_3$OH).

EXAMPLE 2

Ethyl 2-(4-t-Butylphenylthio)octanoate

A mixture of 5.0 g (0.02 mole) ethyl 2-bromooctanoate, 3.37 g (0.02 mole) p-t-butylthiophenol and 3.31 g (0.24 mole) potassium carbonate in 70 ml acetone was refluxed under nitrogen overnight. The reaction mixture was cooled to room temperature and filtered and the filtrate was concentrated in vacuo. The residue was chromatographed on 500 g silica gel, eluting with 6:4 methylene chloride/hexane to yield 3.8 g (57% yield) of the desired product as an oil.

$^1$H NMR(CDCl$_3$): δ0.88 (c,3H); 1.1–1.52 (c,total 20H) including 1.14 (t,3H) and 1.3 (s); 1.66–2.11 (c,2H); 358 (q,1H); 4.1 (q,2H); 7.36 (m,4H).

EXAMPLE 3

2-(4-n-Propylphenylthio)nonanoic acid

A solution containing 5.7 (0.017 mole) of the title compound of Example 1, 35 ml of 1N aqueous sodium hydroxide solution (0.035 mole) and 3 ml methanol was refluxed overnight. The resulting solution was cooled to room temperature, acidified to pH 1.5 with 2N aqueous hydrochloric acid and extracted with 3×50 ml ethyl acetate. The combined ethyl acetate extracts were washed with 50 ml water and 50 ml saturated aqueous sodium chloride solution, dried over anhydrous sodium sulfate and concentrated in vacuo to yield the title compound as an oil (5.0 g, 96% yield) which was used in the subsequent reaction without further purification.

$^1$H NMR(CDCl$_2$): δ0.88 (c, 6H); 1.17–1.54 (c, 12H); 1.54–1.92 (c, 4H); 2.53 (t, 2H); 3.54 (t, 1H); 7.1 (d, 2H); 7.37 (d, 2H).

EXAMPLE 4

2-(4-n-propylphenylthio)-N-(2,4,6-trimethoxyphenyl)nonanamide 1.54 g (5 mmole) of the title compound of Example 3 in 20 ml of thionyl chloride was refluxed for 3 hours and then concentrated to dryness in vacuo. 523 mg (1.6 mmole) of the resulting acid chloride was dissolved in 20 ml methylene chloride and to the solution was added 292 mg (1.6. mmole) 2,4,6-trimethoxyaniline and 195 mg (1.6 mmole) 4-dimethylaminopyridine. The resulting solution was stirred at room temperature overnight and then concentrated in vacuo. The residue was partitioned between 60 ml ethyl acetate and 20 ml 1N aqueous hydrochloric acid solution. The ethyl acetate layer was washed with 50 ml water and 50 ml saturated aqueous sodium chloride solution, dried over anhydrous sodium sulfate and concentrated in vacuo. The crude product was chromatographed on 100 g silica gel, eluting with 1:1 hexane/ethyl acetate to yield 370 mg (49% yield) of the title compound as a whitish solid.

EXAMPLE 4A

N-[2-methyl-4,6-bis(methylthio) pyrimidin-5-yl]-2-hexylthiodecanoic amide

A solution of 6.49 g (22.5 mmol) 2-hexylthiodecanoic acid in 40 ml thionyl chloride and 100 ml benzene was refluxed under nitrogen for 2.5 hours and then concentrated to dryness in vacuo. The resulting acid chloride (6.88 g, 2.5 mmol) was dissolved in 15 ml. methylene chloride and the solution was added dropwise to a solution of 4.63 g (23 mmol) 5-amino4,6-bis(methylthio)-2-methylpyrimidine in 140 ml methylene chloride. The resulting solution was refluxed under nitrogen overnight. The reaction solution was then cooled, diluted with 140 ml methylene chloride and washed with 2×125 ml 3N aqueous hydrochloric acid solution, 1×125 ml water, 1×125 ml saturated aqueous sodium bicarbonate solution and 1×125 ml brine. The methylene chloride solution was dried over anhydrous sodium sulfate, filtered and concentrated to dryness in vacuo. The solid residue was recrystallized from diethyl ether yielding 5.35 g of the title compound, m.p. 99°–101° C. The filtrate was concentrated in vacuo and the residue was chromatographed on 400 g silica gel eluting with 9:1 hexane/ethyl acetate. Recrystallization of the product obtained by chromatography from diethyl ether yielded another 2.32 g of the title compound, m.p. 99°–101° C. (total yield 72.4%).

$^1$H NMR (CDCl$_3$): δ0.87 (c, 6H); 1.21–1.84 (c, 21 H), 2.02 (m, 1H); 2.50 (s, 6H); 2.76 (s, 3H), 2.74 (t, 2H); 3.45 (t, 1H), 8.08 (s, 1H);

IR (CHCl$_3$): 2923, 2852, 1681, 1511, 1468, 1431, 1405 cm$^{-1}$.

EXAMPLE 4B

N-[2,4-bis(methylthio)-6-methylpyridin-3-yl]-2-hexylthiode canoic amide

A solution of 4.19 g (13.7 mmol) 2-hexylthiodecanoyl chloride, prepared according to Example 4A, in 15 ml methylene chloride was added dropwise with stirring under nitrogen to a solution of 2.75 g (13.7 mmol) 3-amino-2,4-bis(methylthio)-6-methylpyridine in 30 ml pyridine cooled to 5° C. The reaction mixture was stirred at room temperature under nitrogen overnight. Methylene chloride (250 ml) was then added to the reaction mixture and the resulting solution was washed with 3×50 ml 3N aqueous hydrochloric acid solution, 2×50 ml water, 1×50 ml saturated aqueous sodium bicarbonate solution and 1×50 ml brine. The methylene chloride solution was dried over anhydrous sodium sulfate, filtered and concentrated to dryness in vacuo. The solid residue (6.5 g) was recrystallized from petroleum ether to yield 4.7 g of the title compound, m.p. 75°–76.5° C. (72.8% yield).

$^1$H NMR (CDCl$_3$): δ0.86 (c, 6H); 1.16–1.74 (c, 21H); 2.04 (m, 1H); 2.4 (s, 3H); 2.48 (s, 3H); 2.5 (s, 3H); 2.77 (t, 2H); 3.45 (t, 1H); 6.65 (s, 1H); 8.14 (s, 1H).

IR (CHCl$_3$): 2922, 2852, 1676, 1600, 1561, 1466 cm$^{-1}$.

EXAMPLE 5

2-Bromo-N-(2,4,6-trimethoxyphenyl)decanamide

2-Bromodecanoic acid (1 g, 3.8 mmol) was heated under reflux in thionyl chloride (10 ml) for 1 hour. The thionyl chloride was evaporated and the residue was dissolved in dry ether (10 ml) and added dropwise to a solution of 2,4,6-trimethoxyaniline (0.7 g, 3.8 mmol) in pyridine (20 ml) at 0° C. and the mixture was stirred for 1.5 hours. The reaction mixture was poured into saturated aqueous ammonium chloride and extracted three times with ethyl acetate (60 ml). The combined organics were extracted with water and brine and dried and concentrated. Recrystallization from isopropyl ether afforded 1.1 g (65%) of the title compound, m.p. 109°–110° C. This material was used directly in the next step.

EXAMPLE 6

N-(2,4,6-Trimethoxy)phenyl-2-((2-pyridyl)thio)decanoamide

2-Thiopyridine (0.27 g, 2.4 mmol) in dimethylformamide (20 ml) was treated with sodium hydride (0.1 g, 2.4 mmol, 60% oil dispersion) and stirred for 15 minutes at 25° C. To this cloudy solution, the title compound of Example 5 (1.0 g, 2.4 mmol) in dimethylformamide (10 ml) was added and the mixture was stirred at 25° C. for 1.5 hours. The reaction mixture was then poured into 1N HCl (75 ml) and extracted 3 times with ethyl acetate (125 ml). The organics were dried, concentrated and chromatographed on silica gel (eluted with 1:1 ethyl acetate:hexanes). Recrystallization from isopropyl ethyl afforded 0.4 g (36%) of the title compound, m. p. 92° C.

$^1$H NMR (CDCl$_3$): δ8.52–8.42 (m, 2H), 7.54 (t, J=4 Hz, 1H), 7.26 (m, 1H), 7.04 (t, J=4 Hz, 1H), 6.12 (s, 2H), 4.53 (t, J=3 Hz, 1H), 3.80 (s, 3H), 3.66 (s, 6H), 2.26–0.86 (m, 17H). IR (CHCl$_3$): 2920, 1685, 1595 cm$^{-1}$. Anal. Calculated for C$_{24}$H$_{34}$O$_4$N$_2$S: C, 64.55; H, 7.67; N, 6.27. Found: C, 64.34; H, 7.54; N, 6.20.

The title compounds of Examples 7 through 12 were prepared by a procedure similar to that described in Example 4.

EXAMPLE 7

2-(4-t-Butylphenylthio)-N-(2,4,6-trimethoxyphenyl) nonanamide (57% yield)

$^1$H NMR: δ0.87 (c, 3H); 1.28 (s, 9H); 1.3 (c, 8H); 1.57 (c, 2H); 2.0 (c, 2H); 3.70 (s, 6H); 3.78 (s+c, 4H); 6.11 (s, 2H); 7.29 (d, 2H); 7.42 (d, 2H); 7.87 (s, 1H). IR (CHCl$_3$): 1672 cm$^{-1}$.

EXAMPLE 8

2-[4-(1,1-Dimethylpropyl)phenylthio]-N-(2,4,6-trimethoxyphenyl)nonanamide (60% yield)

$^1$H NMR: δ0.65 (m, 3H); 0.87 (c, 3H); 1.24 (s, 6H); 1.28 (c, 8H); 1.62 (c, 4H); 1.97 (c, 2H); 3.71 (s, 6H); 3.75 (m, 1H); 3.78 (s, 3H); 6.12 (s, 2H); 7.22 (d, 2H); 7.41 (d, 2H); 7.89 (s, 1H). IR(CHCl$_3$): 1670 cm$^{-1}$.

EXAMPLE 9

2-(4-n-Butylphenylthio)-N-(2,4,6-trimethoxyphenyl)-nonanamide (22% yield)

$^1$H NMR: δ0.89 (m, 6H); 1.32 (c, 10H); 1.58 (c, 4H); 1.97 (c, 2H); 2.55 (m, 2H); 3.71 (s, 6H); 3.75 (m, 1H); 3.78 (s, 3H); 6.11 (s, 2H); 7.08 (d, 2H); 7.41 (d, 2H); 7.86 (s, 1H). IR (CHCl$_3$): 1670 cm$^{-1}$.

EXAMPLE 10

2-[4-(1-Methylpropyl)phenoxy]-N-(2,4,6-trimethoxyphenyl)nonanamide (50% yield)

$^1$H NMR: δ0.87 (c, 6H); 1.2 (d, 3H); 1.3 (c, 8H); 1.55 (m, 4H); 2.0 (m, 2H); 2.55 (m, 1H); 3.70 (s, 6H); 3.77 (s, 3H); 4.6 (t, 1H); 6.1 (s, 2H); 6.96 (d, 2H); 7.09 (d, 2H); 7.38 (S, 1H). IR (CHCl$_3$) 1680 cm$^{-1}$.

EXAMPLE 11

2-(4-n-Propylphenoxy)-N-(2,4,6-trimethoxyphenyl)-decanamide (59% yield)

$^1$H NMR: δ0.88 (c, 6H); 1.28 (c, 10H); 1.6 (c, 4H); 2.0 (m, 2H); 2.52 (t, 2H); 3.71 (s, 6H); 3.77 (s, 3H); 4.59 (t, 1H); 6.1 (s, 2H); 6.95 (d, 2H); 7.1 (d, 2H); 7.37 (s, 1H). IR (CHCl$_3$): 1683 cm$^1$.

EXAMPLE 12

2-(4-n-Propylphenylthio)-N-(2,4,6-trimethoxyphenyl)non-anamide (49% yield)

$^1$H NMR: δ0.89 (m, 6H); 1.3 (c, 8H); 1.59 (m, 4H); 1.95 (c, 2H); 2.53 (t, 2H); 3.71 (s, 6H); 3.75 (m, 1H); 3.78 (s, 3H); 6.11 (s, 2H); 7.09 (d, 2H); 7.41 (d, 2H); 7.86 (s, 1H). IR (CHCl$_3$): 1670 cm$^{-1}$.

The title compounds of Examples 13 through 24 were prepared by a procedure similar to that described in Examples 5 and 6.

EXAMPLE 13

N-(2,4,6-Trimethyl)phenyl-2-(1-decylthio)octanamide

M.p. 42° C. $^1$H NMR: δ8.06 (s, 1); 6.85 (s, 2); 3.39 (t, 3 Hz, 1); 2.61 (t, 4 Hz, 2); 2.23 (s, 3); 2.16 (s, 6); 1.58 (m, 4); 1.23 (bs, 22); 0.84 (t, 4 Hz, 6). IR (CHCl$_3$) 3340, 2930, 1675, 1500 cm$^{-1}$.

EXAMPLE 14

N-(2,4,6-Trimethyl)phenyl-2-((pyrid-2-yl)thio)decanamide

M.p. 85°–87° C. $^1$H NMR: δ8.81 (s, 1); 8.36 (d, 2 Hz, 1); 7.50 (t, 3 Hz, 1); 7.24 (d, 3 Hz, 1); 7.01 (t, 3 Hz, 1); 6.80 (s, 2); 4.48 (t, 3 Hz, 1); 2.21 (s, 3); 2.0 (s, 6); 1.85–0.80 (m, 17). IR (CHCl$_3$) 2930, 1685, 1585 cm$^{-1}$.

EXAMPLE 15

N-(2,4,6-Trimethyl)phenyl-2-((2-methylfuryl)thio)decanoamide

M.p. 64°–65° C. $^1$NMR: δ7.92 (bs, 1); 7.34 (s, 1); 6.88 (s, 2); 6.28 (m, 1); 6.21 (d, 1 Hz, 1); 3.88 (s, 2); 3.42 (t, 3 Hz, 1); 2.26 (s, 3); 2.18 (S, 6); 2.04–0.82 (m, 17). IR (CHCl$_3$): 2930, 1675, 1495 cm$^{-1}$.

EXAMPLE 16

N-(2,4,6-Trimethyl)phenyl-2-[(2(6-ethoxybenzothiazoyl)thio]octanamide

M.p. 106°–108° C. $^1$H NMR: δ7.90 (s, 1); 7.60 (s, 1); 6.86 (s, 2); 4.83 (t, 3 Hz, 1); 4.48 (t, 3 Hz, 1); 3.32 (q, 4 Hz, 2); 2.37 (s, 3); 2.12 (s, 6) 2.0–0.85 (m, 26). IR (CHCl$_3$): 2920, 1680, 1595 cm$^{-1}$.

EXAMPLE 17

N-(2,4,6-Trimethyl)phenyl-2-[4-(7-trifluoromethylquinolinyl)thio]decanamide

M.p. 195°–196° C. $^1$H NMR: δ8.77 (d, 3 Hz, 1); 8.42 (s, 1); 8.27 (d, 5 Hz, 1); 7.84 (s, 1); 7.77 (d, 5 Hz, 1); 8.54 (d, 3 Hz, 1); 6.80 (s, 2); 4.26 (t, 3 Hz, 1); 2.22 (s, 3); 1.91 (s, 6); 2.20–0.80 (m, 17). IR (CHCl$_3$): 29,20, 1680, 1495 cm$^{-1}$.

EXAMPLE 18

N-(2,4,6-Trimethyl)phenyl-2-((2-thiazolyl)thio)decanamide

M.p. 74°–75° C. $^1$H NMR: δ8.82 (bs, 1); 7.25 (d, 1 Hz, 1); 6.84 (s, 2); 4.41 (t, 3 Hz, 1); 2.24 (s, 3); 2.05 (s, 6); 1.96–0.84 (m, 17). IR (CHCl$_3$: 2920, 1850, 1685, 1490 cm$^{-1}$.

EXAMPLE 19

N-(2,4,6-Trimethyl)phenyl-2-((2-quinolinyl)thio)decanamide

M.p. 11°–112° C. $^1$H NMR: δ9.14 (bs, 1); 7.98 (d, 4 Hz, 1); 7.89 (d, 3 Hz, 1); 7.77 (d, 3 Hz, 1); 7.65 (t, 3 Hz, 1); 7.47 (t, 3 Hz, 1); 7.31 (d, 4 Hz, 1); 6.82 (s, 2); 4.82 (t, 3 Hz, 1) 2.38–0.85 (m, 28). IR (CHCl$_3$): 2920, 2850, 1680, 1590 cm$^{-1}$.

EXAMPLE 20

N-(2,4,6-Trimethoxy)phenyl-2-(1-hexylthio)octanamide

M.p. 56°–58° C. $^1$NMR: δ7.79 (s, 1); 6.12 (s, 2); 3.78 (s, 3); 3.76 (s, 76 (s, 6); 3.44 (t, 4 Hz, 1); 2.66 (m, 2); 1.90–0.87 (m, 24). IR (CHCl$_3$): 2930, 1675, 1490 cm$^{-1}$.

EXAMPLE 21

N-(2,4,6-Trimethoxy)phenyl-2-(1-decylthio)octanamide

M.p. 54°–56° C. $^1$NMR: δ (CDCl$_3$) 7.81 (s, 1); 6.15 (s, 2); 3.81 (s, 3); 3.79 (s, 6); 3.47 (t, 4 Hz, 1) 2.69 (m, 4); 1.63–1.92 (m, 6); 1.60 (m, 20); 0.90 (m, 6). IR (CHCl$_3$) 2920, 1670, 1600, 1460 cm$^{-1}$.

EXAMPLE 22

N-(2,4,6-Trimethyl)phenyl-1-(iso-butylthio)octanamide

M.p. 58°–60° C. $^1$H NMR: δ8.03 (s, 1); 6.85 (s, 2) 3.37 (t, 4 Hz, 1); 2.52 (m, 2); 2.17 (s, 6); 1.83–0.86 (m, 16). IR (CHCl$_3$): 2930, 1670, 1495 cm$^{-1}$.

EXAMPLE 23

N-(2,4,6-Trimethyl)phenyl-2-[2-(3-propyloxypyridyl) thio]decanamide

M.p. 68°–69° C. $^1$H NMR: δ8.74 (bs, 1); 8.02 (m, 1); 7.02 (d, 1 Hz, 2); 6.82 (s, 2); 4.56 (t, 3 Hz, 1); 4.03 (t, 3 Hz, 2);

2.25 (s, 3); 2.02 (s, 6); 1.94–0.82 (m, 22). IR (CHCl$_3$): 2910, 2840, 1680, 1490 cm$^{-1}$.

EXAMPLE 24

N-(Isoquinolin-5-yl)-2-((2-pyridyl)thio) decanamide

M.p. 81°–83° C. $^1$H NMR: δ9.24 (bs, 1); 8.60–8.36 (m, 3); 7.78–7.11 (m, 7); 4.53 (t, 3 Hz, 1); (CHCl$_3$): 2940, 2860, 1700, 1590 cm$^{-1}$.

EXAMPLE 25

N-(2,4,6-Trimethoxyphenyl)-2-methyl-2-(4-(1-methylpropyl)phenoxy)nonanoic amide

By use of the procedures described in Examples 1 and 3, ethyl 2-bromononanoate and 4-(1-methylpropyl)phenol were coupled and the product saponified to give 2-(4-(1-methylpropyl)phenoxy) nonanoic acid. This material (1.0 g) was then methylated at the 2-position according to the procedure of Pfeffer, et. al. (J. Org. Chem., 1972, 37, 451) to give 2-methyl-2-hexanethiodecanoic acid (0.928 g). This material (0.86 g) was converted to the corresponding acid chloride with oxalyl chloride and coupled with 2,4,6-trimethoxyaniline (0.49 g) according to the procedure of Adams and Ulrich (J. Am. Chem. Soc., 1920, 42, 599) to give the title compound (1.12 g).

Oil. $^1$H NMR: δ7.82 (s, 1H); 7.12 (d, 6 Hz, 2 H); 7.07 (d, 6 Hz, 2 H); 6.19 (s, 2 H); 3.85 (s, 3 H); 3.83 (s, 6 H); 2.61 (dt, 8 Hz, 1 H); 1.98 (m, 2 H); 1.68–1.20 (m, 12 H); 1.52 (s, 3 H); 1.26 (d, 8 Hz, 3 H); 0.93 (m, 3 H); 0.85 (t, 8 Hz, 3 H) . $^{13}$C NMR: δ173.38, 159.90, 156.48, 152.69, 142.12, 127.39, 121.24, 107.15, 91.02, 84.41, 55.83, 55.47, 40.94, 40.06, 31.86, 31.32, 29.85, 29.33, 23.46, 22.68, 21.90, 21.67, 14.11, 12.21. IR (CHCl$_3$) cm$^{-1}$: 3410, 2940, 2850, 1680, 1608. Mass spectrum m/e (relative intensity): M+ 485.42 (16), 336.28 (33), 308.28 (24), 275.30 (30), 209.04 (40), 183.14 (100). High resolution mass spectra: m.e 485.3134, calcd for C$_{29}$H$_{43}$NO$_5$: 485.3141. Anal.: Calc'd for C$_{29}$H$_{43}$NO$_5$: C, 71.72; H, 8.93; N, 2.88. Found: C, 71.28; H, 8.87; N, 2.74.

EXAMPLE 26

N-(Isoquinolin-5-yl)-2-(4-(1-methylpropyl)phenoxy) nonanoic amide

N-(isoquinolin-5-yl)-2-bromodecanoic amide, prepared according to the procedures described in Example 3 and 25, was coupled with 4-(1-methylpropyl)phenol according to the procedure described in Example 6 to give the title compound.

Oil. $^1$H NMR: δ9.23 (s, 1H); 8.61 (s, 1H); 8.40 (d, 6 Hz, 1H); 8.25 (d, 6 Hz, 1H); 7.80 (d, 9 Hz, 1H) 7.62 (dd, 6 and 9 Hz, 1H); 7.19 (d, 8 Hz, 2H); 7.00 (d, 8 Hz, 2H); 6.80 (d, 9 Hz, 1H); 4.78 (t, 6 Hz, 1H); 2.58 (tq, 6 & 9 Hz, 1H); 2.12 (m, 2H); 1.60 (m, 4H); 1.25 (m, 11H); 0.86 (t, 9 Hz, 3H); 0.85 (t, 8 Hz, 3H); $^{13}$C NMR: δ170.91, 155.34, 154.48, 152.94, 143.20, 142.07, 130.83, 129.60, 129.02, 128.58, 128.01, 127.40, 125.17, 124.26, 115.25, 113.49, 79.49, 40.94, 33.36, 31.80, 31.30, 29.35, 29.16, 25.26, 22.67, 22.08, 14.13, 12.20.

IR (CHCl$_3$) cm$^{-1}$: 3670, 3404, 2951, 2924, 1690, 1608, 1591. Mass spectrum m/e (relative intensity): M+432.2 (16), 403.2 (7), 284.2 (30), 255.2 (36), 171.1 (25), 144.1 (100). Anal.: Calc'd for C$_{28}$H$_{36}$N$_2$O$_2$: C, 77.74; H, 8.39; N, 6.48. Found: C, 76.12; H, 8.57; N, 5.03.

EXAMPLE 27

N-(Isoquinolin-5-yl)-2-(4-propylphenoxy)decanoic amide

N-(isoquinolin-5-yl)-2-bromodecanoic amide, prepared according to the procedures described in Examples 3 and 25, was coupled with 4-propylphenol according to the procedure described in Example 6 to give the title compound.

Oil. $^1$H NMR: δ9.24 (s, 1H); 8.63 (s, 1H); 8.41 (d, 5 Hz, 1H); 8.24 (d, 7 Hz, 1H); 7.80 (d, 8 Hz, 1H); 7.60 (dd, 6 & 6 Hz, 1H); 7.21 (d, 5 Hz, 1H); 7.15 (d, 6 Hz, 2 H); 6.99 (d, 6 Hz, 2H); 4.76 (t, 5 Hz, 1H); 2.55 (t, 6 Hz, 2H); 2.10 (m, 2H); 1.62 (m, 4H); 1.45–1.18 (br. m, 10H); 0.94 (t, 5 Hz, 3H) ; 0.85 (t, 4 Hz, 3H). $^{13}$C NMR: δ170.77, 155.29, 153.01, 143.39, 136.99, 130.80, 129.94, 129.70, 129.00, 127.26, 125.02, 123.96, 115.24, 113.27, 79.54, 37.12, 33.28, 31.82, 29.38, 29.33, 29.19, 25.17, 24.70, 22.64, 14.08, 13.73. IR (CHCl$_3$) cm$^{-1}$: 3397, 2922, 1691, 1590. Mass spectrum m/e (relative intensity): M+432.30 (4), 298.16 (24), 269.20 (36), 171.06 (22), 144.06 (100). Anal: Calc'd for C$_{28}$H$_{36}$N$_2$O$_2$: C, 77.74; H, 8.39; N, 6.48. Found: C, 77.63; H, 8.43; N, 6.22.

EXAMPLE 28

N-(Isoquinolin-5-yl)-N'-(4-(3-methylbutyl) phenylmethyl)-N'-heptylurea

N-(4 -(3-methylbutyl)phenyl) methyl-N-heptylamine was prepared and coupled with commercially available 5-aminoisoquinoline according to the procedure of DeVries, et. al. (*J. Med. Chem.*, 29, 1131 (1986)) to give the title compound.

Oil. $^1$H NMR: δ9.15 (s, 1H) ; 8.24 (d, 6 Hz, 1H); 8.05 (d, 8 Hz, 1H); 7.65 (d, 8 Hz, 1H); 7.50 (dd, 8 & 8 Hz, 1H); 7.32 (d, 8 Hz, 2H); 7.28 (d, 8 Hz, 2H); 6.67 (s, 1H); 6.62 (d, 6 Hz, 1H); 4.64 (s, 2H); 3.52 (t, 6 Hz, 2H); 2.70 (t, 6 Hz, 2H); 1.75 (m, 2H); 1.67–1.20 (m, 11H); 0.95 (d, 6 Hz, 6H); 0.88 (t, 6 Hz, 3H). $^{13}$C NMR: δ155.72, 153.01, 143.51, 142.73, 134.38, 133.42, 129.46, 129.35, 129.07, 127.40, 126.91, 123.20, 123.02, 113.44, 51.34, 49.14, 41.03, 33.51, 31.87, 29.18, 28.79, 27.79, 27.08, 22.66, 22.59, 14.14. IR (CHCl$_3$) cm$^{-1}$: 3414, 2921, 2854, 1662, 1591, 1507. Mass spectrum m/e (relative intensity): M+445.3 (6), 304.0 (7), 274.2 (2), 190.1 (20), 170.0 (32), 161.2 (100). High resolution mass spectra: m/e 445.3076, calc'd for C$_{29}$H$_{39}$N$_3$O: 445.3093. Anal.: Calc'd for C$_{29}$H$_{39}$N$_3$O: C, 78.12; H, 8.82; N, 9.43. Found: C, 75.42; H, 8.59; N, 8.85.

EXAMPLE 29

N-(Isoquinolin-5-yl)-2-(methoxycarbonylmethyl) nonadecanoic amide

Commercially available N-(isoquinolin-5-yl)-2-(carboxymethyl) nonadecanoic amide was esterified with diazomethane in ether to give the title compound.

$^1$H NMR: δ9.16 (s, 1H); 8.57 (s, 1H) ; 8.48 (d, 6 Hz, 1H); 8.08 (d, 6 Hz, 1H); 7.70 (d, 8 Hz, 1H); 7.66 (d, 8 Hz, 1H); 7.50 (dd, 6 and 8 Hz, 1H) ; 5.50 (m, 1H) ; 5.32 (m, 1 H); 3.70 (s, 3H); 3.18–2.80 (m, 2H); 2.70–2.20 (m, 3H); 1.95 (m, 2H) ; 1.20 (m, 22H); 0.85 (t, 6 Hz, 3H) ; $^{13}$C NMR: δ175.77, 170.66, 152.56, 142.68, 134.59, 134.39, 131.97, 128.87, 127.84, 125.35, 124.78, 114.77, 114.60, 51/93, 43.32, 41.85, 38.03, 35.28, 32.62, 32.54, 31.90, 29.68, 29.51, 29.43, 29.34, 29.19, 22.67, 14.11.

IR (KBr) cm$^{-1}$: 3418, 2918, 2848, 1724, 1692, 1591. Mass spectrum m/e (relative intensity): M+466.7 (1), 305.3 (2), 259.2 (11), 226.1 (76), 186.1 (88), 171.0 (32) 144.0 (100). Anal.: Calc'd for C$_{29}$H$_{42}$NO$_3$: C, 74.96; H, 9.23; N, 5.83. Found: C, 74.88; H, 9.27; N, 5.78.

EXAMPLE 30

N-(Isoquinolin-5-yl)-2-(decyl)cyclopentane carboxamide 2-(Decyl) cyclopentane carboxylic acid, prepared according to the procedure of Hoefle, et. al. (U.S. Pat. No.

4,715,175), was coupled with 5-aminoisoquinoline according to the procedure outlined in Example 47 to give the title compound.

$^1$H NMR: δ9.22 (s, 1H); 8.51 (d, 5 Hz, 1H); 8.10 (d, 7 Hz, 1H); 7.78 (d, 7 Hz, 1H); 7.75 (s, 1 Hz, H); 7.59 (d, 7 Hz, 1H); 7.52 (dd, 5 & 7 Hz, 1H); 2.26 (m, 2H); 1.75 (m, 8H); 1.23 (m, 16H); 0.86 (t, Hz, 3H) . $^{13}$C NMR: δ176.32, 153.13, 143.25, 131.98, 129.83, 129.04 127.304, 124.70, 124.49 113.60, 55.70, 40.40, 36.23, 31.87, 30.18, 29.58, 29.49, 20.30, 25.93, 24.74, 22.66, 14.09.

IR (KBr) cm$^{-1}$: 3432, 2923, 2851, 1686, 1591, 1506. Mass spectrum m/e (relative intensity): M+381.28 (62), 240.08 (34), 209.20 (94), 144.08 (100). Anal. Calc'd for $C_{25}H_{36}N_2O$: C, 78.90; H, 9.54; N, 7.36. Found: C, 78.53; H, 9.58; N, 7.27.

EXAMPLE 31

N-(3-Methylquinolin-5-yl)-2-(4-(1-methylpropylphenoxy)nonanoic amide

3-Methyl-4-chloro-5-nitroquinoline was hydrogenated using Pd/C to give 3-methyl-5-aminoquinoline. This material was coupled with 2-(4-(1-methylpropyl)phenoxy) nonanoic acid according to the procedure outlined in Example 25 to give the title compound.

Oil. $^1$H NMR: δ8.70 (s, 1H); 8.48 (s, 1H); 7.93 (d, 9 Hz, 1H); 7.88 (d, 9 Hz, 1H); 7.64 (dd, 9 and 9 Hz, 1H); 7.52 (s, 1H); 7.18 (d, 9 Hz, 2H); 7.01 (d, 9 Hz, 2H); 4.78 (dd, 6 & 8 Hz, 1H); 2.61 (tq, 9 and 9 Hz, 1H); 2.40 (s, 3H); 2.11 (m, 2H); 1.72–1.26 (m, 12H); 1.24 (d, 7 Hz, 3H); 0.90 (m, 3H); 0.84 (t, 10 Hz, 3H) . $^{13}$C NMR: δ170.85, 155.39, 152.24, 147.70, 141.84, 130.65, 128.50, 128.17, 128.07, 127.21, 122.40, 121.62, 115.08, 79.43, 40.84, 33.39, 31.75, 31.31, 31.24, 29.32, 29.13, 25.31, 22.62, 21.91, 18.87, 14.06, 12.20. Mass spectrum m/e (relative intensity): M+446.32 (11), 297.22 (59), 269.22 (85), 185.05 (44), 158.08 (100). High resolution mass spectra: m/e 446.2938, calc'd for $C_{29}H_{38}N_2O_2$: 446.2928. Anal.: Calc'd for $C_{29}H_{38}N_2O_2$: C, 77.99; H, 8.58; N, 6.27. Found: C, 75.94; H, 8.40; N, 6.65.

EXAMPLE 32

N-(2-Methyl-6-fluoroquinolin-5-yl)-2-(hexylthio) decanoic amide

2-Methyl-5-amino-6-fluoroquinoline, prepared by reduction of the corresponding nitro compound according to Example 31, was coupled with 2-hexylthiodecanoic acid according to the procedure of Example 25 to give the title compound.

$^1$H NMR: δ8.52 (s, 1H); 7.95 (d, 10 Hz, 1H); 7.91 (m, 1H); 7.46 (dd, 10 & 12 Hz, 1H); 7.27 (d, 10 Hz, 1H); 3.50 (t, 8 Hz, 1H); 2.70 (s, 3H); 2.68 (t, 7 Hz, 1H); 2.10 (m, 1H); 1.82 (m, 1H); 1.70–1.16 (m, 20H); 0.82 (t, 7 Hz, 6 H). $^{13}$C NMR: δ172.10, 158.50, 131.60, 129.80, 122.72, 119.40, 119.20, 51.22, 33.07, 32.10, 31.82, 31.33, 29.36, 29.26, 29.19, 28.59, 27.55, 25.10, 22.64, 22.49, 14.07, 13.97. IR (KBr) cm$^{-1}$: 3243, 2928, 2862, 1656. Mass spectrum m/e (relative intensity): M+446.34 (1), 243.20 (8), 231.14 (9), 218.10 (6), 176.14 (100) . Anal.: Calc'd for $C_{26}H_{39}FN_2OS$: C, 69.91; H, 8.80; N, 6.27. Found: C, 69.44; H, 8.82; N, 5.45.

EXAMPLE 33

N-(6-Methoxyquinolin-5-yl)-2-(hexylthio)decanoic amide

Commercially available 6-methoxyquinoline (13.80 g) was nitrated according to the procedure of Campbell, et. al. (J. Am. Chem. Soc., 1946, 68, 1559) to give 5-nitro-6-methoxyquinoline (17.51 g). This crude product was directly reduced according to the procedure of Jacobs, et. al. (J. Am. Chem. Soc., 1920, 42, 2278 ) to give 5-amino-6-methoxyquinoline (6.25 g). This material (0.45 g) was coupled with 2-hexanethiodecanoic acid (0.75 g, prepared according to the procedures described in Examples 1 and 3) using the procedure described in Example 25 to give the title compound (0.63 g).

M.p. 88°–89° C. $^1$H NMR: δ8.80 (d, 3 Hz, 1H); 8.59 (s, 1 H); 8.08 (d, 8 Hz, 1H); 8.02 (d, 7 Hz, 1H); 7.51 (d, 8 Hz, 1H); 7.36 (d, 3 & 7 Hz, 1H); 3.55 (t, 6 Hz, 1H); 2.73 (t, 6 Hz, 2H); 2.14–1.21 (m, 22H); 0.89 (t, 6 Hz, 6H). $^{13}$C NMR: δ172.10, 151.50, 148.50, 143.90, 131.52, 129.93, 126.00, 121.33, 118.30, 115.76, 56.37, 51.35, 33.23, 32.02, 31.86, 31.43, 29.43, 29.25, 29.35, 28.71, 27.62, 22.67, 22.54, 14.02. IR (KBr) cm$^{-1}$: 3233, 2920, 2849, 1659, 1526, 1501. Mass spectrum m/e (relative intensity): M+444.28 (4), 328.22 (9), 243.18 (14), 229.08 (14), 216.06 (14), 174.20 (100). Anal.: Calc'd for $C_{26}H_{40}N_2O_2S$: C, 70.23; H, 9.07; N, 6.30. Found: C, 70.05; H, 9.03; N, 6.23.

EXAMPLE 34

N-(6-methylthioquinolin-5-yl)-2-(hexylthio)decanoic amide

Commercially available 6-chloroquinoline (33.3 g) was nitrated according to the procedure described in Example 33 to give 5-nitro-6-chloroquinoline (20.36 g). This material (15 g) was allowed to react with sodium methylthiolate according to the procedure of Massie (Iowa State Coll. J. Sci. 1946, 21, 41; CA 41:3044 g) to give 5-nitro-6-methylthioquinoline (13.61 g). This material (3.70 g) was reduced using iron (5.62 g) and hydrochloric acid (1.5 ml) in 50% aqueous ethanol (50 ml) to give 5-amino-6-methylthioquinoline (3.0 g). This material (3.0 g) was coupled with 2-hexanethiodecanoic acid (5.83 g, prepared according to the procedures described in Examples 1 and 3) using the procedure described in Example 25, to give the title compound (3.8 g).

M.p. 91°–92° C. $^1$H NMR: δ8.85 (d, 3 Hz, 1H) ; 8.62 (s, 1 H); 8.05 (d, 9 Hz, 1H); 8.00 (d, 9 Hz, 1H); 7.65 (d, 9 Hz, 1H); 7.40 (dd, 3 & 9 Hz, 1H); 3.55 (t, 8 Hz, 1H); 2.80 (t, 8 Hz, 2H); 2.50 (s, 3H) ; 2.10–1.35 (m, 17H) ; 0.91 (t, 9 Hz, 6H) . $^{13}$C NMR: δ172.00, 149.84, 131.37, 129.61, 126.91, 121.76, 51.22, 33.16, 32.36, 31.91, 31.47, 29.47, 29.34, 29.30, 28.69, 27.82, 22.73, 22.59, 15.77, 14.17, 14.08. IR (CHCl$_3$) cm$^{-1}$: 3318, 2923, 2852, 1677, 1586, 1567. Mass spectrum m/e (relative intensity): M+460.2 (2), 413.2 (6), 344.2 (23), 295.2 (13), 243.2 (16), 217.0 (70), 190.1 (100). Anal.: Calc'd for $C_{26}H_{40}N_2OS_2$: C, 67.78; H, 8.75; N, 6.08. Found: C, 68.27; H, 8.46; N, 5.85.

EXAMPLE 35

N-(Quinolin-5-yl)-N'-(4-(3-methylbutyl) phenylmethyl)-N'-heptylurea

5-Aminoquinoline was converted to the title compound according to the procedure described in Example 28.

Oil. $^1$NMR: δ8.80 (d, 4 Hz, 1H); 7.82 (d, 9 Hz, 1H); 7.65 (dd, 6 & 9 Hz, 1H); 7.61 (d, 6 Hz, 1H); 7.48 (d, 9 Hz, 1H); 7.26 (d, 6 Hz, 2H); 7.22 (d, 6 Hz, 2 H); 7.15 (dd, 4 & 9 Hz, 1H); 6.66 (s, 1H); 4.53 (s, 2H); 3.55 (t, 9 Hz, 2H); 2.65 (t, 9 Hz, 2H); 1.70 (m, 2H); 1.60 (m, 3 H); 1.32 (m, 8H); 1.00 (d, 6 Hz, 6H); 0.88 (t, 6 Hz, 3H) . $^{13}$C NMR: δ156.03, 150.00, 148.69, 143.30, 134.54, 134.20, 129.89, 129.35, 129.31, 128.94, 126.96, 125.91, 120.73, 120.46, 51.19, 48.95, 41.05, 33.51, 31.87, 29.18, 28.75, 27.77, 27.06, 22.66, 22.60, 14.14. IR (CHCl$_3$) cm$^{-1}$: 3416, 2913, 2855, 1665, 1596, 1509. Mass spectrum m/e (relative intensity): M+445.3 (4), 304.2 (6), 274.3 (7), 190.1 (8), 161.2 (100). High resolution mass spectra: m/e 445.3104, calc'd for C$_{29}$H$_{39}$N$_3$O: 445.3093. Anal.: Calc'd for C$_{29}$H$_{39}$N$_3$O: C, 78.12; H, 8.82; N, 9.43. Found: C, 75.75; H, 8.55; N, 9.00.

EXAMPLE 36

N-(6-Methoxyquinolin-5-yl)-N'-(4-(3-methylbutyl)phenylmethyl)-N'-heptylurea

5-Amino-6-methoxyquinoline, prepared as described in Example 33, was converted to the title compound according to the procedure described in Example 28.

M.p. 86°–87° C. $^1$NMR: δ8.73 (d, 3 Hz, 1H); 8.15 (d, 6 Hz,1H); 7.94 (d, 8 Hz, 1H); 7.39 (d, 8 Hz, 1H); 7.30 (m, 3 Hz, H); 7.22 (d, 6 Hz, 2H); 6.44 (s, 1 Hz, H); 4.62 (s, 2 Hz, H); 3.80 (s, 3 Hz, H); 3.43 (t, 9 Hz, 2H); 2.62 (t, 9 Hz, 2H); 1.76–1.21 (m, 13 Hz, H); 0.95 (d, 6 Hz, 6H); 0.88 (t, 6 Hz, 3H). $^{13}$C NMR:δ156.97, 149.90, 148.27, 143.74, 142.49, 134.83, 132.39, 128.78, 128.09, 127.18, 126.12, 121.11, 120.80, 115.49, 56.25, 50.72, 48.08, 40.91, 33.45, 31.82, 29.12, 28.61, 28.45, 27.70, 26.96, 22.58, 22.54, 14.09. IR (CHCl$_3$ cm$^{-1}$: 3395, 2953, 2924, 1651, 1504. Mass spectrum m/e (relative intensity): M+475.4 (6), 334.3 (11), 200.1 (14), 173.1 (17), 161.2 (100). Anal.: Calc'd for C$_{36}$H$_{41}$N$_3$O$_2$: C, 75.75; H, 8.69; N, 8.83. Found: C, 75.58; H, 8.90; N, 8.68.

EXAMPLE 37

N-(7-Methoxyisoquinolin-8-yl)-2-(4-(1-methylpropyl)phenoxy)nonanoic amide

7-Methoxy-8-aminoquinoline, prepared by reduction of the corresponding nitro compound according to Example 31, was coupled with 2-(4-(1-methylpropyl)phenoxynonanoic acid according to the procedure of Example 25 to give the title compound.

Oil. $^1$NMR: δ9.14 (s, 1H); 8.39 (d, 5 Hz, 1H); 8.12 (s, 1H); 7.73 (d, 7 Hz, i H); 7.54 (d, 5 Hz, 1 H); 7.44 (d, 7 Hz, 1H); 7.16 (d, 6 Hz, 2H) ; 7.01 (d, 6 Hz, 2H); 4.74 (t, 5 Hz, 1H); 3.79 (s, 3H); 2.61 (tq, 10 and 10 Hz, 1H); 2.14 (m, 2H); 1.58 (m, 4H); 1.46–1.22 (br, m, 8H); 1.20 (d, 5 Hz, 3H) ; 0.86 (m, 6H). $^{13}$C NMR: δ172.16, 155.80, 151.89, 148.40, 141.53, 140.95, 131.04, 128.19, 127.30, 125.60, 119.96, 118.70, 115.40, 115.20, 79.93, 56.38, 40.89, 33.66, 31.79, 31.27, 29.38, 29.19, 25.36, 22.64, 22.00, 14.09, 12.25. IR (CHCl$_3$) cm$^{-1}$: Mass spectrum m/e (relative intensity): M+462.30 (6), 314.22 (100), 285.22 (50), 229.12 (59).

EXAMPLE 38

N-(2-Phenyl-4-methoxycarbonylquinolin-3-yl)-2-(4-(1-methylpropyl)phenoxy)nonanoic amide 2-phenyl-4-methoxycarbonylquinolin-3-ylquinoline was coupled with 2-(4-(1-methylpropyl)phenoxynonanoic acid according to Example 25 to give the title compound.

M.p. 89°–91° C. $^1$NMR: δ8.56 (s, 1H); 8.14 (d, 9 Hz, 1 H); 8.05 (d, Hz, 1H); 7.71 (dd, 7 and 7 Hz, 1H); 7.58 (dd, 7 & 7 Hz, 1H); 7.52 (d, 7 Hz, 2H); 7.36 (m, 3H); 7.07 (d, 8 Hz, 2H); 6.69 (d, 8 Hz, 2H); 4.41 (t, 6 Hz, 1H); 3.89 (s, 3H); 2.55 (tq, 7 and 7 Hz, 1H); 1.74 (m, 2H); 1.58 (m, 2H); 1.10–1.40 (br, m, 10H); 0.84 (m, 6H). $^{13}$C NMR: δ170.78, 166.20, 155.56, 146.30, 141.51, 138.40, 132.60, 129.90, 129.66, 128.96, 128.68, 128.61, 128.17, 127.95, 124.95, 123.81, 121.70, 115.18, 52.76, 40.87, 32.93, 31.73, 31.25, 29.04, 25.03, 22.61, 22.01, 14.08, 12.24. IR (CHCl$_3$) cm$^{-1}$: 3410, 2960, 1725, 1680, 1620. Mass spectrum m/e (relative intensity): M+566.36 (13), 417.24 (29), 389.26 (23), 357.22 (13), 205.12 (45), 279.12 (100). Anal.: Calc'd for C$_{36}$H$_{42}$N$_2$O$_4$: C, 76.30; H, 7.47; N, 4.94. Found: C, 76.01; H, 7.55; N, 4.91.

EXAMPLE 39

N-(3-Methoxypyridin-2-yl)-2-(4-(1-methylpropyl)phenoxy)nonanoic amide

3-Methoxy-2-aminopyridine, prepared by reduction of the corresponding nitro compound according to Example 31, was coupled with 2-(4-(1-methylpropyl)phenoxynonanoic acid according to Example 25 to give the title compound.

Oil. $^1$H NMR: δ8.90 (s, 1H); 8.05 (d, 3 Hz, 1H); 7.25 (m, 3H); 6.97 (d, 3 Hz, 1H); 6.89 (d, 9 Hz, 2H); 4.64 (t, 7 Hz, 1H); 3.74 (s, 3H); 2.50 (tq, 12 & 12 Hz, 1H); 1.98 (m, 2H); 1.51 (m, 4H); 1.18–1.08 (br, m, 11H); 0.84 (t, 4 Hz, 3H); 0.76 (t, 5 Hz, 3H). $^{13}$C NMR: δ172.40, 156.00, 140.10, 128.15, 119.86, 117.34, 115.45, 55.68, 40.84, 33.20, 32.30, 31.75, 31.24, 29.34, 29.11, 27.60, 25.26, 22.61, 21.70, 14.06, 12.19. IR (CHCl$_3$) cm$^{-1}$: 3387, 2922, 2854, 1702, 15.98. Mass spectrum m/e (relative intensity): M+412.34 (8), 313.22 (41), 263.22 (100), 151.08 (30). Anal.: Calc'd for C$_{25}$H$_{36}$N$_2$O$_3$: C, 72.78; H, 8.80; N, 6.80. Found: C, 71.49, H, 8.88; N, 6.03.

EXAMPLE 40

N-(2-Methoxy-4-methylpyridin-2-yl)-2-(4-(1-methylpropyl)phenoxy)nonanoic amide 3-Nitro-4-methyl-2-pyridone was methylated with methyl iodide and reduced with zinc and acetic acid to give 2-methoxy-3-amino-4-methylpyridine. This material was coupled with 2-(4-(1-methylpropyl)phenoxynonanoic acid according to the procedure of Example 25 to give the title compound.

Oil. $^1$H NMR: δ8.19 (s, 1H); 7.10 (d, 7 Hz, 2H); 7.04 (d, 5 Hz, 1H); 6.93 (d, 7 Hz, 2H); 6.03 (d, 5 Hz, 1H); 4.63 (t, 6 Hz, 1H); 3.48 (s, 3H); 2.53 (tq, 11 & 11 Hz, 1 H); 2.07 (s, 3H); 2.03 (m, 2 H); 1.55 (m, 4H); 1.28 (m, 8 H); 1.18 (d, 6 Hz, 3H); 0.87 (m, 3H); 0.79 (t, 5 Hz, 3H) . $^{13}$C NMR: δ170.87, 159.58, 155.83, 143.55, 141.21, 133.70, 128.08, 124.35, 115.47, 109.06, 40.84, 37.44, 33.37, 31.75, 31.28, 31.25, 29.28, 29.07, 25.19, 22.61, 21.92, 19.47, 14.08, 12.20. IR (CHCl$_3$) cm$^{-1}$: 2920, 2852, 1685, 1655, 1606. Mass spectrum m/e (relative intensity): M+426.32 (10), 327.16 (7), 277.20 (52), 249.20 (35), 165.18 (100). Anal.: Calc'd for C$_{26}$H$_{38}$N$_2$O$_3$: C, 73.20; H, 8.98; N, 6.57. Found: C, 73.06; H, 9.11; N, 6.28.

EXAMPLE 41

N-(2-Methoxy-4-methylpyridin-2-yl)-2-(hexylthio)decanoic amide

3-Nitro-4-methyl-2-pyridone was methylated with methyl iodide and reduced with zinc and acetic acid to give 2-methoxy-3-amino-4-methylpyridine. This material was coupled with 2-hexylthiodecanoic acid according to the procedure of Example 25 to give the title compound.

M.p. 83°–85° C. $^1$NMR: δ8.55 (s, 1H) ; 7.04 (d, 6 Hz, 1 H); 6.07 (d, 6 Hz, 1H); 3.54 (s, 3H) ; 3.41 (t, 6 Hz, 1H); 2.12 (s, 3H); 2.03–1.17 (br, m, 22H); 0.84 (t, 5 Hz, 3H). $^{13}$C NMR: δ171.36, 159.74, 142.90, 133.40, 125.06, 109.20, 50.91, 37.47, 33.01, 31.82, 31.73, 31.38, 29.33, 29.27, 29.25, 28.52, 27.55 22.66, 22.52, 19.51, 14.10, 14.03. IR (KBr) cm$^{-1}$: 3232, 2920, 2850, 1652, 1592. Mass spectrum m/e (relative intensity): M+408.38 (5), 292.30 (16), 193.12 (17), 165.10 (54), 138.22 (100) . Anal.: Calc'd for $C_{23}H_{40}N_2O_2S$: C, 67.60; H, 9.87; N, 6.86. Found: C, 67.56; H, 9.56; N, 6.58.

EXAMPLE 42

N-(2-Methoxy-4-methylpyridin-2-yl)-N'-(4,(3-methylbutyl)phenylmethyl)-N'-heptylurea 3-Nitro-4-methyl-2-pyridone was methylated with methyl iodide and reduced with zinc and acetic acid to give 2-methoxy-3-amino-4-methylpyridine. This material was converted to the title compound according to the procedure described in Example 28.

M.p. 90°–91° C. $^1$NMR: δ7.20 (d, 15 Hz, 2H); 7.16 (d, 15 Hz, 2H); 6.95 (d, 6 Hz, 1H); 6.82 (s, 1H); 6.08 (d, 6 Hz, 1H); 4.53 (s, 2H); 3.53 (s, 3H); 3.31 (t, 6 Hz, 2H); 2.58 (t, 6 Hz, 2H); 2.15 (s, 3H); 1.70–1.43 (br, m, 8H); 1.24 (m, 10H); 0.90 (d, 5 Hz, 6H) ; 0.86 (t, 4 Hz, 3H). $^{13}$C NMR: δ159.98, 155.75, 142.66, 140.27, 135.04, 131.35, 128.63, 128.33, 128.07, 127.54, 127.32, 109.91, 53.87, 50.39, 49.55, 47.44, 40.89, 40.81, 37.48, 33.43, 31.84, 31.78, 30.12, 29.25, 29.02, 28.17, 27.66, 27.35, 26.99, 22.63, 22.54, 19.48, 14.09. IR (KBr) cm$^{-1}$: 2952, 2922, 1660, 1635, 1590. Mass spectrum m/e (relative intensity): M+439.40 (14), 298.26 (10), 274.30 (26), 190.20 (40), 165.08 (81), 161.14 (100). Anal.: Calc'd for $C_{27}H_{41}N_3O_2$: C, 73.76; H, 9.40; N, 9.56. Found: C, 73.85; H, 9.25; N, 9.35.

EXAMPLE 43

N-(Imidazo[1,2-a]pyridin-3-yl)-2-(4-(1-methylpropyl)-phenoxy)nonanoic amide

3-Aminoimidazo[1,2-a]pyridine, synthesized by reduction of the corresponding nitro compound according to Example 31, was coupled with 2-(4-(1-methylpropyl)-phenoxynonanoic acid according to the procedure of Example 25 to give the title compound.

Oil. $^1$H NMR: δ8.78 (s, 1H); 7.72 (d, 6 Hz, 1H); 7.62 (d, 8 Hz, 1H); 7.55 (s, I H); 7.24 (d, 9 Hz, 2H); 7.20 (dd, 7 and 7 Hz, 1H); 6.94 (d, 9 Hz, 2H); 6.85 (dd, 7 and 7 Hz, 1H); 4.52 (t, 6 Hz, 1H); 2.51 (tq, 11 and 11 Hz, 1 H); 1.94 (m, 2H); 1.50 (m, 4H); 1.20–1.10 (br m, 11H); 0.90–0.70 (br. m, 6H). $^{13}$C NMR: 172.45, 156.14, 148.75, 144.99, 140.63, 128.32, 127.90, 127.84, 121.41, 121.17, 120.89, 117.20 114.91, 76.93, 61.03, 41.15, 34.43, 32.94, 31.23, 29.14, 28.69, 25.01, 22.66, 21.93, 21.81, 14.16, 12.19. IR (KBr) cm$^{-1}$: Mass spectrum m/e (relative intensity): M+421.28 (25), 272.18 (51), 159.04 (58), 133.04 (100). Anal.: Calc'd for $C_{26}H_{35}N_3O_2$: C, 74.25; H, 8.39; N, 9.99. Found: C, 73.82; H, 9.02; N, 9.56.

EXAMPLE 44

N-(Imidazo[1,2-a ]pyridin-3-yl)-2-(hexylthio) decanoic amide

3-Aminoimidazo[1,2-a]pyridine, synthesized by reduction of the corresponding nitro compound according to the procedure of Example 31, was coupled with 2-hexylthiodecanoic acid according to Example 25 to give the title compound.

$^1$H NMR (CDCl$_3$): 8.66 (S, 1H); 7.75 (d, 5 Hz, 1H); 7.62 (d, 8 Hz, 1H); 7.52 (s, 1H); 7.22 (dd, 7 & 8 Hz, 1H); 6.84 (dd, 5 & 7 Hz, 1H); 3.48 (t, 6 Hz, 1H); 2.67 (t, 6 Hz, 2H); 2.03 (m, 1H); 1.83 (m, 1H); 1.70–1.15 (m, 20H); 0.85 (m, 6H).

EXAMPLE 45

N-(8-Chloro-6-methoxyquinolin-5-yl)-2-hexylthiodecanoic amide

5-Amino-6-methoxy-8-chloroquinoline, produced as a side product of the reduction procedure described in Example 33, was coupled with 2-hexylthiodecanoic acid according to the procedure described in Example 25 to give the title compound.

Mp=110°–111° C. Anal.: Found: C, 65.40; H, 8.06; N, 5.73. Calc'd for $C_{26}H_{39}ClN_2O_2S$: C, 65.18; H, 8.42; N, 5.85.

EXAMPLE 46

N-(6,8-Di(methylthio)quinolin-5-yl)-2-hexylthiodecanoic amide

5-Amino-6,8-di(methylthio) quinoline, produced as a side product of the procedure described in Example 34, was coupled with 2-hexylthiodecanoic acid according to the procedure described in Example 25 to give the title compound.

Mp=91°–93° C.

EXAMPLE 47

N-(6-Methylthioquinolin-5-yl)-2-(4-sec-butylphenoxy)nonanoic amide

5-Amino-6-methylthioquinoline, prepare as described in Example 34, was coupled with 2-(4-sec-butylphenoxy) nonanoic acid according to the procedure described in Example 25 to give the title compound.

Oil. Anal.: Found: C, 71.35; H, 7.98; N, 5.54. Calc'd. for $C_{29}H_{38}N_2O_2S$: C, 72.76; H, 8.00; N, 5.85.

EXAMPLE 48

N-(6-Methylthioquinolin-5-yl)-2-octanyl-1,3-dithiane-2-carboxamide

5-Amino-6-methylthioquinoline, prepared as described in Example 34, was coupled with 2-octanyl-1,3-dithiane-2-carboxylic acid, prepared by treatment of 1,3-dithiane-2-carboxylic acid with sodium hexamethyldisilazide and octanyl bromide, according to Example 25 to give the title compound.

Oil. Anal.: Found: C, 59.11; H, 5.81; N, 6.07. Calc'd. for $C_{23}H_{32}N_2OS_3$: C, 61.57; H, 7.19; N, 6.24.

EXAMPLE 49

N-(6-ethoxyquinolin-5-yl)-2-hexylthiodecanoic amide

6-Hydroxyquinoline was treated with sodium hydride and ethyl iodide to give 6-ethoxyquinoline. This material was nitrated, reduced and coupled with 2-hexylthiodecanoic acid according to the procedure of Example 33 to give the title compound.

Mp=88°–90° C. Anal.: Found: C, 70.37; H, 9.01; N, 6.26. Calc'd. for $C_{27}H_{42}N_2O_2S$: C, 70.69; H, 9.23; N, 6.11.

EXAMPLE 50

N-(6-fluoroquinolin-5-yl)-2-hexylthiodecanoic amide

6-Fluoroquinoline, prepared according to the procedure of Sveinbjornsson et. al. (J. Org. Chem., 1951, 16, 1450), was nitrated, reduced and coupled with 2-hexylthiodecanoic aicd according to the procedure of Example 33 to give the title compound.

Mp=74°–75° C. Anal.: Found: C, 69.04; H, 8.55; N, 6.57. Calc'd. for $C_{25}H_{37}FN_2OS$: C, 69.40; H, 8.62; N, 6.48.

The title compounds of Examples 51–53 were prepared according to the procedure described in Example 4.

EXAMPLE 51

4,5-Dimethyl-trans-2-n-heptyl-N-(2,4,6-trimethoxyphenyl)-cyclohex-4-enecarboxamide 72% yield. IR(CHCl$_3$): 1675 cm$^{-1}$. $^1$H NMR: δ0.86 (t, 3H); 1.62 (s) and 1.12–2.48 (c) (total 24H); 3.78 (s, 6H); 3.79 (s, 3H); 6.13 (s, 2H); 6.48 (s, 1H).

EXAMPLE 52

4.5-Dimethyl-trans-2-n-nonyl-N-(2,4,6-trimethoxyphenyl)cyclohex-4-enecarboxamide 66% yield. IR(CHCl$_3$): 1676 cm$^{-1}$. $^1$H NMR: δ0.86 (t, 3H); 1.62 (s) and 1.12–2.48 (c) (total 28 H); 3.78 (s, 6H); 3.79 (s, 3H); 6.13 (s, 2H); 6.48 (s, 1H).

EXAMPLE 53

4,5-Dimethyl-trans-2-n-octyl-N-(2,4,6-trimethoxyphenyl)cyclohex-4-enecarboxamide 46% yield. IR(CHCl$_3$): 1676 cm$^{-1}$. $^1$H NMR: δ0.86 (t, 3H); 1.62 (s) and 1.12–2.48 (c) (total 26H); 3.78 (s, 6H); 3.79 (s, 3H); 6.13 (s, 2H); 6.48 (s, 1H).

Using the procedure described in Example 4, the amides in the bicyclo[2.2.1]hept-5-ene and bicyclo[2.2.2]oct-5-ene series of Examples 54–59 were obtained as mixtures of endo and exoisomers which could be separated by column chromatography on silica gel, eluting with hexane/ethyl acetate.

EXAMPLE 54

3-n-Nonyl-endo-N-(2,4,6-trimethoxyphenyl)-bicyclo-[2.2.1]hept-5-ene-2-carboxamide 30% yield. IR(CHCL$_3$): 1663 cm$^{-1}$. $^1$H NMR: δ0.86 (t,3H); 1.15–1.62 (c, 18H); 1.79 (c, 1H); 2.51 (c, 1H); 2.61 (c, 1H); 3.16 (c, 1H); 3.77 (s, 6H); 3.78 (s, 3H); 6.11 (s) and 6.14 (c) (total 3H); 6.3 (c, 1H); 6.36 (s, 1H).

EXAMPLE 55

Endo-3-n-nonyl-exo-N-(2,4,6-trimethoxyphenyl)-bicyclo-[2.2.1]hept-5-ene-2-carboxamide 26% yield. IR(CHCl$_3$): 1678 cm$^{-1}$. $^1$NMR: δ0.86 (t, 3H); 1.14–1.45 (c, 17H); 1.66 (c, 1H); 1.91 (c, 1H); 2.4 (c, 1H); 2.8 (c, 1H); 3.0 (c, 1H); 3.78 (s, 9H); 6.13 (s+c, 3H); 6.21 (c, 1H); 6.42 (s, 1H).

EXAMPLE 56

Exo-3-n-octyl-endo-N-(2,4,6-trimethoxyphenyl)-bicyclo-[2.2.2]oct-5-ene-2-carboxamide 20% yield. IR(CHCl$_3$): 1666 cm$^{-1}$. $^1$H NMR: δ0.86 (t, 3H); 1.02–1.87 (c, 19H); 2.11 (c, 1H); 2.45 (c, 1H); 2.84 (c, 1H); 3.76 (s, 6H); 3.78 (s, 3H); 6.11 (s, 2H); 6.3 (c, 1H); 6.42 (s, 1H); 6.5 (c, 1H).

EXAMPLE 57

Endo-3-n-octyl-exo-N-(2,4,6-trimethoxyphenyl)-bicyclo[2.2.2]oct-5-ene-2-carboxamide 24% yield. IR(CHCl$_3$): 1680 cm$^{-1}$. $^1$H NMR: δ0.86 (t, 3H); 1.06 (c, 1H); 1.25 (c, 14H); 1.65 (c, 2H); 1.89 (c, 2H); 2.16 (c, 1H); 2.46 (c, 1H); 2.78 (c, 1H); 3.77 (s, 6H); 3.79 (s, 3H); 6.13 (s, 2H); 6.21 (c, 1H); 6.32 (c, 1H); 6.43 (s, 1H).

EXAMPLE 58

Exo-2-n-nonyl-endo-N-(2,4,6-trimethoxyphenyl) bicyclo-[2.2.1]hept-5-ene-2-carboxamide 40% yield. IR(CHCl$_3$): 1677 cm$^{-1}$. $^1$H NMR: δ0.86 (t, 3H); 1.27 (c, 12H); 1.4–1.7 (c, 6H); 1.88 (c, 1H); 2.02 (c, 1H); 2.82 (c, 2H); 3.76 (s, 6H); 3.77 (s, 3H); 6.12 (s, 2H); 6.2 (c, 2H); 6.4 (s, 1H).

EXAMPLE 59

Endo-2-n-nonyl-exo-N-(2,4,6-trimethoxyphenyl)-bicyclo-[2.2.1]hept-5-ene-2-carboxamide 2% yield. IR 1675 cm$^{-1}$. $^1$H NMR: δ0.84 (t, 3H); 1.12–2.06 (c, 19H); 2.45 (c, 1H); 2.82 (c, 1H); 3.17 (c, 1H); 3.77 (s, 6H); 3.79 (s, 3H); 6.05–6.27 (c, 4H); 6.6 (s, 1H).

The title compounds of Examples 60–64 were prepared according to the procedure described in Example 4.

EXAMPLE 60

2-n-Nonyl-N-(2,4,6-trimethoxyphenyl)indane-2-carboxamide

72% yield. IR(CHCl$_3$): 1676 cm$^{-1}$. $^1$NMR: δ0.86 (t, 3H); 1.24 (c, 12H); 1.49 (c, 3H); 1.75 (c, 2H); 2.97 (d, 2H); 3.54 (d, 2H); 3.74 (s, 6H); 3.78 (s, 3H); 6.12 (s, 2H); 6.51 (s, 1H); 7.2 (c, 4H).

EXAMPLE 61

2-n-Octyl-N-(2,4,6-trifluorophenyl)-1,2,3,4-tetrahydro-2-naphthamide

22% yield. $^1$H NMR: δ0.86 (t, 3H); 1.15–1.6 (c, 13H); 1.9 (c, 2H); 2.2 (c, 1H); 2.88 (c, 1H); 3.27 (d, 1H); 6.66 (c, 3H); 7.13 (s, 4H).

EXAMPLE 62

2-n-Octyl-N-(2,4,6-trimethoxyphenyl)-1,2,3,4-tetrahydro-2-naphthamide

65% yield. $^1$H NMR: δ0.87 (t, 3H); 1.29 (c, 10H); 1.5 (c, 3H); 1.86 (c, 2H); 2.22 (c, 1H); 2.8 (c, 2H); 3.0 (c, 1H); 3.3 (d, 1H).; 3.66 (s, 6H); 3.75 (s, 3H); 6.06 (s, 2H); 6.56 (s, 1H); 7.10 (s, 4H).

EXAMPLE 63

2-n-Decyl-N-(2,4,6-trimethoxyphenyl)indane-2-carboxamide

61% yield. IR(CHCl$_3$) 1675 cm$^{-1}$.

$^1$NMR: δ0.86 (t, 3H); 1.23 (c, 14H); 1.49 (c, 2H); 1.75 (c, 2H); 2.97 (d, 2H); 3.54 (d, 2H); 3.74 (s, 6H); 3.78 (s, 3H); 6.12 (s, 2H); 6.5 (s, 1H); 7.2 (c, 4H).

EXAMPLE 64

2-n-Decyl-N-(2,4,6-trifluorophenyl)indane-2-carboxamide

33% yield. IR(CHCl$_3$) 1695 cm$^{-1}$.

$^1$NMR: δ0.86 (t, 3H); 1.23 (c, 14H); 1.42 (c, 2H); 1.78 (c, 2H); 3.02 (d, 2H); 3.5 (d, 2H); 6.72 (c, 3H); 7.22 (c, 4H).

EXAMPLE 65

2-n-Nonyl-N-(2,4,6-trifluorophenyl)-1,2,3,4-tetrahydro-2-naphthamide

To a solution of 1.0 g (6.8 mmole) 2,4,6-trifluoroaniline and 830 mg (6.8 mmole) 4-dimethylaminopyridine in 40 ml methylene chloride cooled to 5° C. under nitrogen was added a solution of 2.12 g (6.6 mmole) 2-n-nonyl-1,2,3,4-tetrahydro-2-naphthoyl chloride in 10 ml methylene chloride. The resulting solution was stirred at room temperature for 44 hours. Fifty milliters of methylene chloride was then added and the solution was washed sequentially with 30 ml aqueous hydrochloric acid, 30 ml water and 30 ml brine. The methylene chloride solution was dried over anhydrous sodium sulfate and concentrated to dryness in vacuo. The residue (2.5 g) was purified by column chromatography on silica gel eluting with 2:1 methylene chloride-hexane to yield 1.66 g (58% yield) of the desired product as a white, low melting solid.

IR(CHCl$_3$) 1691 cm$^{-1}$. $^1$H NMR: δ0.87 (t, 3H); 1.16–1.6 (c, 15H); 1.9 (c, 2H); 2.2 (c, 1H); 2.9 (c, 3H); 3.27 (d, 1H); 6.67 (m, 2H); 6.73 (s, 1H); 7.13 (s, 4H).

EXAMPLE 66

2-n-Nonyl-N-(2,4,6-trimethoxyphenyl)-1,2,3,4-tetrahydro-2-naphthamide

The title compound was prepared according to the procedure described in Example 65, except that 422 mg 2-n-nonyl-1,2,3,4-tetrahydro-2-naphthoyl chloride, 247 mg (1.3 mmole) 2,4,6-trimethoxyaniline, and 165 mg (1.3 mmole) 4-dimethylaminopyridine in 12 ml methylene chloride were stirred at room temperature for 20 hours. There was obtained 421 mg product (68% yield). IR(CHCl$_3$) 1670 cm$^{-1}$. $^1$H NMR: δ0.87 (t, 3H); 1.25 (c, 12H); 1.5 (c, 3H); 1.85 (c, 2H); 2.21 (c, 1H); 2.8 (C, 2H); 3.0 (c, 1H); 3.3 (d, 1H); 3.66 (s, 6H); 3.75 (s, 3H); 6.06 (s, 2H); 6.56 (s, 1H); 7.1 (s, 4H).

EXAMPLE 67

2-n-Nonyl-N-(2,4,6-trifluorophenyl)indane-2-carboxamide

The title compound was prepared according to the procedure described in Example 65, except that 398 mg (1.3 mmple) 2-n-nonylindane-2-carbonyl chloride, 220 mg (1.5 mmole) 2,4,6-trifluoroaniline, and 187 mg (1.5 mmole) 4-dimethylaminopyridine in 12 ml methylene chloride were stirred at room temperature for 44 hours. There was obtained 290 mg product, 54% yield. IR(CHCl$_3$): 1693 cm$^{-1}$. $^1$H NMR: δ0.86 (t, 3H); 1.23 (c, 12H); 1.41 (c, 2H); 1.78 (c, 2H); 3.02 (d, 2H); 3.5 (d, 2H); 6.7 (c, 3H); 7.18 (c, 4H).

EXAMPLE 68

N-(2,4,6-Trimethoxy)phenyl-2-[(2-(6-ethoxybenzothiazol)thio]octanamide

The title compound was prepared according to the procedures described in Examples 5 and 6.

M.p. 78°–81° C. $^1$H NMR (CDCl$_3$) 8.13 (s, 1); 7.69 (d, 4 Hz, 1); 7.22 (d, 1 Hz, 1); 6.98 (dd, 1); 6.06 (s, 1); 4.65 (t, 4 Hz, 1); 4.07 (q, 3 Hz, 2); 3.81 (s, 2); 3.76 (s, 2); 3.54 (s, 6); 2.2–1.2 (m, 12); 0.89 (m, 3). IR(CHCl$_3$) 3400, 2929, 1690, 1520 cm$^{-1}$.

EXAMPLE 69

N-(2,4,6-Trimethoxy)phenyl-3-((1-tert-nonyl)thio)octanamide

The title compound was prepared according to the procedures described in Examples 5 and 6.

Oil. $^1$H NMR (CDCl$_3$) 8.10 (bs, 1); 3.82 (s, 3); 3.79 (s, 6); 3.40 (bs, 1); 1.98–0.80 (m, 32). IR(CHCl$_3$) 3320, 2950, 1670, 1600 cm$^{-1}$.

EXAMPLE 70

N-(5-Isoquinolinyl)-2-((1-N-hexyl)thio)heptanamide

The title compound was prepared according to the procedures described in Examples 1 through 4.

M.p. 83°–85° C. $^1$NMR (CDCl$_3$) 9.30 (bs, 1); 9.16 (s, 1); 8.48 (d, 4 Hz, 1); 8.23 (d, 4 Hz, 1); 7.71–7.46 (m, 3); 3.47 (t, 2 Hz, 1); 2.58 (t, 5 Hz, 2); 2.08–0.76 (m, 20). IR (CHCl$_3$) 3317, 2921, 1682, 1515 cm$^{-1}$.

EXAMPLE 71

N-(2,4,6-Trimethoxy)phenyl-2-((1-N-hexyl)thio)decanoamide

The title compound was prepared according to the procedures described in Examples 5 and 6.

M.p. 55°–56° C. C, calc'd, 67.19; Found, 66.41. $^1$H NMR (CDCl$_3$) δ7.81 (bs, 1); 6.14 (s, 2); 3.81 (s, 3); 3.78 (s, 6); 3.48 (s, 6); 3.46 (t, Hz, 1); 2.69 (bs, 2); 1.98–0.76 (m, 28). IR (CHCl$_3$) 3340, 2930, 1670, 1600 cm$^{-1}$.

EXAMPLE 72

N-(2,4,6-Trimethoxy)phenyl-2-((1-n-hexyl)sulfonyl)octanamide

The title compound was prepared by treating N-(2,4,6-trimethoxy)phenyl-2-((1-n-hexyl)thio) octanamide (0.5 g, 1.18 mmol) with m-chloroperoxybenzoic acid (0.56 g, 2.76 mmol) in dichloromethane (10 mL). Extractive work up and chromatography on silica gel (1:3 ethyl acetate:hexanes, eluent) provided N-(2,4,6-trimethoxy)phenyl-2-((1-n-hexyl)sulfonyl) octanamide (0.28 g, 52%).

M.p. 134°–137° C. $^1$NMR (CDCl$_3$) δ7.44 (s, 1); 6.17 (s, 2); 3.85 (s, 3); 3.27 (m, 1); 2.20 (m, 1); 2.20–0.93 (m, 26). IR (CHCl$_3$) 3370, 2930, 1690, 1600 cm$^{-1}$.

EXAMPLE 73

N-(2,4,6-Trimethoxy)phenyl-2-((1-N-hexyl)thio)hexanamide

The title compound was prepared by a procedure similar to that described in Examples 1 through 4.

M.p. 67°–69° C. $^1$H NMR (CDCl$_3$) δ7.76 (bs, 1); 6.12 (s, 2); 3.78 (s, 3); 3.76 (s, 3); 3.42 (t, 4 Hz, 1); 2.69–2.60 (m, 2); 1.99–1.19 (m, 14); 0.92–0.79 (m, 6).

EXAMPLE 74

N-(2,4,6-Trimethoxy)phenyl-2-((1-N-pentyl)thio)octanamide

The title compound was prepared according to the procedures described in Examples 5 and 6.

M.p. 85°–86° C. $^1$H NMR δ(CDCl$_3$) 7.78 (s, 1); 6.11 (s, 2); 3.77 (s, 3); 3.74 (s, 6); 3.44 (t, 4 Hz, 1); 2.66 (m, 2); 1.90–1.22 (m, 16); 0.87 (m, 6). IR (CHCl$_3$) 3350, 2930, 1675, 1610 cm$^{-1}$.

EXAMPLE 75

N-(2,4,6-Trimethoxy)phenyl-2-((1-N-hexyl)thio)pentanamide

The title compound was prepared according to the procedures described in Examples 5 and 6.

M.p. 74°–75° C. $^1$NMR (CDCl$_3$) δ7.81 (bs, 1); 6.15 (s, 2); 3.82 (s, 3); 3.79 (s, 6); 3.48 (t, 3 Hz, 1); 2.70 (m, 2); 1.98–0.85 (m, 8). IR (CHCl$_3$) 3320, 2920, 1675, 1600 cm$^{-1}$.

EXAMPLE 76

N-(2,4,6-Trimethoxy)phenyl-2-((1-N-hexyl)thio) heptamide

The title compound was prepared according to the procedures described in Examples 5 and 6.

M.p. 89°–91° C. $^1$H NMR (CDCl$_3$) δ7.82 (bs, 1); 6.16 (s, 2); 3.82 (s, 3); 3.80 (s, 6); 3.48 (t, 3 Hz, 1); 2.70 (m, 2); 2.00–0.84 (m, 22). IR (CHCl$_3$) 3340, 2930, 1675, 1600 cm$^{-1}$.

EXAMPLE 77 AND 78

N-(2,4,6-Trimethoxy)phenyl-2-((1-N-hexyl)sulfinyl) octanamide (Diastereomer A and Diastereomer B)

The title compound was prepared by treating N-(2,4,6-trimethoxy)phenyl-2-(1-n-hexyl)thiooctamide (0.5 g, 1.2 mmol) with m-chloroperoxybenzoic acid (0.29 g, 1.4 mmol) in dichloromethane (10 mL) at −20° C. Extractive work up and chromatography on silica gel (1:1 ethyl acetate:hexanes, eluent) provided Diastereomer A, m. p. 116°–118° C., (less polar, 0.18 g, 33%) and Diastereomer B, m.p. 105°–106° C., (more polar, 0.12 g, 12%).

EXAMPLE 79

N-(2,4,6-Trimethoxy)phenyl-2-((1-N-hexyl)thio) butanamide

The title compound was prepared according to the procedures described in Examples 5 and 6.

M.p 79°–80° C. $^1$H NMR (CDCl$_3$) δ7.84 (bs, 1); 6.17 (s, 2); 3.82 (s, 2); 3.81 (s, 6); 3.44 (t, 3 Hz, 1); 2.71 (m, 2); 2.02–0.86 (m, 16). IR (CHCl$_3$) 3340, 2960, 1675, 1600 cm$^{-1}$.

EXAMPLE 80

N-(2,4,6-Trimethoxy)phenyl-2-((1-N-butyl)thio) octanamide

The title compound was prepared according to the procedures described in Examples 5 and 6.

M.p. 87°–88° C. $^1$H NMR (CDCl$_3$) δ7.74 (s, 1); 6.80 (s, 2); 3.75 (s, 3); (s, 6); 3.40 (t, 4 Hz, 1); 2.63 (m, 2); 2.04–1.19 (m, 14); 0.88–0.80 (m, 6). IR (CHCl$_3$) 2930, 1680, 1605 cm$^{-1}$.

EXAMPLE 81

N-(2,4,6-Trimethoxy)phenyl-2-((2-thiazolyl)thio) octamide

The title compound was prepared according to the procedures described in Examples 5 and 6.

M.p. 81°–83° C. $^1$H NMR (CDCl$_3$) δ8.10 (s, 1); 7.62 (m, 1); 7.19 (m, 1); 6.06 (s, 2); 4.40 (t, 3 Hz, 1); 3.75 (s, 3), 3.66 (s, 6); 2.2–1.22 (m, 10); 0.86 (m, 3). IR (CHCl$_3$) 2920, 1685, 1600, 1460 cm$^{-1}$.

The title compounds of Examples 82–96 were prepared by a procedure similar to that of Examples 5 and 6.

EXAMPLE 82

N-(2,4,6-Trimethoxy)-2-((benzthiazol-2-yl)thio) octanamide

M.p. 108°–112° C. $^1$H NMR (CDCl$_3$) δ8.26 (s, 1); 7.78 (d, 4 Hz, 1); 7.72 (d, 4 Hz, 1); 7.35 (m, 1); 6.09 (s, 1); 6.00 (s, 1); 4.98 (t, 4 Hz, 1); 3.76 (s, 3); 3.70 (s, 3); 3.46 (s, 4); 2.2–1.2 (m, 10); 0.84 (m, 3). IR (CHCl$_3$) 2930, 1690, 1600, 1510, 1465, 1440 cm$^{-1}$. N Calc.: 590 Found: 5.29.

EXAMPLE 83

N-(2,4,6-Trimethoxy)phenyl-2-((1-N-decyl)thio) butanamide

M.p. 58°–59° C. $^1$H NMR (CDCl$_3$) δ7.85 (bs, 1); 6.17 (s, 2); 3.83 (s, 3); 3.80 (s, 3); 3.48 (t, 3 Hz, 1); 2.71 (m, 2); 2.06–0.86 (m, 24). IR (CHCl$_3$) 3350, 2910, 1675, 1600 cm$^{-1}$.

EXAMPLE 84

N-(N-Pentyl)-2-(2-(6-ethoxybenzthiazolyl)thio) decanamide

M.p. 48°–50° C. $^1$NMR (CDCl$_3$) δ7.68 (bs, 5 Hz, 1); 7.24 (bs, 1); 7.18 (d, 1 Hz, 1); 6.98 (q, 1 Hz, 1); 4.31 (t, 3 Hz, 1); 4.04 (q, 3, 6 Hz, 2); 3.22 (m, 2), 2.16–0.68 (m, 29). IR (CHCl$_3$) 3310, 2930, 1675, 1610 cm$^{-1}$.

EXAMPLE 85

N-(2,4,6-Trifluoro)phenyl-2-(N-hexyl) thiooctanamide

M.p. 63°–66° C. $^1$H NMR (CDCl$_3$) δ8.08 (bs, 1); 6.70 (t, 4 Hz, 2); 3.42 (t, 3 Hz, 1); 2.58 (t, 4 Hz, 2); 1.98–0.80 (m, 24). IR (CHCl$_3$) 3666, 29.23, 1692, 1644, 1511, 14.76 cm$^{-1}$.

EXAMPLE 86

N-(2.4,6-Trimethoxy)phenyl-2-(2-(6-ethoxybenzthiazolyl)thio)octanamide

Amorphous $^1$H NMR (CDCl$_3$) δ8.24 (s, 1); 7.64 (d, 6 Hz, 1); 7.16 (d, 1 Hz, 1); 6.92 (m, 1); 6.11 (s, 1); 6.08 (s, 1); 6.00 (s, 1); 4.58 (t, 4 Hz, 1); 4.00 (q, 3 Hz, 2); 3.78 (s, 3); 3.74 (S, 2) 3.70 (s, 2); 3.46 (s, 3); 2.2–1.2 (m, 9); 0.85 (m, 3 Hz, 3).

EXAMPLE 87

N-(2,4,6-Trimethoxy)phenyl-2-(2-(6-ethoxybenzthiazolyl)thio)pentanoamide

M.p. 44°–46° C. $^1$NMR (CDCl$_3$) δ8.18 (s, 1); 7.56 (d, 5 Hz, 1); 7.07 (d, 1 Hz, 1); 6.83 (m, 1); 5.91 (s, 2); 4.52 (t, 3 Hz, 1); 3.91 (q, 4 Hz, 2); 3.60 (s, 3); 3.38 (s, 6); 2.10–1.10 (m, 7); 0.88 (m, 3 Hz, 3). IR (CHCl$_3$) 2960, 1690, 1605, 1510, 1470 cm$^{-1}$.

EXAMPLE 88

N-(2,4,6-Trimethoxy)phenyl-2-(2-(5-chlorobenzthiazolyl)thio)hexanamide

M.p. 100°–101° C. $^1$H NMR (CDCl$_3$) δ8.20 (s, 1); 7.65 (d, 4 Hz, 1); 7.20 (m, 1); 7.08 (s, 1); 6.10 (s, 2); 4.72 (t, 4 Hz, 1); 3.79 (s, 9); 2.2–1.1 (m, 10); 0.88 (m, 3 Hz, 3).

EXAMPLE 89

N-(2,4,6-Trimethoxy)phenyl-2-(2-(6-ethoxybenzthiazolyl)thio)hexanamide

Amorphous. $^1$H NMR (CDCl$_3$) δ8.28 (s, 1); 7.66 (d, 5 Hz, 1); 6.94 (m, 1); 6.02 (s, 2); 4.61 (t, 4 Hz, 1); 4.03 (q, 3, Hz, 2); 3.74 (s, 3); 3.50 (s, 6); 2.15 (s, 2); 1.96–1.32 (m, 7); 0.92 (t, 4 Hz, 3). IR (CHCl$_3$) 2930, 1690, 1600, 1510, 1450 cm$^{-1}$.

EXAMPLE 90

N-(5-Isoquinolinyl)-2-((1-tet-nonyl)thio)hexanamide

M.p. 83°–85°. $^1$H NMM (CDCl$_3$) δ9.4 (s, 1); 9.2 (s, 1); 8.4 (m, 1), 7.8 (m, 1); 7.6 (m, 2); 3.55 (m, 1); 2.65 (m, 2); 2.2–1.8 (m, 2); 1.0–1.80 (m, 20); 0.8–1.0 (m, 6). IR (CHCl$_3$) 2920, 2860, 1690, 1530 cm$^{-1}$.

EXAMPLE 91

N-(5-Isoquinolinyl)-2-((1-N-butyl)thio)octanamide

Amorphous. $^1$H NMR (d-DMSO) δ9.42 (s, 1); 9.30 (m, 1); 8.60 (m, 1), 8.40 (m, 1); 7.82 (m, 2); 7.65 (m, 2); 3.60 (m, 1); 2.65 (m, 2); 2.1 (m, 1); 1.90 (m, 1); 1.2–1.8 (m, 15); 0.9 (m, 6). IR (CHCl$_3$) 2950, 2860, 1690, 1520, 1480 cm$^{-1}$.

EXAMPLE 92

N-(5-Isoquinolinyl)-2-(2-(6-ethoxybenzthiazolyl)thio)octanamide

M.p. 92°–93° C. $^1$H NMR (CDCl$_3$) δ9.13 (s, 1); 8.36 (d, 5 Hz, 1); 8.30 (d, 3 Hz, 1), 7.78 (d, 6 Hz, 1); 7.70 (t, 5 Hz, 3); 7.53 (t, 4 Hz, 1); 7.19 (s, 1); 7.0 (m, 1); 4.61 (t, 4 Hz, 1); 4.03 (q, 3 Hz, 2); 2.3–1.8 (m, 2); 1.6–1.2 (m, 11); 0.82 (m, 3). IR (CHCl$_3$) 2920, 1700, 1610, 1550, 1470 cm$^{-1}$.

EXAMPLE 93

N-(2,4,6-Trifluoro)phenyl-2-(2-(6-ethoxybenzthiazolyl)thio)decanamide

Amorphous. $^1$H NMR (CDCl$_3$) δ8.54 (s, 1); 7.67 (d, 4 Hz, 1); 7.20 (d, 1 Hz, 1); 7.00 (m, 1); 6.8–6.6 (m, 2); 4.48 (t, 3 Hz, 1); 4.03 (q, 3 Hz, 2); 2.2–1.0 (m, 17); 0.84 (m, 3). IR (CHCl$_3$) 2920, 2840, 1700, 1600, 1520 cm$^{-1}$.

EXAMPLE 94

N-(2,4,6-Trimethoxy)phenyl-2-(2-(6-ethoxybenzthiazolyl)thio)tetradodecanamide

M.p. 87°–89° C. $^1$H NMR (CDCl$_3$) δ8.27 (s, 1); 7.68 (d, 5 Hz, 1); 7.20 (d, 1 Hz; 1); 6.96 (m, 1); 6.04 (s, 2); 4.62 (t, 3 Hz, 1); 4.05 (q, 3 Hz, 2); 3.74 (s, 3); 3.51 (s, 6); 2.2–1.2 (m, 25); 0.84 (m, 3). IR (CHCl$_3$) 2920, 2860, 1690, 1600, 1510 cm$^{-1}$.

EXAMPLE 95

N-(6-Methoxyisoquinolin-5-yl)-2-((1-n-hexyl)thio)decanamide

Amorph. $^1$H NMR (CDCl$_3$) δ9.1 (s, 1); 8.5 (m, 1); 8.4 (m, 1); 7.9 (m, 1); 7.5 (m, 2); 7.35 (m, 2); 4.0 (s, 3); 3.5 (m, 1); 2.7 (m, 2); 2.05 (m, 1); 1.85 (m, 1); 1.2–1.8 (m, 15); 0.9 (m, 6). IR (CHCl$_3$) 2920, 1680, 1625, 1485 cm$^{-1}$.

EXAMPLE 96

N-(5-Isoquinolinyl)-2-((1-n-butyl)thio)decanamide

M.p. 73°–75° C. $^1$NMR (CDCl$_3$) δ9.8 (s, 1); 9.5 (m, 1); 8.6 (m, 1), 8.35 (m, 1); 7.8 (m, 1); 7.5 (m, 2); 3.5 (m, 1); 2.65 (m, 2); 2.1–1.7 (m, 18); 0.9 (m, 6). IR (CHCl$_3$) 2920, 1685, 1520, 1480 cm$^{-1}$.

EXAMPLE 97

N-(2,4,6-trimethoxyphenyl)-N'-[4-(3-methylbutyl)phenylmethyl]-N'-heptylurea 209 mg (1 mmole) 2,4,6-trimethoxyphenylisocyanate, 275 mg 4-(3-methylbutyl)benzylamine, and 10 ml methylene chloride were stirred at room temperature overnight. The reaction mixture was concentrated in vacuo. Chromatography on 100 g silica gel eluting with 1:1 hexane-ethyl acetate gave 320 mg product.

66% yield. $^1$H NMR (CDCl$_3$): δ0.81–0.96 (c) and 0.92 (d) (total 9H); 1.27 (c, 9H); 1.44–1.68 (c, 4H); 2.6 (t, 2H); 3.33 (t, 2H); 3.75 (s, 6H); 3.77 (s, 3H); 4.55 (s, 2H); 5.55 (s, 1H); 6.11 (s, 2H); 7.15 (d, 2H); 7.24 (d, 2H). IR (CHCl$_3$): 1654. cm$^{-1}$.

EXAMPLE 98

N-(2,4,6-trimethoxyphenyl)-N'-[4-(2,2-dimethylpropyl)phenylmethyl]-N-heptylurea

The title compound was prepared according to the procedure of Example 97, but using 760 mg (3.63 mmole) 2,4,6-trimethoxyphenylisocyanate, 1.0 g (3.63 mmole) 4-(2,2-dimethylpropyl)benzylamine, and 20 ml methylene chloride. There was obtained 1.25 g product.

71% yield. $^1$H NMR (CDCl$_3$): δ0.82–0.95 (c) and 0.89 (s) (total 12H); 1.27 (c, 8H); 1.61 (c, 2H); 2.48 (s, 2H); 3.34 (t, 2H); 3.76 (s, 6H); 3.78 (s, 3H); 4.57 (s, 2H); 5.59 (s, 1H); 6.12 (s, 2H); 7.1 (d, 2H); 7.23 (d, 2H). IR (CHCl$_3$): 1657 c$^{-1}$.

EXAMPLE 99

N-(6-Methylthio-8-acetaminoquinolin-5-yl)-2-(hexylthio) decanoic amide

5-Amino-6-methylthio-8-acetaminoquinoline, prepared according to the procedure of Gilman et al. (*J. Amm. Chem. Soc.* 68, 1577 (1946), was coupled with 2-hexanethiodecanoic acid (prepared as described in Example 25) using the procedure described in Example 25, to give the title compound.

$^1$H NMR (CDCl$_3$) δ9.75 (s, 1H); 8.82 (s, 1H); 8.68 (d, 5 Hz, 1H); 8.46 (s, 1H); 7.97 (d, 7 Hz, 1H); 7.41 (dd, 5 & 7 Hz, 1H); 3.50 (t, 6 Hz, 1H); 2.79 (t, 6 Hz, 2H); 2.58 (s, 3H); 2.35 (s, 3H); 2.13 (m, 1H); 1.85 (m, 1H); 1.76–1.22 (m, 20H); 0.86 (m, 6H).

$^{13}$C NMR (CDCl$_3$) δ172.1, 169.0, 147.1, 136.4, 136.1, 134.5, 131.6, 125.2, 122.3, 113.1, 59.8, 51.1, 33.1, 32.3, 31.9, 31.4, 29.4, 29.3, 28.6, 27.8, 25.1, 22.6, 22.5, 15.3, 14.1.

IR (KBr): 3240, 2920, 1640, 1650, 1530 cm$^{-1}$.

The title compounds of Examples 100–107 were prepared according to the procedure described in Example 4.

EXAMPLE 100

2-(4-t-Butylphenylthio)-N-(2,4,6-trimethoxyphenyl)octanamide

IR (CHCl$_3$): 1670 cm$^{-1}$.

EXAMPLE 101

2-(4-t-Butylphenylthio)-N-(2,4,6-trimethylphenyl)octanamide

IR (CHCl$_3$): 1670 cm$^{-1}$.

EXAMPLE 102

2-[4-(1,1-Dimethylpropyl)phenylthio)-N-(2,4,6-trimethylphenyl)nonanamide

IR (CHCl$_3$): 1670 cm$^{-1}$.

EXAMPLE 103

2-(4-n-Butylphenylthio)-N-(2,4,6-trimethylphenyl)nonanamide

IR (CHCl$_3$): 1669 cm$^{-1}$.

EXAMPLE 104

2-[4-(1,1-Dimethylpropyl)phenoxy)-N-(2,4,6-trimethoxyphenyl)octanamide

IR (CHCl$_3$): 1681 cm$^{-1}$.

EXAMPLE 105

2-[4-(1,1-Dimethylpropyl)phenoxy)-N-(2,4,6-trimethylphenyl)octanamide

IR (CHCl$_3$): 1678 cm$^{-1}$.

EXAMPLE 106

2-(4-n-Propylphenoxy)-N-(2,4,6-trimethylphenyl)decanamide

IR (CHCl$_3$): 1678 cm$^{-1}$.

EXAMPLE 107

2-(4-n-Propylphenylthio)-N-(2,4,6-trimethylphenyl)-nonanamide

IR (CHCl$_3$): 1669 cm$^{-1}$.

The title compounds of Examples 108–120 were prepared according to the procedure described in Examples 5 and 6.

EXAMPLE 108

N-(2,4,6-Trimethyl)phenyl-2-((2-methylfuryl)thio)octanamide

M.p. 73°–75° C.

EXAMPLE 109

N-(2,4,6-Trimethyl)phenyl-2-((2-benzimidazolyl)thiodecanamide

M.p. 171°–172° C.

EXAMPLE 110

N-(2,4,6-Trimethyl)phenyl-2-((2-benzothiazolyl)thio)octanamide

M.p. 103°–106° C.

EXAMPLE 111

N-(2,4,6-Trimethyl)phenyl-2-(1-hexylthio)octanamide

M.p. 69°–72° C.

EXAMPLE 112

N-(2,4,6-Trimethyl)phenyl-2-[2-(3-hydroxyl-2-pyridyl)thio]decanoamide

IR (CHCl$_3$): 3200, 2920, 1675 cm$^{-1}$.

EXAMPLE 113

N-(2,4,6-Trimethyl)phenyl-2-[2-(6-chlorobenzothiazolyl)thio)octamide

M.p. 130°–131° C.

EXAMPLE 114

N-(2,4,6-Trimethyl)phenyl-2-(1-heptylthio)octanamide

M.p. 53°–56° C.

EXAMPLE 115

N-(Isoquinolin-5-yl)-2-(1-heptylthio)decanamide

M.p. 71° C.

EXAMPLE 116

N-(2,4,6-Trimethyl)phenyl-2-(tert-butylthio)octanamide

M.p. 145°–147° C.

EXAMPLE 117

N-(Isoquinolin-5-yl)-2-(4-propylphenylthio)decanoic amide

M.p. 86°–88° C.

EXAMPLE 118

N-(Isoquinolin-5-yl)-2-(phenylmethylthio)decanoic amide

M.P. 86°–88° C.

EXAMPLE 119

N-(Isoquinolin-5-yl)-2-(cyclohexylthio)decanoic amide

M.p. 98°–100° C.

EXAMPLE 120

N-(Quinolin-5-yl)-2-(hexylthio)decanoic amide

IR (KBr) cm$^{-1}$: 3240, 2920, 2850, 1657, 1529.

The title compounds of Examples 121–122 were prepared according to the procedure described in Example 31.

EXAMPLE 121

N-(6-Methylquinolin-5-yl)-2-(hexylthio)decanoic amide

Mass spectrum m/e (relative intensity): M+428.26 (1), 312.22 (23), 213.06 (30), 200.10 (23), 158.06 (100). High resolution mass spectra: m/e 428.2843, calc'd for $C_{26}H_{40}N_2OS$: 428.2853. Anal.: Calc'd for $C_{26}H_{40}N_2OS$: C, 72.85; H, 9.41; N, 6.54. Found: C, 73.04; H, 9120; N, 6.52.

EXAMPLE 122

N-(4-Methoxycarbonyl-6-methoxyquinolin-5-yl)-2-(hexylthio)decanoic amide

IR (CHCl$_3$) cm$^{-1}$: 3320, 2915, 2862, 1748, 1651.

EXAMPLE 123

N-(Quinolin-5-yl]-2-(decyl)cyclopentane carboxamide

5-Aminoquinoline was converted to the title compound according to the procedure described in Example 30.

M.p. 75° C.

EXAMPLE 124

N-(6-Methoxyquinolin-5-yl]-2-(decyl)cyclopentanecarboxamide

6-Methoxy-5-aminoquinoline, prepared according to the procedure of Example 33, was converted to the title compound according to the procedure described in Example 30.

M.p. 57°–58° C.

EXAMPLE 125

N-(6-Methoxyquinolin-5-yl)-2-(4-sec-butylphenoxy) nonanoic amide

The title compound was prepared according to the procedure described in Example 4.

Anal: calc'd for $C_{29}H_{38}N_2O_3$: C, 75.35; H, 8.28; N, 6.06. Found: C, 74.81; H, 8.24; N, 5.96.

EXAMPLE 126

N-(6-Methoxyquinolin-5-yl]-2-octanyl-1,3-dithiane-2-carboxamide

5-Amino-6-methoxyquinoline, prepared as described in Example 60, was coupled with 2-octanyl-1,3-dithiane-2-carboxylic acid, prepared by treatment of 1,3-dithiane-2-carboxylic acid with sodium hexamethyldisilazide and octanyl bromide, according to the procedure described in Example 48 to give the title compound.

Oil. $^1H$ NMR(CDCl$_3$): δ9.00 (s, 1H); 8.63 (d, 4Hz, 1H); 7.94 (d, 10 Hz, 1H); 7.92 (d, 9 Hz, 1H); 7.73 (d, 10 Hz, 1H); 7.13 (dd, 4 & 12 Hz, 1H); 3.94 (s, 3H); 3.10 (dt, 2 & 12 Hz, 2H); 2.70 (dt, 4 & 12 Hz, 2H); 2.07 (m, 2H); 1.96 (m, 2H); 1.60 (m, 2H); 1.31–1.08 (m, 10H); 0.87 (t, 6 Hz, 3H).

The title compounds of Examples 127–131 were prepared according to the procedure described in Example 35.

EXAMPLE 127

N-(6-Cyclohexylthio) quinolin-5-yl)-2-hexylthiodecanoicamide

M.p. 88°–89° C.

EXAMPLE 128

N-(6-(3-phenylpropylthio)quinolin-5-yl)-2-hexylthiodecanoic amide

M.p. 63°–64° C.

EXAMPLE 129

N-(6-(benzylthio)quinolin-5-yl)-2-hexylthiodecanoic amide

Anal: calc'd for $C_{32}H_{44}N_2OS_2$: C, 71.48; H, 8.50; N, 5.20. Found: C, 71.59; H, 8.26; N, 5.21.

EXAMPLE 130

N-(6-(hexylthio)quinolin-5-yl]-2-hexylthiodecanoic amide

Anal: calc'd for $C_{31}H_{50}N_2OS_2$: C, 70.13; H, 9.49; N, 5.28. Found: C, 69.99; H, 9.37; N, 5.42.

EXAMPLE 131

N-(6-chloroquinolin-5-yl)-2-hexylthiodecanoic amide

Anal: calc'd for $C_{25}H_{37}ClN_2OS$: C, 66.06; H, 8.7; N, 5.42. Found: C, 66.86; H, 8.31; N, 6.24.

The title compounds of Examples 132–141 were prepared according to the procedure described in Examples 54–59.

EXAMPLE 132

Exo-3-n-nonyl-endo-N-(2,4,6-trimethylphenyl)-bicyclo-[2.2.1]hept-5-ene-2-carboxamide IR (CHCl$_3$): 1659 cm$^{-1}$.

EXAMPLE 133

Exo-3-n-heptyl-endo-N-(2,4,6-trimethylphenyl)-bicyclo-[2.2.1]hept-5-ene-2-carboxamide IR (CHCl$_3$): 1660 cm$^{-1}$.

EXAMPLE 134

Exo-3-n-octyl-endo-N-(2,4,6-trimethoxyphenyl)-bicyclo-[2.2.1]hept-5-ene-2-carboxamide IR (CHCl$_3$): 1660 cm$^{-1}$.

EXAMPLE 135

Endo-3-n-octyl-exo-N-(2,4,6-trimethoxyphenyl)-bicyclo-[2.2.1]hept-5-ene-2-carboxamide IR (CHCl$_3$): 1677 cm$^{-1}$.

EXAMPLE 136

Endo-3-n-heptyl-exo-N-(2,4,6-trimethoxyphenyl)-bicyclo-[2.2.1]hept-5-ene-2-carboxamide IR (CHCl$_3$): 1670 cm$^{-1}$.

EXAMPLE 137

Exo-3-n-heptyl-endo-N-(2,4,6-trimethoxyphenyl)-bicyclo-[2.2.1]-hept-5-ene-2-carboxamide IR (CHCl$_3$) 1660 cm$^{-1}$.

EXAMPLE 138

Exo-3-n-hept-yl-endo-N-(2,4,6-trimethoxyphenyl)-bicyclo-[2.2.2]-5-ene-2-carboxamide IR (CHCl$_3$): 1664 cm$^{-1}$.

EXAMPLE 139

Endo-3-p-heptyl-exo-N-(2,4,6-trimethoxyphenyl)-bicyclo-[2.2.2]oct-5-ene-2-carboxamide IR (CHCl$_3$): 1680 cm$^{-1}$.

EXAMPLE 140

Exo-3-n-nonyl-endo-N-(2,4,6-trimethoxyphenyl)-bicyclo-[2.2.2]oct-5-ene-2-carboxamide IR (CHCl$_3$): 1666 cm$^{-1}$.

EXAMPLE 141

Endo-3-n-nonyl-exo-N-(2,4,6-trimethoxyphenyl)-bicyclo-[2.2.2]oct-5-ene-2-carboxamide IR (CHCl$_3$): 1679 cm$^{-1}$.

EXAMPLE 142

2-p-Nonyl-N-(2,4,6-trimethylphenyl)indane-2-carboxamide

The title compound was prepared according to the procedure described in Examples 60–64.

IR (CHCl₃): 1671 cm⁻¹.

The title compounds of Examples 143–144 were prepared according to the procedure described in Examples 55–59.

EXAMPLE 143

Exo-2-n-decyl-endo-N-(2,4,6-trimethoxyphenyl)-bicyclo-[2.2.1]hept-5-ene-2-carboxamide IR (CHCl₃) 1676 cm⁻¹.

EXAMPLE 144

Endo-2-n-decyl-exo-N-(2,4,6-trimethoxyphenyl)-bicyclo-[2.2.1]hept-5-ene-2-carboxamide IR 1675 cm⁻¹.

The title compounds of Examples 145–147 were prepared according to the procedure described in Examples 60–64.

EXAMPLE 145

2-n-Octyl-2,4,6-trimethylphenyl)-1,2,3,4-tetrahydro-2-naphthamide

¹H NMR: δ0.87 (t, 3H); 1.29 (c, 10H); 1.52 (c, 3H); 1.89 (c) and 1.191 (s) (total ell); 2.2 (s, 3H); 2.3 (c, 1H); 2.91 (c) and 2.94 (d) (total 3H); 3.19 (d, 2H); 6.76 (s, 1H); 6.79 (S, 2H); 7.12 (s, 4H).

EXAMPLE 146

2-n-Decyl-N-(2,4,6-trimethylphenyl)indane-2-carboxamide

IR (CHCl₃) 1671 cm⁻¹.

EXAMPLE 147

2-n-Nonyl-N-(2,4,6-trimethylphenyl)-1,2,3,4-tetrahydro-2-naphthamide

IR (CHCl₃) 1668 cm⁻¹.

The title compounds of Examples 148–150 were prepared according to the procedure described in Examples 5 and 6.

EXAMPLE 148

N-(2,6-Difluoro)phenyl-2-((1-N-hexyl)thio)octanamide

M.p. 46°–48° C.

EXAMPLE 149

N-(2.6-Difluoro)phenyl 2-(2-(6-ethoxybenzthiazolyl)thio)octanamide

M.p. 110°–112° C.

EXAMPLE 150

N-(2,6-Difluoro)phenyl-2-(2-(6-ethoxybenzthiazolyl)thio)decanamide

M.p. 99°–100° C.

EXAMPLE 151

N-(6-acetaminoquinolin-5-yl)-2-(hexylthio)decanoic amide

Commercially available 5-amino-6-nitroquinoline was reduced to 5,6-diaminoquinoline using a procedure analogous to that described in Example 34, except tin (II) chloride was used in place of iron. 5,6-Diaminoquinoline was converted to 5-amino-6-acetaminoquinoline by reaction with acetic anhydride and pyridine. Using the procedure outlined in Example 25, 5-amino-6-acetaminoquinoline and 2-(hexylthio)decanoic acid were coupled to give the title compound. Mass spectrum m/e: 471.3 (M+).

¹H NMR, δ(CDCl₃): 8.99 (s, 1H); 8.85 (dd, J=2 & 4 Hz, 1H); 8.37 (s, 1H); 8.14 (d, J=10 Hz, 1H), 7.89 (d, J=9 Hz, 1H); 7.79 (d, J=9 Hz, 1H); 7.36 (dd, J=4 & 10 Hz, 1H); 3.47 (t, J=8 Hz, 1H); 2.64 (t, J=8 Hz, 2H); 2.13 (s, 3H): 1.87 (m, 2H); 1.28 (br m, 20H); 0.87 (m, 6H).

EXAMPLE 152

N-(6-aminoquinolin-5-yl)-2-(hexylthio)decanoic amide

N-(6-Acetaminoquinolin-5-yl)-2-(hexylthio)decanoic amide, prepared as described in Example 151, was treated with aqueous hydrochloric acid and isopropanol to give the title compound. Mass spectrum m/e: 428.3 (M+−1).

¹H NMR, δ(CDCl₃): 8.94 (d, J=6 Hz); 8.93 (d, J=2 Hz, 1H), 7.93 (d, J=9 Hz, 1H); 7.73 (d, J=9 Hz, 1H); 7.50 (dd, J=2 & 6 Hz, 1H); 4.33 (t, J=7 Hz, 1H); 2.43 (m, 2H), 2.00 (m, 2H); 1.48 (m, 4H); 1.19 (m, 16H); 0.81 (m, 6H).

EXAMPLE 153

N-(6-methylthioquinolin-5-yl)oleamide

5-Amino-6-methylthioquinoline, prepared as described in Example 34, and commercially available oleoyl chloride were coupled to give the title compound according to the procedure described in Example 25. Mass psectrum m/e: 454.3 (M+).

¹H NMR, δ(CDCl₃): 8.77 (d, J=3 Hz, 1H); 8.00 (d, J=6 Hz, 1H); 7.98 (d, J=7 Hz, 1H) 7.59 (d, J=6 Hz, 1H); 7.32 (dd, J=3 & 7 Hz, 1H); 7.14 (s, 1H); 5.32 (br s, 2H); 2.51 (s, 5H) 1.99 (br s, 4H); 1.81 (m, 2H); 1.30 (br s, 20H); 0.84 (t, J=6 Hz, 3H).

EXAMPLE 154

N-(8-amino-6-methoxyquinolin-5-yl)-2-hexylthiodecanoicamide

Commercially available 6-methoxy-8-aminoquinoline (Chemical Procurement Laboratories) was acetylated with acetic anhydride and pyridine. The resultant 6-methoxy-8-acetaminoquinoline was nitrated and reduced using the procedure described in Example 33 to give 5-amino-6-methoxy-8-acetaminoquinoline. This product was coupled with 2-(hexylthio)decanoic acid according to Example 25 and hydrolyzed with aqueous hydrochloric acid and isopropanol to give the title compound. Mass spectrum m/e: 459.3 (M+).

¹H NMR, δ(CDCl₃): 8.52 (d, J=4 Hz, 1H), 8.19 (s, 1H); 7.85 (d, J=8 Hz, 1H); 7.27 (dd, J=4 & 8 Hz, 1H); 6.60(s, 1H); 5.06 (br s, 2H); 3.82(s, 3H); 3.48 (t, J=6 Hz, 1H); 2.27 (t, J=7 Hz, 2H), 2.01 (m, 1H); 1.82 (m, 1H); 1.63 (m, 2H); 1.28 (m, 18H); 0.86 (m, 6H).

EXAMPLE 155

N-(6-(1.2.4-triazol-3-yl)thioquinolin-5-yl)-2-hexylthiodecanoic amide

Using a procedure analogous to that described in Example 34, 5-amino-6-(1,2,4-triazol-3-yl) quinoline was synthesized and coupled with 2-(hexylthio)decanoic acid to give the title compound.

Analysis: C 62.94, H 7.56, N 13.34; calc. for $C_{27}H_{39}N_5OS_2$: C 63.12, H 7.65, N 13.63.

$^1$H NMR, δ(CDCl$_3$): 9.59 (s, 1H), 8.89 (d, J=5 Hz, 1H); 8.18 (d, J=9 Hz, 1H); 8.06 (s, 1H); 7.93 (d, J=9 Hz, 1H); 7.65 (d, J=9 Hz, 1H), 7.43 (dd, J=5 & 9 Hz, 1H), 3.50 (t, J=7 Hz, 1H); 2.74 (t, J=7 Hz, 2H), 2.04 (m, 1H); 1.70 (m, 1H); 1.59 (m, 3H); 1.25 (m, 18H); 0.86 (m, 6H).

EXAMPLE 156

N-(6-methylthioquinolin-5-yl)-2,2-di(hexylthio) acetamide 2,2-Di(hexylthio) acetic acid was synthesized from dichloroacetic acid and hexanethiol using a procedure similar to that described in Example 1. 2, 2-Di(hexylthio)acetic acid and 5-amino-6-methylthioquinoline were coupled to give the title compound using the procedure described in Example 25.

Mass spectrum m/e: 464.2 (M+).

$^1$H NMR δ(CDCl$_3$): 8.83 (dd, J=3 & 4 Hz, 1H); 8.45 (s, 1H), 8.12 (d, J=8 Hz, 1H); 8.09 (d, J=8 Hz, 1H); 7.64, d, J=8 Hz, 1H); 7.42 (dd, J=4 & 8, 1H); 4.51 (s, 1H); 2.89 (t, J=8 Hz, 4H); 2.57 (s, 3H), 1.68 (m, 6H), 1.44 (m, 6H); 1.32 (m, 8H); 0.81 (t, J=7 Hz, 6H).

EXAMPLE 157

N-(6-methylthioquinolin-2-yl)-2-heptylnonanoic amide

By use of the procedures described in Example 25, nonanoic acid was alkylated with heptyl bromide and the resulting product was coupled with 5-amino-6-methylthioquinoline (Example 34) to give the title compound. Mass spectrum m/e: 428.3 (M+–SCH$_3$).

$^1$H NMR (CDCl$_3$): δ8.77 (d, J=4 Hz, 1H); 8.00 (d, J=8 Hz, 1H); 7.95 (d, J=8 Hz, 1H); 7.55 (d, J=8 Hz, 1H); 7.49 (s, 1H); 7.31 (dd, J=4 & 8 Hz, 1H); 2.49 (s, 3H); 2.43 (m, 1H); 1.40 (br, 24H); 0.85 (t, J=6 Hz, 6H).

EXAMPLE 158

N-(6-methylthioquinolin-5-yl)-2-[2-(6-ethoxybenzthiazolyl)-thio]decanoic amide.

The title compound was prepared by procedures analogous to those as described in Examples 5 and 6.

MP: 139°–141° C.

$^1$H NMR (CDCl$_3$): δ9.42 (s, 1H); 8.76 (d, 3Hz, 1H); 8.00 (d, 9 Hz, 2H); 7.74 (d, 9 Hz, 1H); 7.60 (d, 9 Hz, 1H); 7.21 (m, 2H); 6.98 (dd, 3 & 9 Hz, 1H); 4.71 (t, 7 Hz, 1H); 4.05 (q, 7 Hz, 2H); 2.53 (s, 3H); 2.30 (m, 1H); 1.97 (m, 1H); 1.59 (m, 2H); 1.45–1.25 (m, 10H); 1.00–0.81 (m, 6H).

FABMS m/e: 554 (M$^+$+1)

Anal.: Calc'd for $C_{29}H_{35}N_3O_2S_3$½ $H_2O$: C, 61.89; H, 6.45; N, 7.46. Found: C, 62.14; H, 6.33; N, 7.43.

EXAMPLE 159

N-(3-methyl-6-chloro-8-acetaminoquinolin-5-yl)-2-(hexylthio) decanoic amide

3-Methyl-5-amino-6-chloro-8-acetaminoquinoline, prepared according to the procedures of Utermohlen, W. P., J. Org. Chem., 8, 544 (1943) and Gilman et al., J. Am. Chem. Soc., 68, 1577 (1946), was coupled with 2-hexanethiodecanoic acid (prepared as described in Example 25) using the procedure described in Example 25, to give the title compound.

MP: 140°–141° C.

$^1$H NMR (CDCl$_3$): δ9.68 (s, 1H); 8.72 (s, 1H); 8.57 (s, 2H); 7.76 (s, 1H); 3.52 (t, 7 Hz, 1H); 2.75 (t, 7 Hz, 2H); 2.49 (s, 3H); 2.33 (s, 3H); 2.13–1.28 (m, 22H); 0.87 (m, 6H).

EIMS m/e: 519 (M$^+$)

Anal.: Calc'd for $C_{28}H_{42}N_3O_2SCl$; C, 64.66, H, 8.14; N, 8.07. Found: C, 64.65; H, 8.39; N, 7.96.

EXAMPLE 160

N-(3-methyl-6-methylthio-8-acetaminoquinolin-5-yl)-2-(hexylthio) decanoic amide

3-Methyl-5-amino-6-methylthio-8-acetaminoquinoline, prepared according to the procedures of Utermohlen, W. P., J. Org. Chem., 8, 544 (1943) and Gilman et al. J. Am. Chem. Soc., 68, 1577 (1946), was coupled with 2-hexanethiodecanoic acid (prepared as described in Example 25) using the procedure described in Example 25, to give the title compound.

MP: 128°–131° C.

$^1$H NMR (CDCl$_3$): δ9.75 (s, 1H); 8.76 (s, 1H); 8.54 (s, 1H); 8.38 (s, 1H); 7.74 (s, 1H); 3.52 (t, 7 Hz, 1H); 2.80 (t, 7 Hz, 2H); 2.58 (s, 3H); 2.48 (s, 3H); 2.34 (s, 3H); 2.15–1.22 (m, 22H); 0.87 (m, 6H).

EIMS m/e: 531 (M$^+$)

Anal.: Calc'd for $C_{29}H_{45}N_3O_2S_2$: C, 65.50; H, 8.53; N, 7.90. Found: C, 65.33; H, 8.55; N, 7.85.

EXAMPLE 161

N-(3-methyl-6-methylthioquinolin-5-yl)-2-(hexylthio)decanoic amide

3-Methyl-5-amino-6-methylthioquinoline, prepared according to the procedures of Utermohlen, W. P., J. Org. Chem., 8, 544 (1943) and Gilman et al., J. Am. Chem. Soc., 68, 1577 (1946), was coupled with 2-hexanethiodecanoic acid (prepared as described in Example 25) using the procedure described in Example 25, to give the title compound.

M.p.: 137°–138° C.

$^1$NMR (CDCl$_3$): δ8.69 (d, 2 Hz, 1H); 8.52 (s, 1H); 8.02 (d, 9 Hz, 1M); 7.79 (s, 1H); 7.58 (d, 9 Hz, 1H); 3.54 (t, 7 Hz, 1H); 2.81 (t, 7 Hz, 2M); 2.55 (s, 3H); 2.49 (s, 3H); 2.15–1.25 (m, 22M); 0.87 (m, 6H).

EIMS m/e: 474 (M$^+$)

Anal.: Calc'd for $C_{27}H_{42}N_2OS_2$; C, 68.31; H, 8.91; N, 5.90. Found: C, 68.52; H, 8.94; N, 5.91.

EXAMPLE 162

N-(6-nitroquinolin-5-yl)-2-(hexylthio)decanoic amide

Commercially available 5-amino-6-nitroquinoline was coupled with 2-hexanethiodecanoic acid (prepared as described in Example 25) using the procedure described in Example 25, to give the title compound.

M.p.: 89.91° C.

$^1$H NMR (CDCl$_3$): δ10.10 (s, 1H); 9.05 (dd, 2 & 4 Hz, 1H); 8.26 (d, 9 Hz, 1H); 8.24 (m, 1M); 8.09 (d, 9 Hz, 1H);

7.52 (dd, 4 & 9 Hz, 1M); 3.48 (dd, 6 & 8 Hz, 1H); 2.65 (m, 2H); 2.05 (m, 1H); 1.86 (m, 1H); 1.70–1.20 (m, 20H); 0.87 (t, 6 Hz, 6H).

FABMS m/e: 460 (M$^+$+H) Anal.: Calc'd for $C_{25}H_{37}N_3O_3S$: C, 65.33; H, 8.11; N, 9.14. Found: C, 65.42; H, 8.13; N, 9.23.

EXAMPLE 163

N-(6-N, N-dimethylaminoquinolin-5-yl)-2-(hexylthiol)decanoic amide

5-Nitro-6-chloroquinoline, prepared as described by Manske & Kulka, *Organic Reactions*, Vol. VII, 59 (1953) and Campbell et al., *J. Am. Chem. Soc.*, 68, 1559 (1946), was allowed to react with dimethylamine to yield 5-nitro-6-dimethylaminoquinoline. This material was converted to the title compound by the procedure described in Example 33.

M.p.: oil $^1$H NMR (CDCl$_3$): δ8.80 (dd, 2 & 4 Hz, 1H); 8.69 (s, 1H); 8.02 (m, 1H); 8.00 (d, 9 Hz, 1H); 7.60 (d, 9 Hz, 1H); 7.35 (dd, 4 & 9 Hz, 1H); 3.50 (t, 8 Hz, 1H); 2.77 (s, 6H); 2.73 (t, 7 Hz, 2H); 2.12 (m, 1H); 1.86 (m, 1H); 1.72–1.25 (m, 20H); 0.87 (m, 6H).

FABMS m/e: 458 (M$^+$+H)

Anal.: Calc'd for $C_{27}H_{43}NSO$: C, 70.85; H, 9.47; N, 9.18; Found: C, 70.59; H, 9.31; N, 9.10.

EXAMPLE 164

N-(6-trifluoromethylquinolin-5-yl)-2-(hexylthio)decanoic amide

5-Nitro-6-trifluoromethylquinoline, prepared as described by Manske & Kulka, *Organic Reactions*, Vol. VII, 59 (1953) and Campbell et al., *J. Am. Chem. Soc.*, 68, 1559 (1946), was converted to the title compound by the procedure described in Example 33.

M.p.: oil $^1$H NMR (CDCl$_3$): δ10.98 (s, 1H); 9.01 (d, 2 Hz, 1H); 8.96 (dd, 2 & 4 Hz, 1H); 8.26 (dd, 2 & 8 Hz, 1H); 7.83 (s, 1H); 7.57 (dd, 4 & 8 Hz, 1H); 3.52 (t, 7 Hz, 1H); 2.61 (m, 2H); 2.02 (m, 1H); 1.84 (m, 1H); 1.65–1.15 (m, 20H); 0.84 (t, 7 Hz, 3H); 0.78 (t, 7 Hz, 3H).

FABMS m/e: 483 (M$^+$+H)

Anal.: Calc'd for $C_{26}H_{37}N_2SOF_3$: C, 64.70; H, 7.73; N, 5.80; Found: C, 64.37; H, 7.81; N, 5.71.

EXAMPLE 165

N-(cinnolin-5-yl)-2-(hexylthiol)decanoic amide

The title compound was prepared by a procedure analogous to that described in Example 33.

M.p.: 54°–56° C.

$^1$H NMR (CDCl$_3$): δ9.41 (s, 1H); 9.36 (d, 6 Hz, 1H); 8.40 (d, 9 Hz, 1H); 8.33 (d, 7 Hz, 1H); 7.86 (m, 2H); 3.54 (t, 6 Hz, 1H); 2.63 (t, 7 Hz, 2H); 2.03 (m, 1H); 1.81 (m, 1H); 1.68–1.20 (m, 20H); 0.84 (m, 6H).

HRFABMS m/e: 416.2805 ($C_{24}H_{37}N_3SO+H^+$ requires 416.2738)

EXAMPLE 166

N-(cinnolin-8-yl)-2-(hexylthiol)decanoic amide

The title compound was prepared by a procedure analogous to that described in Example 33.

M.p.: oil $^1$H NMR (CDCl$_3$): δ11.10 (s, 1H); 9.34 (d, 6 Hz, 1H); 8.88 (dd, 1 & 8 Hz, 1H); 7.86 (d, 6 Hz, 1H); 7.76 (t, 8 Hz, 1H); 7.50 (dd, 1 & 8 Hz, 1H); 3.53 (t, 7 Hz, 1H); 2.62 (t, 7 Hz, 2H); 2.03 (m, 1H); 1.86 (m, 1H); 1.65–1.15 (m, 20H); 0.81 (m, 6H).

HREIMS m/e: 415.2648 ($C_{26}H_{37}N_3SO$ requires 415.2660)

EXAMPLE 167

N-(6-methylthiophthalazin-5-yl)oleic amide

5-Nitro-6-methylthiophthalazine, prepared as described by Sturrock et al., *Can. J, Chem.*, 49, 3047 (1971) and Hirsch & Orphanos, *J. Heterocyclic Chem.*, 2, 206 (1965), was reduced with tin (II) chloride and HCl to yield 5-amino-6-methylthiophthalazine. This material was coupled with commercially available oleoyl chloride to yield the title compound.

M.p.: oil $^1$H NMR (CDCl$_3$): δ9.34 (s,2H); 7.74 (d, 8 Hz, 1H); 7.73 (s, 1H); 7.66 (d, 8 Hz, 1H); 5.34 (t, 5 Hz, 2H); 2.57 (t, 8 Hz, 2H); 2.54 (s, 3H); 2.01 (m, 4H); 1.81 (m, 2H); 1.50–1.10 (m, 20H); 0.86 (t, 6 Hz, 3H).

FABMS m/e: 456 (M$^+$+1)

EXAMPLE 168

N-[2,4-bis(methylthio)pyridin-3-yl]-2-hexylthiodecanoic amide

The title compound was prepared in 13.2% yield according to the procedure of Example 4A.

$^1$H NMR (CDCl$_3$): δ0.86 (c, 6H); 1.17–1.76(c, 21H), 2.03 (m, 1H), 2.42 (s, 3H); 2.51 (s, 3H); 2.77 (t, 2H); 3.46 (t, 1H); 6.82 (d, 1H), 8.23 (s, 1H); 8.26 (d, 1H).

IR (CHCl$_3$): 2920, 2851; 1679, 1553, 1465 cm$^{-1}$.

EXAMPLE 169

N-[4,6-bis(methylthio)pyrimidin-5-yl]-2-hexylthiodecanoic amide

The title compound was prepared in 7% yield according to the procedure of Example 4.

$^1$H NMR (CDCl$_3$): δ0.87 (c, 6H); 1.2–1.85 (c, 21H); 2.02 (m, 1H); 2.52 (s, 6H); 2.74 (t, 2H); 3.45 (t, 1H); 8.18 (s, 1H); 8.65 (s, 1H).

IR (CHCl$_3$): 2923, 2852, 1681, 1521, 1466, 1406, 1357 cm$^{-1}$.

EXAMPLE 170

N-(6-methoxyisoquinolin-5-yl)-2-hexylthiodecanoic amide

The title compound was prepared in 62% yield according to the procedure of Example 4.

$^1$H NMR (CDCl$_3$): δ0.89 (c, 6H); 1.20–1.96 (c, 21H); 2.07 (m, 1H); 2.75 (t, 2H); 3.55 (t, 1H); 4.0 (s, 3H); 7.39 (d, 1H); 7.48 (d, 1H); 7.94 (d, 1H); 8.45 (d, 1H); 8.52 (s, 1H); 9.14 (s, 1H).

IR (CHCl$_3$): 2922, 2852, 1674, 1624, 1465, 1380, 1323, 1267 cm$^{-1}$.

EXAMPLE 171

N-(6-methoxyquinazolin-5-yl)-2-hexylthiodecanoic amide

The title compound was prepared in 15% yield according to the procedure of Example 4.

¹H NMR (CDCl₃): δ0.88 (c, 6H); 1.18–1.94 (c, 21H); 2.08 (m, 1H); 2.71 (t, 2H); 3.55 (t, 1H); 4.0 (s, 3H); 7.69 (d, 1H); 8.0 (d, 1H); 8.78 (s, 1H); 9.21 (s, 1H); 9.31 (s, 1H).

IR (CHCl₃): 2923, 2852, 1682, 1621, 1573, 1496, 1476, 1465, 1372, 1319, 1273, 1255, 1222 cm⁻¹.

EXAMPLE 172

N-(4,6-dimethoxypyrimidin-5-yl)-2-hexylthiodecanoic amide

The title compound was prepared in 40% yield according to the procedure of Example 4.

¹H NMR (CDCl₃): δ0.88 (c, 6H); 1.22–2.0 (c, 22H); 2.64 (m, 1H); 3.43 (t, 1H); 3.97 (s, 6H); 7.90 (s, 1H); 8.33 (s, 1H).

IR (CHCl₃): 2922, 2852, 1680, 1582, 1491, 1465, 1410, 1399, 1312 cm⁻¹.

EXAMPLE 173

N-(4,6-diethoxypyrimidin-5-yl)-2-hexylthiodecanoic amide

The title compound was prepared in 76% yield according to the procedure of Example 4A.

¹H NMR (CDCl₃): δ0.87 (c, 6H); 1.19–1.70 (c, 27H); 1.82 (m, 1H); 2.64 (m, 2H); 3.45 (t, 1H); 4.39 (q, 4H); 7.89 (s, 1H); 8.28 (s, 1H).

IR (CHCl₃): 2924, 2853, 1681, 1582, 1491, 1441, 1386, 1315 cm⁻¹.

EXAMPLE 174

N-[4-methoxy-6-(4-methoxyphenylthio)pyrimidin-5-yl]-2-hexylthiodecanoic amide

The title compound was prepared in 6% yield according to the procedure of Example 4A.

¹H NMR (CDCl₃): δ0.87 (m, 6H), 1.17–2.04 (c, 22H); 2.72 (t, 2H); 3.50 (t, 1H); 3.83 (s, 3H); 3.96 (s, 3H); 6.94 (d, 2H); 7.44 (d, 2H); 8.17 (s, 1H); 8.37 (s, 1H).

IR (CHCl₃): 2900, 2840, 1700, 1600, 1565, 1480.

EXAMPLE 175

N-[4,6-bis(ethylthio)pyrimidin-5-yl)-2-hexylthiodecanoic amide

The title compound was prepared in 8% yield according to the procedure of Example 4B.

¹H NMR (CDCl₃): δ0.87 (m, 6H); 1.17–2.06 (c, 28H); 2.62 (m, 4H); 2.75 (t, 2H); 3.45 (t, 1H); 8.15 (s, 1H); 8.61 (s, 1H).

IR (CHCl₃): 2922, 2852, 1706, 1520, 1466, 1405, 1355 cm⁻¹.

EXAMPLE 176

N-[4-methoxy-6-(2-ethoxyethylthio)pyrimidin-5-yl)-2-hexylthiodecanoic amide

The title compound was prepared in 38% yield according to the procedure of Example 4A.

¹H NMR (CDCl₃): δ0.87 (m, 6H); 1.16–1.85 (c) and 1.19 (t) (total 24H); 1.94 (m, 1H); 2.68 (t, 2H); 3.32–3.57 (c), 3.52 (q) (total 5H); 3.65 (t, 2H), 3.95 (s, 3H); 8.03 (s, 1H); 8.47 (s, 1H).

IR (CHCl₃): 2952, 2925, 2854, 1684, 1562, 1541, 1481, 1408, 1385 cm⁻¹.

EXAMPLE 177

N-[2-(4-pyridinylthio)-4-methylpyridin-3-yl)-2-hexylthiodecanoic amide

The title compound was prepared in 10% yield according to the procedure of Example 4.

¹H NMR (CDCl₃): δ0.86 (m, 6H); 1.17–1.84 (c, 21H); 1.95 (m, 1H); 2.30 (s, 3H); 2.62 (t, 2H); 3.4 (t, 1H); 7.17 (d, 1H); 7.27 (m, 2H); 8.31 (d, 1H); 8.48 (b, 2H); 8.55 (s, 1H).

IR (CHCl₃): 2921, 2851, 1680, 1574, 1471 cm⁻¹.

EXAMPLE 178

N-[4-methoxy-6-(1-methyl-5-tetrazolythio)pyrimidin-5-yl)-2-hexylthiodecanoic amide The title compound was prepared in 43% yield according to the procedure of Example 4A.

¹NMR (CDCl₃): δ0.87 (m, 6H); 1.18–1.87 (c, 21H); 1.98 (m, 1H); 2.65 (t, 2H); 3.49 (t, 1H); 4.02 (s, 3H); 4.12 (s, 3H); 8.26 (s, 1H); 8.58 (s, 1H).

IR (CHCl₃): 2900, 2840, 1690, 1560, 1485 cm⁻¹.

EXAMPLE 179

N-[2-(2-furylmethylthio)-4-methylpyridin-3-yl)-2-hexylthiodecanoic amide

The title compound was prepared in 10% yield according to the procedure of Example 4B.

¹H NMR (CDCl₃): δ0.87 (m, 6H); 1.17–2.03 (c, 22H); 2.19 (s, 3H), 2.65 (m, 2H); 3.42 (t, 1H); 4.47 (s, 2H); 6.24 (m, 2H); 6.92 (d, 1H); 7.30 (d, 1H); 8.18 (s, 1H); 8.25 (d, 1H).

IR (CHCl₃): 2920, 2850, 1706, 1675, 1481 cm⁻¹.

EXAMPLE 180

N-[2,4,6-tris(methylthio)pyrimidin-5-yl)-2-hexylthiodecanoic amide

The title compound was prepared in 79% yield according to the procedure of Example 4A.

¹H NMR (CDCl₃): δ0.87 (C, 6H); 1.17–1.86 (C, 21H); 2.01 (m, 1H); 2.50 (s, 6H); 2.56 (s, 3H); 2.73 (t, 2H); 3.43 (t, 1H); 8.06 (s, 1H).

IR (CHCl₃): 2922, 2852, 1686, 1499, 1465, 1347 cm⁻¹.

EXAMPLE 181

N-(2,4,6-trimethoxypyrimidin-5-yl)-2-hexylthiodecanoicamide

The title compound was prepared in 74% yield according to the procedure of Example 4A.

¹H NMR (CDCl₃): 0.87 (m, 6H); 1.18–2.0 (C, 22H); 2.63 (m, 2H); 3.42 (t, 1H); 3.93 (s, 6H); 3.95 (s, 3H); 7.71 (s, 1H).

IR (CHCl₃): 2923, 2851, 1675, 1607, 1582, 1482, 1467, 1398, 1379 cm⁻¹.

EXAMPLE 182

N-[2-methyl-4,6-bis(ethylthio)pyrimidin-5-yl]-2-hexylthiodecanoic amide

The title compound was prepared in 52% yield according to the procedure of Example 4A.

¹H NMR (CDCl₃): δ0.87 (m, 6H); 1.19–1.84 (c, 27H); 2.0 (m, 1H); 2.57 (s, 3H); 2.75 (t, 2H); 3.15 (q, 4H); 3.44 (t, 1H); 8.04 (s, 1H).

IR (CHCl$_3$): 2920, 2852, 1680, 1467, 1406, 1359, 1314 cm$^{-1}$.

EXAMPLE 183

N-(6-methoxyquinolin-5-yl)-2-heptylnonanoic amide

The title compound was prepared in 20% yield according to the procedure of Example 4.

$^1$H NMR (CDCl$_3$): δ0.88 (m, 6H); 1.18–1.84 (c, 24H); 2.41 (m, 1H); 3.97 (s, 3H); 7.13 (s, 1H); 7.36 (q, 1H); 7.5 (d, 1H); 8.04 (t, 2H); 8.78 (m, 1H).

IR (CHCl$_3$): 2921, 2850, 1686, 1596, 1570, 1465, 1322, 1266 cm$^{-1}$.

EXAMPLE 184

N-(2,4,6-trimethoxyphenyl)-2-heptylnonanoic amide

The title compound was prepared in 72% yield according to the procedure of Example 4.

$^1$H NMR (CDCl$_3$): δ0.88 (m, 6H); 1.18–1.8 (c, 24H); 2.2 (m, 1H); 3.77 (s, 6H); 3.79 (s, 3H); 6.13 (s, 2H); 6.38 (s, 1H).

IR (CHCl$_3$): 2921, 2850, 1677, 1598, 1505, 1465, 1437, 1413, 1153, 1131 cm$^{-1}$.

EXAMPLE 185

N-(6-methoxyisoquinolin-5-yl)-2-heptylnonanoic amide

The title compound was prepared in 21% yield according to the procedure of Example 4.

$^1$H NMR (CDCl$_3$): δ0.88 (m, 6H); 1.18–1.85 (c, 24H); 2.41 (m, 1H); 3.98 (s, 3H); 7.09 (s, 1H); 7.37 (d, 1H); 7.52 (b, 1H); 7.91 (d, 1H); 8.44 (b, 1H); 9.13 (b, 1H).

IR (CHCl$_3$): 2922, 2850, 1685, 1625, 1465, 1381, 1324, 1279, 1268 cm$^{-1}$.

EXAMPLE 186

N-(4,6-dimethoxypyrimidin-5-yl)-2-heptylnonanoic amide

The title compound was prepared in 53% yield according to the procedure of Example 4.

$^1$H NMR (CDCl$_3$): δ0.87 (m, 6H); 1.18–1.8 (c, 24H); 2.24 (m, 1H); 3.97 (s, 6H); 8.32 (s, 1H).

IR (CHCl$_3$): 2921, 2851, 1686, 1583, 1487, 1463, 1408, 1400, 1312, 1121 cm$^{-1}$.

EXAMPLE 187

N-[2,4-bis(methylthio)-6-methylpyridin-3-yl]-2-heptylnonanoic amide

The title compound was prepared in 48% yield according to the procedure of Example 4B.

$^1$H NMR (CDCl$_3$): δ0.87 (m, 6H); 1.17–1.82 (c, 24H); 2.28 (m, 1H); 2.4 (s, 3H); 2.48 (s, 3H); 2.50 (s, 3H); 6.53 (s, 1H); 6.63 (s, 1H).

IR (CHCl$_3$): 2921, 2851, 1686, 1560, 1460, 1338 cm$^{-1}$.

EXAMPLE 188

N-[2-methyl-4,6-bis(methylthio)pyrimidin-5-yl]-2-heptylnonanoic amide

The title compound was prepared in 35% yield according to the procedure of Example 4A.

$^1$H NMR (CDCl$_3$): δ0.87 (m, 6H); 1.18–1.8 (c, 24H); 2.27 (m, 1H); 2.49 (s, 6H); 2.59 (s, 3H); 6.46 (s, 1H).

IR (CHCl$_3$): 2920, 2850, 1691, 1505, 1462, 1431, 1406, 1360, 1300 cm$^{-1}$.

EXAMPLE 189

N-[2,4-bis(methylthio)-6-methylpyridin-3-yl]-2,2-dimethyldodecanoic amide

The title compound was prepared in 49% yield according to the procedure of Example 4B.

$^1$H NMR (CDCl$_3$): δ0.87 (t, 3H); 1.18–1.67 (c) and 1.32 (s) (total 24H); 2.39 (s, 3H); 2.48 (s, 3H); 2.50 (s, 3H); 6.63 (s, 1H); 6.72 (s, 1H).

IR (CHCl$_3$): 2920, 2850, 1678, 1559, 1459, 1338 cm$^{-1}$.

EXAMPLE 190

N-[2,4-bis(methylthio)pyridin-3-yl]-2,2-dimethyldodecanoic amide

The title compound was prepared in 40% yield according to the procedure of Example 4B.

$^1$H NMR (CDCl$_3$): δ0.87 (t, 3H); 1.2–1.68 (c) and 1.33 (s) (total 24H); 2.41 (s, 3H); 2.51 (s, 3H); 6.79 (s, 1H); 6.82 (d, 1H); 8.25 (d, 1H).

IR (CHCl$_3$): 2920, 2850, 1679, 1553, 1462, 1370 cm$^{-1}$.

EXAMPLE 191

N-[2-methyl-4,6-bis(methylthio)pyrimidin-5-yl]-2,2-dimethyldodecanoic amide

The title compound was prepared in 23% yield according to the procedure of Example 4A.

$^1$NMR (CDCl$_3$): δ0.86 (t, 3H); 1.2–1.68 (c) and 1.31 (s) (total 24H); 2.49 (s, 6H); 2.59 (s, 3H); 6.65 (s, 1H).

IR (CHCl$_3$): 2923, 2849, 1683, 1510, 1467, 1407, 1362, 1301 cm$^{-1}$.

EXAMPLE 192

N-[4,6-bis(methylthio)pyrimidin-5-yl]-2,2-dimethyldodecanoic amide

The title compound was prepared in 43% yield according to the procedure of Example 4A.

$^1$H NMR (CDCl$_3$): δ0.86 (t, 3H); 1.2–1.68 (c) and 1.32 (s) (total 24H); 2.51 (s, 6H); 6.74 (s, 1H); 8.64 (s, 1H).

IR (CHCl$_3$): 2924, 2851, 1688, 1522, 1468, 1406, 1359 cm$^{-1}$.

EXAMPLE 193

N-(6-methylthioquinolin-5-yl)-2,2-dimethyldodecanoic amide

The title compound was prepared in 4% yield according to the procedure of Example 4B.

$^1$H NMR (CDCl$_3$): δ0.86 (t, 3H); 1.2–1.78 (c) and 1.42 (s) (total 24H); 2.55 (s, 3H); 7.44 (m, 2H); 7.66 (d, 1H); 8.07 (d, 1H); 8.13 (d, 1H); 8.83 (m, 1H).

IR (CHCl$_3$): 2921, 2851, 1677, 1565, 1463, 1375 cm$^{-1}$.

EXAMPLE 194

N-[2,4-bis(ethylthio)-6-methylpyridin-3-yl]-tetradecanoic amide

The title compound was prepared in 68% yield according to the procedure of Example 4B.

¹H NMR (CDCl₃): δ0.87 (t, 3H); 1.19–1.62 (c, 26H); 1.76 (m, 2H); 2.39 (t, 2H); 2.46 (s, 3H); 2.91 (q, 2H); 3.15 (q, 2H); 6.52 (s, 1H), 6.68 (s, 1H).

IR (CHCl₃): 2920, 2850, 1687, 1556, 1460 cm⁻¹.

EXAMPLE 195

N-[2,4-bis(methylthio)-6-methylpyridin-3-yl)-tetradecanoic amide

The title compound was prepared in 59% yield according to the procedure of Example 4B.

¹H NMR (CDCl₃): δ0.87 (t, 3H); 1.18–1.82 (c, 22H); 2.40 (s), 2.48 (s), 2.50 (s) and 2.37–2.6 (m)(total 11H); 6.50 (s, 1H); 6.64 (s, 1H).

IR (CHCl₃): 2917, 2847, 1693, 1570, 1472 cm⁻¹.

EXAMPLE 196

N-[4,6-bis(methylthio)pyrimidin-5-yl)-tetradecanoic amide

The title compound was prepared in 76% yield according to the procedure of Example 4A.

¹H NMR (CDCl₃): δ0.87 (t, 3H); 1.2–1.62 (c, 20H); 1.76 (m, 2H); 2.41 (t, 2H); 2.52 (s, 6H); 6.51 (s, 1H); 8.65 (s, 1H).

IR (CHCl₃): 2917, 2847, 1690, 1511, 1459, 1405, 1355 cm⁻¹.

EXAMPLE 197

N-[2-methyl-4,6-bis(methylthio)pyrimidin-5-yl] tetradecanoic amide

The title compound was prepared in 78% yield according to the procedure of Example 4A.

¹H NMR (CDCl₃): δ0.87 (t, 3H); 1.19–1.61 (c, 20H); 1.75 (m, 2H); 2.40 (t, 2H); 2.49 (s, 6H); 2.59 (s, 3H); 6.45 (s, 1H).

IR (CHCl₃): 2917, 2847, 1689, 1460, 1406, 1357 cm⁻¹.

EXAMPLE 198

N-(6-methylthioquinolin-5-yl)tetradecanoic amide

The title compound was prepared on 31% yield according to the procedure of Example 4B.

¹H NMR (CDCl₃): δ0.87 (t, 3H); 1.2–1.6 (c, 20H); 1.84 (m, 2H); 2.54 (s) and 2.55 (t) (total 5H); 7.18 (s, 1H); 7.40 (m, 1H); 7.64 (d, 1H); 8.06 (m, 2H); 8.84 (b, 1H).

IR (CHCl₃): 2919, 2849, 1683, 1565, 1464, 1377 cm⁻¹.

EXAMPLE 199

N-[2-methyl-4,6-bis(methylthio)pyrimidin-5-yl] pentadecanoic amide

The title compound was prepared in 53% yield according to the procedure of Example 4A.

¹H NMR (CDCl₃): δ0.87 (t, 3H); 1.18–1.81 (c, 24H), 2.4 (t, 2H); 2.5 (s, 6H), 2.6 (s, 3H); 6.44 (s, 1H).

IR (CHCl₃): 2918, 2847, 1689, 1460, 1425, 1405 cm⁻¹.

EXAMPLE 200

N-[2,4-bis(methylthio)-6-methylpyridin-3-yl] pentadecanoic amide

The title compound was prepared in 68% yield according to the procedure of Example 4B.

¹H NMR (CDCl₃): δ0.87 (t, 3H); 1.18–1.82 (c, 24H); 2.40 (s+t, 5H); 2.51 (s, 3H); 6.52 (s, 1H); 6.63 (s, 1H).

IR (CHCl₃): 2921, 2849, 1686, 1612, 1559, 1459 cm⁻¹.

EXAMPLE 201

N-[2-methyl-4,6-bis(methylthio)pyrimidin-5-yl] hexadecanoic amide

The title compound was prepared in 78.2% yield according to the procedure of Example 4A.

¹H NMR (CDCl₃): δ0.87 (t, 3H); 1.18–1.49 (c, 22H), 1.57 (m, 2H); 1.75 (m, 2H); 2.39 (t, 2H); 2.49 (s, 6H); 2.59 (s, 3H); 6.46 (s, 1H).

IR (CHCl₃): 2919, 2849, 1688, 1459, 1406, 1358 cm⁻¹.

EXAMPLE 202

N-[4,6-bis(ethylthio)pyrimidin-5-yl)hexadecanoic amide

The title compound was prepared in 70% yield according to the procedure of Example 4A.

¹H NMR (CDCl₃): δ0.87 (t, 3H); 1.18–1.5 (c, 28H); 1.58 (m, 2H); 1.76 (m, 2H); 2.4 (t, 2H); 3.15 (q, 4H); 6.49 (s, 1H); 8.61 (s, 1H).

IR (CHCl₃): 2918, 2848, 1692, 1460, 1404, 1356 cm⁻¹.

EXAMPLE 203

N-[2,4-bis(methylthio)-6-methylpyridin-3-yl] hexadecanoic amide

The title compound was prepared in 8.6% yield according to the procedure of Example 4.

¹H NMR (CDCl₃): δ0.87 (t, 3H); 1.18–1.84 (c, 26H); 2.39 (s+t, 5H); 2.48 (s, 3H); 2.5 (s, 3H); 6.5 (s, 1H); 6.64 (s, 1H).

IR (CHCl₃): 2921, 2849, 1690, 1612, 1560, 1460 cm⁻¹.

EXAMPLE 204

N-[4,6-bis(methylthio)pyrimidin-5-yl]hexadecanoic amide

The title compound was prepared in 58.8% yield according to the procedure of Example 4A.

¹H NMR (CDCl₃): δ0.87 (t, 3H); 1.18–1.49 (c, 22H); 1.57 (m, 2H); 1.76 (m, 2H); 2.41 (t, 2H); 2.51 (s, 6H); 6.54 (s, 1H); 8.65 (s, 1H).

IR (CHCl₃): 2920, 2849, 1696, 1521, 1465, 1407, 1358 cm⁻¹.

EXAMPLE 205

N-[4,6-bis(methylthio)pyrimidin-5-yl)-(Z)-9-octadecenoic amide

The title compound was prepared in 61% yield according to the procedure of Example 4A.

¹H NMR (CDCl₃): δ0.86 (t, 3H); 1.17–1.5 (c, 18H); 1.59 (m, 2H); 1.76 (m, 2H); 2.0 (c, 4H); 2.41 (t, 2H); 2.51 (s, 6H); 5.34 (m, 2H); 6.56 (s, 1H); 8.65 (s, 1H).

IR (CHCl₃): 2920, 2850, 1693, 1515, 1465, 1407, 1358 cm⁻¹.

EXAMPLE 206

N-[2,4-bis(methylthio)-6-methylpyridin-3-yl]-(Z)-9-octadecenoic amide

The title compound was prepared in 55% yield according to the procedure of Example 4.

¹H NMR (CDCl₃): δ0.87 (t, 3H); 1.18–1.68 (c, 20H); 1.77 (m, 2H); 2.0 (c, 4H); 2.39 (s+t, 5H); 2.47 (s, 3H); 2.49 (s, 3H); 5.34 (m, 2H); 6.51 (s, 1H); 6.63 (s, 1H).

IR (CHCl₃): 2918, 2850, 1686, 1560, 1460, 1339 cm⁻¹.

EXAMPLE 207

N-[4,6-bis(ethylthio)pyrimidin-5-yl]-(Z)-9-octadecenoic amide

The title compound was prepared in 52.3% yield according to the procedure of Example 4A.

¹H NMR (CDCl₃): δ0.87 (t, 3H); 1.19–1.5 (c, 24H); 1.58 (m, 2H); 1.76 (m, 2H); 2.01 (c, 4H); 2.40 (t, 2H); 3.15 (q, 4H); 5.34 (m, 2H); 6.5 (s, 1H); 8.61 (s, 1H).

IR (CHCl₃): 2920, 2850, 1691, 1508, 1460, 1405, 1355 cm⁻¹.

EXAMPLE 208

N-[2-methyl-4,6-bis(ethylthio)pyrimidin-5-yl]-(Z)-9-octadecenoic amide

The title compound was prepared in 66.7% yield according to the procedure of Example 4A.

¹H NMR (CDCl₃): δ0.87 (t, 3H); 1.18–1.5 (c, 24H); 1.58 (m, 2H); 1.75 (m, 2H); 2.01 (c, 4H); 2.38(t, 2H); 2.57 (s, 3H), 3.14 (q, 4H); 5.34 (m, 2H); 6.41 (s, 1H).

IR (CHCl₃): 2919, 2849, 1690, 1459, 1407, 1357, 1312 cm⁻¹.

EXAMPLE 209

N-[2(methyl-4,6-bis(methylthio)pyrimidin-5-yl]-(Z)-9-octadecenoic amide

The title compound was prepared in 55% yield according to the procedure of Example 4.

¹H NMR (CDCl₃): δ0.87 (t, 3H); 1.18–1.48 (c, 18H); 1.58 (m, 2H); 1.76 (m, 2H); 2.0 (c, 4H); 2.39 (t, 2H); 2.49 (s, 6H); 2.59 (s, 3H); 5.33 (m, 2H); 6.46 (s, 1H).

IR (CHCl₃): 2923, 2850, 1692, 1508, 1464, 1429, 1406, 1360 cm⁻¹.

EXAMPLE 210

N-[2,4-bis(methylthio)pyridin-3-yl]-(Z)-9-octadecenoicamide

The title compound was prepared in 43% yield according to the procedure of Example 4A.

¹H NMR (CDCl₃): δ0.86 (t, 3H); 1.18–1.5 (c, 18H); 1.59 (m, 2H); 1.77 (m, 2H); 2.01 (c, 4H); 2.41 (s+t, 5H); 2.51 (s, 3H); 5.34 (m, 2H), 6.57 (s, 1H); 6.82 (d, 1H); 8.25 (d, 1H).

IR (CHCl₃): 2920, 2850, 1687, 1552, 1461, 1375 cm⁻¹.

EXAMPLE 211

N-[4,6-bis(methylthio)pyrimidin-5-yl]-2-dodecylthioacetamide

The title compound was prepared in 61% yield according to the procedure of Example 4A.

¹H NMR (CDCl₃): δ0.87 (t, 3H); 1.22–1.49 (c, 18H); 1.67 (m, 2H); 2.53 (s, 6H); 2.74 (t, 2H); 3.41 (s, 2H); 8.3 (s, 1H); 8.67 (s, 1H).

IR (CHCl₃): 2917, 2847, 1688, 1467, 1405, 1355 cm⁻¹.

EXAMPLE 212

N-[4,6-bis(ethylthio)pyrimidin-5-yl]-2-dodecylthioacetamide

The title compound was prepared in 52% yield according to the procedure of Example 4A.

¹H NMR (CDCl₃): δ0.87 (t, 3H); 1.22–1.5 (c, 24H); 1.67 (m, 2H); 2.74 (t, 2H); 3.17 (q, 4H); 3.41 (s, 2H); 8.27 (s, 1H); 8.63 (s, 1H).

IR (CHCl₃): 2918, 2848, 1687, 1466, 1404, 1353 cm⁻¹.

EXAMPLE 213

N-[2,4-bis(methylthio)-6-methylpyridin-3-yl]-2-dodecylthioacetamide

The title compound was prepared in 45% yield according to the procedure of Example 4.

¹NMR (CDCl₃): δ0.87 (t, 3H); 1.18–1.46 (c, 18H); 1.67 (m, 2H); 2.41 (s, 3H); 2.49 (s, 3H); 2.51 (s, 3H); 2.76 (t, 2H); 3.41 (s, 2H); 6.66 (s, 1H); 8.25 (s, 1H).

IR(CHCl₃): 2918, 2848, 1678, 1561, 1476, 1337 cm⁻¹.

EXAMPLE 214

N-[2,4-bis(methylthio)pyridin-3-yl]-2-dodecylthioacetamide

The title compound was prepared in 24% yield according to the procedure of Example 4B.

¹H NMR (CDCl₃): δ0.87 (t, 3H); 1.17–1.48 (c, 18H); 1.67 (m, 2H); 2.43 (s, 3H); 2.53 (s, 3H); 2.76 (t, 2H); 3.42 (s, 2H); 6.85 (d, 1H); 8.28 (d, 1H); 8.34 (s, 1H).

IR (CHCl₃): 2919, 2849, 1683, 1553, 1475, 1432, 1376 cm⁻¹.

EXAMPLE 215

N-[2,4-bis(ethylthio)-6-methylpyridin-3-yl)-2-dodecylthioacetamide

The title compound was prepared in 37% yield according to the procedure of Example 4B.

¹H NMR (CDCl₃): δ0.87 (t, 3H); 1.18–1.47 (c, 24H); 1.67 (m, 2H); 2.47 (s, 3H); 2.77 (t, 2H); 2.92 (q, 2H); 3.15 (q, 2H); 3.41 (s, 2H); 6.69 (s, 1H); 8.24 (s, 1H).

IR (CHCl₃): 2920, 2850, 1680, 1559, 1474, 1337 cm⁻¹.

EXAMPLE 216

N-[2,4-bis(ethylthio)pyridin-3-yl]-2-dodecylthioacetamide

The title compound was prepared in 27% yield according to the procedure of Example 4B.

¹H NMR (CDCl₃): δ0.87 (t, 3H); 1.18–1.47 (c, 24H); 1.67 (m, 2H); 2.77 (t, 2H); 2.95 (q, 2H); 3.18 (q, 2H); 3.42 (s, 2H); 6.88 (d, 1H); 8.25 (d, 1H); 8.34 (s, 1H).

IR (CHCl₃): 2920, 2850, 1682, 1551, 1474, 1375 cm⁻¹.

EXAMPLE 217

N-[2-methyl-4,6-bis(methylthio)pyrimidin-5-yl]-trans-3-nonyl1,2,3,4-tetrahydro-2-naphthoic amide The title compound was prepared in 7% yield according to the procedure of Example 4A. ¹H NMR (CDCl₃): δ0.87 (m, 3H); 1.2–1.72 (c, 16H); 2.16 (m, 1H); 2.41–2.64 (c), 2.51 (s), 2.60 (s) (total 11H); 2.94–3.28 (c, 3H); 6.54 (s, 1H); 7.12 (c, 4H).

IR (CHCl₃): 2900, 2830, 1690, 1460 cm⁻¹.

EXAMPLE 218

N-[4,6-bis(methylthio)pyrimidin-5-yl]-3-nonyl-1,2,3,4-tetrahydro-2-naphthoic amide The title compound was prepared in 8% yield according to the procedure of Example 4A.

¹H NMR (CDCl₃): δ0.87 (m, 3H); 1.18–1.75 (c, 16H); 2.17 (m, 1H); 2.4–2.62 (c), 2.53 (s) (total 8H); 2.93–3.27 (c, 3H); 6.6 (s, 1H); 7.13 (c, 4H); 8.66 (s, 1H).

IR (CHCl₃): 2900, 2830, 1700, 1610, 1470 cm⁻¹.

EXAMPLE 219

N-(2,4,6-trifluorophenyl)-trans-2-nonyl-1,2,3,4-tetrahydro-3-naphthoic amide

The title compound was prepared in 15% yield according to the procedure of Example 4A.

¹H NMR (CDCl₃): δ0.87 (m, 3H); 1.2–1.74 (c, 16H); 2.14 (m, 1H); 2.5 (m, 2H); 2.92–3.25 (c, 3H); 6.73 (m, 3H); 7.11 (m, 2H).

IR (CHCl₃): 2918, 2850, 1697, 1641, 1608, 1507, 1466, 1445 cm⁻¹.

EXAMPLE 220

N-(6-methylthioquinolin-5-yl)-2-nonyl-1,2,3,4-tetrahydro-2-naphthoic amide

The title compound was prepared in 3% yield according to the procedure of Example 4.

¹H NMR (CDCl₃): δ0.87 (t, 3H); 1.16–2.06 (c, 17H); 2.38 (m, 1H); 2.47 (s, 3H); 2.85–3.15 (c, 3H); 3.35 (d, 1H); 7.18 (m, 5H); 7.37 (s, 1H); 7.47 (d, 1H); 7.59 (d, 1H), 7.99 (d, 1H); 8.77 (s, 1H).

EXAMPLE 221

N-[4,6-bis(methylthio)pyrimidin-5-yl]-2-nonyl-1,2,3,4-tetrahydro-2-naphthoic amide The title compound was prepared in 11% yield according to the procedure of Example 4A.

¹H NMR (CDCl₃): δ0.86 (t, 3H); 1.18–1.67 (c, 15H); 1.91 (m, 2H); 2.24 (m, 1H); 2.45 (s, 6H); 2.78–2.96 (c, 21()); 3.07 (m, 1H); 3.28 (d, 1H); 6.74 (s, 1H); 7.13 (s, 4H); 8.60 (s, 1H).

IR (CHCl₃): 2921, 2849, 1681, 1518, 1454, 1406, 1357 cm⁻¹.

EXAMPLE 222

N'-[2,4-bis(methylthio)-6-methylpyridin-3-yl]-N-[4-(3-methylbutyl)benzyl]-N-cycloheptylurea A. 2,4-bis(methylthio)-6-methylpyridin-3-yl isocyanate A solution of 800 mg (4 mmol) 2,4-bis(methylthio)-3-amino-6-methylpyridine and 0.4 ml (2.3 mmol) trichloromethyl chloroformate in 20 ml anhydrous dioxane was refluxed under nitrogen overnight. The reaction mixture was cooled and filtered and the filtrate was concentrated to dryness in vacuo yielding 730 mg of the title compound (81% yield) as a tan colored solid.

B. N'-[2,4-bis(methylthio)-6-methylpyridin-3-yl]-N-[4-(3-methylbutyl)benzyl]-N-cycloheptylurea A solution of 135 mg (0.6 mmol) isocyanate from Example 225A and 164 mg (0.6 mmol) N-cycloheptyl-[4-(3-methylbutyl) benzylamine in 15 ml methylene chloride was refluxed under nitrogen overnight. The reaction mixture was cooled to room temperature and concentrated in vacuo. The residue was chromatographed on 200 g silica gel, eluting with 7:3 hexane/ethyl acetate to yield 140 mg (32% yield) of the title compound as an off-white solid.

¹H NMR (CDCl₃): δ0.92 (d, 6H); 1.39–1.74 (c, 13H); 1.98 (m, 2H); 2.37 (s, 3H); 2.44 (s, 6H); 2.59 (t, 2H); 4.37 (m, 1H); 4.50 (s, 2H); 5.47 (s, 1H); 6.57 (s, 1H); 7.18 (d, 2H); 7.32 (d, 2H).

IR (CHCl₃): 2921, 2853, 1650, 1560, 1469.

The title compounds of Examples 223–227 were prepared according to the procedure of Example 222.

EXAMPLE 223

N'[2,4-bis(methylthio)-6-methylpyridin-3-yl]-N-[4-(2,2-dimethylpropyl)benzyl]-N-cycloheptylurea 70% yield ¹H NMR (CDCl₃): δ0.88 (s, 9H); 1.39–1.74 (c, 10H); 1.99 (m, 2H); 2.33 (s, 3H); 2.44 (2s, 6H); 2.48 (s, 2H); 4.38 (m, 1H); 4.52 (s, 2H); 5.46 (s, 1H); 6.57 (s, 1H); 7.13 (d, 2H); 7.31 (d, 2H).

IR (CHCl₃): 2922, 2853, 1651, 1561, 1470 cm⁻¹.

EXAMPLE 224

N'-[2-methyl-4,6-bis(methylthio)pyrimidin-5-yl]-N-[4-(3-methylbutyl)benzyl]-N-cycloheptylurea 72% yield.

¹H NMR (CDCl₃): δ0.92 (d, 6H); 1.40–1.75 (c, 13H), 1.98 (m, 2H); 2.44 (s, 6H); 2.55 (s, 3H); 2.60 (t, 2H); 4.37 (m, 1H); 4.51 (s, 2H); 5.37 (s, 1H); 7.20 (d, 2H); 7.31 (d, 2H).

IR (CHCl₃): 2920, 2853, 1651, 1467 cm⁻¹.

EXAMPLE 225

N'-[2-methyl-4,6-bis(methylthio)pyrimidin-5-yl]-N-[4-(2,2-dimethylpropyl)benzyl]-N-cycloheptylurea 70% yield.

¹H NMR (CDCl₃): δ0.89 (s, 9H); 1.39–1.77 (c, 10H); 2.00 (m, 2H); 2.42 (s, 6H); 2.48 (s, 2H); 2.55 (s, 3H); 4.39 (m, 1H); 4.51 (s, 2H); 5.37 (s, 1H), 7.15 (d, 2H); 7.30 (d, 2H).

IR (CHCl₃): 2922, 2852, 1653, 1468, 1413 cm⁻¹.

EXAMPLE 226

N'-[2-methyl-4,6-bis(methylthio)pyrimidin-5-yl]-N-[4-(3-methylbutyl)benzyl]-N-heptylurea 43% yield.

¹H NMR (CDCl₃): δ0.86 (m), 0.92 (d)(total 9H); 1.20–1.72 (c, 13H); 2.47 (s, 6H); 2.57 (s), 2.60 (t) (total 5H); 3.34 (t, 2H); 4.56 (s, 2H); 5.51 (s, 1H); 7.15 (d, 2H); 7.24 (d, 2H).

IR (CHCl₃): 2920, 2850, 1659, 1468, 1415 cm⁻¹.

EXAMPLE 227

N'[2,4-bis(methylthio)-6-methylpyridin-3-yl]-N-[4-(3-methylbutyl)benzyl]-N-heptylurea 32% yield.

¹H NMR (CDCl₃): δ0.87 (m), 0.92 (d) (total 9H); 1.19–1.72 (c, 13H); 2.37 (s, 3H); 2.46 (s, 3H); 2.48 (s, 3H); 2.59 (t, 2H); 3.34 (t, 2H); 4.58 (s, 2H); 5.61 (s, 1H); 6.61 (s, 1H); 7.17 (d, 2H); 7.27 (d, 2H).

IR (CHCl$_3$): 2922, 2852, 1656, 1558, 1467 cm$^{-1}$.

EXAMPLE 228

N-[2-methyl-4,6-bis(methylthio)pyrimidin-5-yl]-2-decylcyclopentanecarboxamide

The title compound was prepared in 27.4% yield according to the procedure of Example 4A.

$^1$H NMR (CDCl$_3$): δ0.87 (t, 3H); 1.2–1.82 (c, 24H); 2.27 (m, 2H); 2.49 (s, 6H); 2.59 (s, 3H); 6.6 (s, 1H).

IR (CHCl$_3$): 2921, 2851, 1681, 1450, 1407, 1360 cm$^{-1}$.

EXAMPLE 229

N-[4,6-bis(methylthio)pyrimidin-5-yl]-2-decylcyclopentanecarboxamide

The title compound was prepared in 20% yield according to the procedure of Example 4A.

$^1$H NMR (CDCl$_3$): δ0.87 (t, 3H); 1.21–1.82 (c, 24H); 2.28 (m, 2H); 2.51 (s, 6H); 6.69 (s, 1H); 8.64 (s, 1H).

IR (CHCl$_3$): 2922, 2850, 1682, 1452, 1405, 1358 cm$^{-1}$.

EXAMPLE 230

N-[4,6-bis(methylthio)pyrimidin-5-yl]-2-decylindane-2-carboxamide

The title compound was prepared in 33.7% yield acording to the procedure of Example 4A.

$^1$H NMR (CDCl$_3$): δ0.86 (t, 3H); 1.14–1.88 (d, 18H); 2.49 (s, 6H); 3.04 (d, 2H); 3.58 (d, 2H); 6.63 (s, 1H); 7.2 (c, 4H); 8.63 (s, 1H).

IR (CHCl$_3$): 2922, 2850, 1687, 1526, 1458, 1407, 1359 cm$^{-1}$.

EXAMPLE 231

N-[2,4-bis(methylthio)-6-methylpyridin-3-yl]-2-methylthiotetradecanoic amide

The title compound was prepared in 66% yield according to the procedure of Example 4B.

$^1$H NMR (CDCl$_3$): δ0.87 (t, 3H); 1.2–1.87 (c, 21H); 2.03 (m, 1H); 2.31 (s, 3H); 2.41 (s, 3H); 2.50 (s, 3H); 2.53 (s, 3H); 3.38 (t, 1H); 6.66 (s, 1H); 8.05 (s, 1H).

IR (CHCl$_3$): 2919, 2850, 1677, 1559, 1522, 1468, 1438 cm$^{-1}$.

EXAMPLE 232

N-(2-methyl-4,6-bis(methylthio)pyrimidin-5-yl)-2-methylthiotetradecanoic amide

The title compound was prepared in 79% yield according to the procedure of Example 4A.

$^1$H NMR (CDCl$_3$): δ0.87 (t, 3H); 1.21–1.86 (c, 21H); 2.04 (m, 1H), 2.29 (s, 3H.); 2.52 (s, 6H); 2.62 (s, 3H); 3.37 (t, 1H); 8.0 (s, 1H).

IR (CHCl$_3$): 2918, 2849, 1681, 1465, 1405 cm$^{-1}$.

EXAMPLE 233

N-[2,4-bis(methylthio)-6-methylpyridin-3-yl]-2-ethylthiotetradecanoic amide

The title compound was prepared in 51% yield according to the procedure of Example 4B.

$^1$H NHR (CDCl$_3$): δ0.87 (t, 3H); 1.2–1.7 (c, 23H); 1.8 (m, 1H); 2.06 (m, 1H); 2.41 (s, 3H); 2.50 (s, 3H); 2.53 (s, 3H); 2.8 (q, 2H); 3.48 (t, 1H); 6.66 (s, 1H); 8.13 (s, 1H).

IR (CHCl$_3$): 2920, 2850, 1675, 1560, 1466 cm$^{-1}$.

EXAMPLE 234

N-[2-methyl-4,6-bis(methylthio)pyrimidin-5-yl)-2-ethylthiotetradecanoic amide

The title compound was prepared in 51% yield according to the procedure of Example 4A.

$^1$H NMR (CDCl$_3$): δ0.87 (t, 3H); 1.2–1.88 (c, 24H); 2.03 (m, 1H); 2.52 (s, 6H); 2.62 (s, 3H); 2.79 (q, 2H); 3.48 (t, 1H); 8.08 (s, 1H).

IR (CHCl$_3$): 2920, 2850, 1679, 1465, 1405 cm$^{-1}$.

EXAMPLE 235

N-(2-methyl-4,6-bis(methylthio)pyrimidin-5-yl]-4,5-dimethyl-trans -2-heptylcyclohex-4-enecarboxamide The title compound was prepared in 31% yield according to the procedure of Example 4A.

$^1$H NMR (CDCl$_3$): δ0.87 (t, 3H); 1.16–2.48 (c, 24H); 2.5 (s, 6H); 2.59 (s, 3H); 6.56 (s, 1H).

IR (CHCl$_3$): 2918, 2850, 1687, 1458, 1406, 1360 cm$^{-1}$.

EXAMPLE 236

N-[4,6-bis(methylthio)pyrimidin-5-yl]-4,5-dimethyl-trans-2-heptylcyclohex-4-enecarboxamide The title compound was prepared in 27% yield according to the procedure of Example 4A.

$^1$H NMR (CDCl$_3$): δ0.87 (t, 3H); 1.17–2.49 (c, 24H); 2.52 (s, 6H); 6.64 (s, 1H); 8.65 (s, 1H).

IR (CHCl$_3$): 2920, 2852, 1690, 1458, 1405, 1356 cm$^{-1}$.

EXAMPLE 237

N-(6-methoxyisoquinolin-5-yl)-4,5-dimethyl-trans-2-heptylcyclohex-4-enecarboxamide The title compound was prepared in 8.5% yield according to the procedure of Example 4.

$^1$H NMR (CDCl$_3$): δ0.86 (t, 3H); 1.14–2.5 (c, 24H); 3.99 (s, 3H); 7.17 (s, 1H); 7.39 (d, 1H); 7.52 (m, 1H); 7.94 (d, 1H); 8.45 (m, 1H); 9.14 (m, 1H).

IR (CHCl$_3$): 2920, 2850, 1678, 1625, 1464, 1382 cm$^{-1}$.

EXAMPLE 238

3-Amino-2,4-bis(methylthio)-6-methylpyridine

To a solution of 15.5 g (0.22 mol) sodium methanethiolate in 200 ml methanol was added slowly with stirring under nitrogen a solution of 20.8 g (0.1 mol) 3-nitro-2,4-dichloro-6-methylpyridine in 150 ml methanol. A precipitate formed and the mixture was stirred overnight at room temperature. The mixture was then filtered and the solid was washed first with methanol and then with water. 3-Nitro-2,4-bis(methylthio)-6-methylpyridine (18.9 g, 82% yield) was obtained as a yellow solid, mp 172–176 C.

$^1$NMR (CDCl$_3$): δ2.45 (s, 3H); 2.51 (s, 3H); 2.55 (s, 3H); 6.77 (s, 1H).

A mixture of 18.9 g (0.082 mol) 3-nitro-2,4-bis(methylthio)-6-methylpyridine and 18.9 g Raney nickel in 600 ml. 1,4-dioxane and 300 ml methanol was shaken with hydrogen (15 psi) in a Parr hydrogenation apparatus for 3.5 hr. The catalyst was filtered and the filtrate was concentrated to dryness in vacuo. The solid residue was chromatographed on silica gel (650 g), eluting with 9:1 hexane/ethyl acetate to yield 14.0 g. (85% yield) of the title compound as an off-white solid.

NMR (CDCl$_3$): δ2.42 (s, 3H); 2.44 (s, 3H); 2.59 (s, 3H); 4.02 (b, 2H); 6.72 (s, 1H).

The title compounds of Examples 239–241 were prepared according to the procedure of Example 238.

EXAMPLE 239

A. 3-Amino-2,4-bis(methylthio)pyridine (79% yield)

$^1$H NMR (CDCl$_3$): δ2.45 (s, 3H); 2.60 (s, 3H); 4.14 (b, 2H); 6.88 (d, 1H); 7.90 (d, 1H).

EXAMPLE 240

B. 3-Amino-2,4-bis(ethylthio)pyridine (86% yield)

$^1$H NMR (CDCl$_3$): δ1.29 (t, 3H); 1.34 (t, 3H); 2.91 (q, 3H); 3.21 (q, 3H); 4.30 (b, 2H); 6.93 (d, 1H); 7.86 (d, 1H).

EXAMPLE 241

C. 3-Amino-2,4-bis(ethyl)-6-methylpyridine (86% yield)

$^1$H NMR (CDCl$_3$): δ1.30 (t, 3H); 1.32 (t, 3H); 2.40 (s, 3H); 2.90 (q, 2H); 3.18 (q, 2H); 4.18 (b,2H); 6.79 (s, 1H).

EXAMPLE 242

(2S)-N-[2,4-bis(methylthio)-6-methylpyridin-3-yl]-2-hexylthiodecandic amide (S)-(−)-2-Hexylthiodecanoic, prepared according to Example IB, was coupled with 3-amino-2,4-bis(methylthio)-6-methylpyridine by the procedure of Example 4B to yield the title compound in 55% yield; $[\alpha]_D^{RT}$=−59° (CH$_3$OH). A sample recrystallized from petroleum ether had mp 81°–83° C. and $[\alpha]_D^{RT}$=−66° (CH$_3$OH).

EXAMPLE 243

(2R)-N-[2,4-bis(methylthio)-6-methylpyridin-3-yl]-2-hexylthiodecanoic amide

The title compound was prepared in 30.1% yield according to a procedure similar to that of Example 243. A sample recrystallized from petroleum ether had mp 80°–82° C. and $[\alpha]_D^{RT}$=+61.7° (CH$_3$OH)

EXAMPLES 244

(2S)-N-[2-methyl-4,6-bis(methylthio)pyrimidin-5-yl]-2-hexylthiodecanoic amide

The title compound was prepared in 47.2% yield by the coupling of S-(−)-2-hexylthiodecanoic acid with 5-amino-4,6-bis(methylthio)-2-methylpyrimidine according to the procedure of Example 4A. A sample recrystallized from diethyl ether had mp 98°–100° C. and $[\alpha]_D^{RT}$=−62° (CH$_3$OH).

EXAMPLE 245

(2R)-N-[2-methyl-4,6-bis(methylthio)pyrimidin-5-yl]-2-hexylthiodecanoic amide

The title compound was prepared in 50.3% yield by a procedure similar to that of Example 245. A sample recrystallized from diethyl ether had mp 95°–97.5° C. and $[\alpha]_D^{RT}$=+56.0° (CH$_3$OH).

EXAMPLE 246

(2S)-N-[6-(methylthio)quinolin-5-yl]-2-hexylthiodecanoic amide

The title compound was prepared by the recoupling of S-(−)-2-hexylthio-decanoic acid with 5-amino-6-methylthioquinoline (Example 34) according to the procedure of Example 25. M.p.: 114°–115° C.

Optical rotation: $[\alpha]_D^{23}$=−52° (in CDCl$_3$). Analytical analysis of enantiomeric purity was accomplished using a Chiracel OD HPLC column.

EXAMPLE 247

N-(6-methylthioquinolin-5-yl)-2-bromodecanamide

To a stirred solution of 2-bromodecanoic acid (184 mg, 0.73 mmol) in CH$_2$C$_{12}$ (3.0 ml) was injected by syringe oxalyl chloride (0.06 ml, 105 mol %) and then DMF (1 drop). After stirring at room temperature for 1 hour, N-methyl morpoline (0.24 ml, 300 mol %) was added. To this mixture was injected a solution of 5-amino-6-methylthioquinoline (139 mg, 100 mol %) in CH$_2$Cl$_2$ (2.0 ml). After stirring at room temperature for an additional 30 min. the reaction mixture was diluted with CH$_2$Cl$_2$ (30 ml), poured over 1.0M H$_3$PO$_4$ (100 ml), and extracted with CH$_2$Cl$_2$ (3×30 ml). The combined extracts were dried (Na$_2$SO$_4$), evaporated, and chromatographed using 1% triethylamine:ethyl acetate as eluants to give the title compound (192 mg, 62% yield).

IR (CDCl$_3$) 3350, 2930–2820, 1710 cm$^{-1}$.

$^1$H NMR (CDCl$_3$) δ8.84 (m, 1H); 8.05 (m, 3H); 7.63 (d, 1H, J=9.4 Hz); 7.41 (dd, 1H, J=3.7, 8.5 Hz); 4.57 (dd, 1H, J=5.5, 8.3 Hz); 2.54 (s, 3H); 2.25 (m, 1H); 2.15 (m, 1H); 1.58 (m, 2 h); 1.26 (m, 10H); 0.85 (m, 3H).

EXAMPLE 248

N-(6-methylthioquinolin-5-yl)-2-hexylaminodecanamide

A mixture of N-(6-methylthioquinolin-5-yl)-2-bromodecanamide (200 mg, 0.47 mmol) and n-hexylamine (10 ml) was heated at 120 C. for 1 hour, cooled to room temperature, and chromatographed using 1:24:25/ triethylamine:ethyl acetate: hexane as eluants to give the title compound as a pink oil (184 mg, 88% yield).

IR (CHCl$_3$) 3280, 2940–2860, 1680 cm.

$^1$H NMR (CDCl$_3$) δ9.38 (s, 1H); 8.80 (m, 1H); 7.97 (m, 2H); 7.62 (d, 1H, J=8.8 Hz); 7.36 (dd, 1H, J=4.3, 8.6 Hz); 3.28 (dd, 1H, J=4.7, 8.6 Hz); 2.86 (m, 1H), 2.78 (m, 1H); 2.51 (s, 3H); 1.98 (m, 1H); 1.74 (m, 1H); 1.56 (m, 5H); 1.30 (m, 16H); 0.86 (m, 6H). Mass spectrum m/e (relative intensity): M$^+$444.30 (82), 226.40 (100).

Anal. Calc'd for C$_{26}$H$_{41}$N$_3$OS: C, 70.4; H, 9.3; N, 9.5; Found: C, 70.9; H, 9.4; N, 9.5.

EXAMPLE 249

N-(6-methylthioquinolin-5-yl)-2-N,N-[(acyl) (hexyl)]aminodecanamide

To a stirred solution of N-(6-methylthioquinolin-5-yl)-2-hexylaminodecanamide (200 mg, 0.45 mmol)pyridine (10 ml) was added in one portion acetic anhydride (2.0 ml).

After stirring at room temperature for 1 hour, the mixture was poured over 1.0M $H_3PO_4$ (200 ml) and extracted with $CH_2Cl_2$ (3×100 ml). The combined extracts were dried ($Na_2SO_4$), evaporated, and chromatographed using ethyl acetate as eluant to give the title compound (200 mg, 91% yield).

$^1$H NMR (CDCl$_3$) δ8.81 (d, 1H, J=2.9 Hz); 8.66 (s, 1H); 8.01 (d, 1H, J=6.7 Hz); 8.00 (d, 1H, J=2.0 Hz); 7.60 (d, 1H, J=9.1 Hz); 7.36 (dd, 1H, J=4.2, 8.6 Hz); 4.95 (m, 1H), 3.33 (t, 2H, J=8.3 Hz); 2.50(s, 3H); 2.24 (s, 3H); 2.15 (m, 1H); 1.88 (m, 1H); 1.66 (m, 2H); 1.25 (m, 18H); 0.86 (m, 6H).

Mass spectrum m/e (relative intensity): M$^+$ 486.3(87), 296.3 (62), 268.3(32), 226.3 (100).

EXAMPLE 250

N-(6-methylthioquinolin-5-yl)-2-N,N-[(hexyl)(methylsulfonyl)]aminodecanamide

To a stirred solution of N-(6-methylthioquinolin-5-yl)-2-hexylaminodecanamide (200 mg, 0.45 mmol) and triethylamine (0.19 ml, 300 mol %) in $CH_2Cl_2$ (5 ml) was added dropwise a mixture of methanesulfonyl chloride (0.038 ml, 110 mol %) in $CH_2Cl_1$ (5 ml) at 0° C. After stirring at 0° C. for 30 min, the reaction mixture was allowed to warm to room temperature. After stirring at room temperature for 3 hours, the mixture was chromatographed using 1% triethylamine:ethyl acetate as eluants to give the title compound (120 mg, 51% yield).

$^1$H NMR (CDCl$_3$) δ8.84 (s, 1H); 8.31 (s, 1H); 8.13 (d, 1H, J=8.4 Hz); 8.05 (d, 1H, J=9.0 Hz); 7.64 (d, 1H, J=9.0 Hz); 7.42 (dd, 1H, J=4.2, 8.5 Hz); 4.51 (t, 1H, J=7.4 Hz); 3.40 (m, 3H); 3.01 (s, 3H); 2.54 (s, 3H); 2.19 (m, 1H); 1.77 (m, 2H); 1.28 (m, 18H); 0.87 (m, 6H).

Mass spectrum m/e (relative intensity): M$^+$522.3 (100).

EXAMPLE 251

N-(6-methylthioquinolin-5-yl)-2-N,N-[(bensenesulfonyl)(hexyl)]aminodecanamide

The title compound was prepared according to the procedure of Example 250.

$^1$H NMR (CDCl$_3$) δ8.85 (s, 1H); 8.50 (s, 1H); 8.22 (d, 1H, J=8.4 Hz); 8.11 (d, 1H, J=9.0 Hz); 7.91 (m, 2H); 7.68 (d, 1H, J=9.0 Hz); 7.59 (m, 3H); 7.45 (dd, 1H, J=4.1, 8.5 Hz); 4.45 (t, 1H, J=7.3 Hz); 3.49 (m, 2H); 3.28 (m, 1H); 2.56 (s, 3H); 2.06 (m, 1H); 1.76 (m, 2H); 1.20 (m, 18H); 0.86 (m, 6H).

Mass spectrum m/e (relative intensity): M$^+$584.4 (100).

EXAMPLE 252

N-[4-dimethylamino-6-(cyano)(hexyl)aminopyrimidin-5-yl]-2-N,N-[(cyano)(hexyl)]aminodecanamide To a stirred solution of N-[4-dimethylamino-6-hexylaminopyrimidin-5-yl)-2-hexylaminodecanamide (200 mg, 0.41 mmol), N-methyl morpholine (5 drops) in THF (5 ml) was added in one portion solid cyanobromide (95 mg, 220 mol %). After stirring at room temperature for 1 hour the mixture was chromatographed using 1:1/ethyl acetate:hexane as eluants to give the title compound (130 mg, 59% yield).

IR (CHCl$_3$) 3450, 3000–2800, 2200, 1740, 1650, 1600 cm$^{-1}$.

$^1$H NMR (CDCl$_3$) δ8.24 (s, 1H); 4.22 (m, 1H); 4.07 (m, 2H); 3.40 (m, 2H); 3.18 (m, 1H); 2.97 (s, 3H); 2.96 (s, 3H); 2.12 (m, 1H); 1.94 (m, 1N); 1.64 (m, 2H); 1.49 (m, 2H); 1.28 (m, 24H); 0.86 (m, 8H).

Mass spectrum m/e (relative intensity): M$^+$542 (100); Anal. calc'd for $C_{30}H_{52}N_8O$: C, 66.6; H, 9.7; N, 20.7; Found: C, 66.4; H, 9.8; N, 20.6.

EXAMPLE 253

N-(6-methylthioisoquinolin-5-yl)-2-(hexylthio)decanamide

Commercially available 4-chlorobenzaldehyde (10 g) was cyclized with aminoacetaldehyde diethyl acetal according to the procedure of Hendrickson, et. al., *J. Org. Chem.*, 48, 3344 (1983), to give 6-chloroisoquinoline (600 mg). Nitration of the obtained product using the procedure of Campbell et. al., *J. Am. Chem. Soc.*, 68, 1559 (1946) gave 6-chloro-5-nitroisoquinoline (700 mg). Substitution of 6-chloro for thiomethoxide according to the procedure of Massie, *Iowa State Coll, J. Sci.*, 21, 41 (1946) (Ca 41:3033 g) gave 6-methylthio-5-nitroisoquinoline (632 mg). This material (200 mg) was reduced using stannous chloride (2.0 g) and concentrated hydrochloric acid (30 ml) to give 5-amino-6-(methylthio) isoquinoline (143 mg). This material (140 mg) was coupled with 2-hexylthiodecanoic acid (prepared according to the procedures described in Examples 1 and 3) using the procedure described in Example 25 to give the title compound (80 mg).

$^1$H NMR (CDCl$_3$) δ9.16 (s, 1H); 8.59 (s, 1H); 8.48 (d, 1H, J=5.9 Hz); 7.88 (d, 1H, J=8.7 Hz); 7.48 (m, 2H); 3.54 (dd, 1H, J=6.3, 8.1 Hz); 2.79 (t, 2H, J=7.4Hz); 2.55 (s, 3H); 2.12 (m, 1H); 1.88 (m, 1H); 1.65 (m, 4H); 1.30 (m, 16 H); 0.88 (m, 6H).

Mass spectrum m/e (relative intensity): M$^+$461.3; Anal. calc'd for $C_{26}H_{40}N_2OS_2$: C, 67.8; H, 8.8; N, 6.1; Found: C, 67.9; H, 8.9; N, 6.1.

EXAMPLE 254

N-[4,6-bis(dimethylamino)pyrimidin-5-yl]-cis-9-octadecenamide

5-Amino-4,6-bis(dimethylamino)pyrimidine (prepared by reacting commercially available 4,6-dichloro-5-nitro pyrimidine with excess dimethylamine followed by reduction of the nitro group according to the procedure of Jacobs et. al., *J. Am. Chem. Soc.*, 42, 2278 (1920)) was coupled with oleoyl chloride using the procedure described in Example 4 to give the title compound.

$^1$H NMR (CDCl$_3$) δ8.15 (s, 1H); 7.52 (s, 1H); 5.31 (m, 2H); 3.06 (s, 6H); 2.99 (s, 6H); 1.98 (m, 4H); 1.72 (m, 2H); 1.24 22H); 0.85 (m, 3H).

Mass spectrum m/e (relative intensity): M$^+$446 (100), 182 (47).

EXAMPLE 255

N-(4-dimethylamino-6-chloropyrimidin-5-yl)-cis-9-octadecenamide

5-Amino-4-(dimethyl)amino-6-chloropyrimidine (prepared by reacting commercially available 5-amino-4,6-dichloropyrimidine with excess dimethylamine) was coupled with oleoyl chloride according to the procedure described in Example 4 to give the title compound.

IR (CHCl$_3$) 3400, 3000–2800, 1700, 1570 cm$^{-1}$.

$^1$H NMR (CDCl$_3$) δ8.23 (s, 1H); 6.82 (s, 1H); 5.34 (m, 2H); 3.15 (s, 6H); 2.40 (t, 2H, J=7.6 Hz); 2.01 (m, 4H); 1.73 (m, 2H); 1.25 (m, 20H); 0.86 (m, 3H).

Mass spectrum m/e (relative intensity): M$^+$437 (100). Anal. Calc'd for C$_{24}$H$_{41}$N$_4$OCl: C, 66.0; H, 9.5; N, 12.8. Found: C, 65.7; H, 9.5; N, 12.9.

EXAMPLE 256

N-(4-dimethylamino-6-methylthiopyrimidin-5-yl)-cis-9-octadecenamide

5-Amino-4-dimethylamino-6-methylthiopyrimidine (prepared by reacting 5-amino-4-dimethylamino-6-chloropyrimidine with sodium thiomethoxide) was coupled with oleoyl chloride using the procedure described in Example 4 to give the title compound.

IR (KBr) 3220, 3000–2800, 1650, 1550 cm$^{-1}$.

$^1$H NMR (CDCl$_3$) 8.32 (s, 1H); 6.68 (s, 1H); 5.33 (m, 2H); 3.09 (s, 6H); 2.45 (s, 3H); 2.37 (t, 2H, J=7.7 Hz); 2.00 (m, 4H); 1.72 (m, 2H); 1.25 (m, 20H); 0.86 (m, 3H).

Mass spectrum m/e (relative intensity): M$^+$449.4 (62), 185 (100). Anal. Calc'd for C$_{25}$H$_{44}$N$_4$OS: C, 66.9; H, 9.9; N, 12.5. Found: C, 67.3; H, 10.2; N, 12.4.

EXAMPLE 257

N-(4-bromoisoquinolin-5-yl)-2-hexylthiodecanamide

5-Amino-4-bromoisoquinoline (prepared according to the process described by Gordon et. al., *J. Het. Chem.*, 4, 410 (1967)) was coupled with 2-hexylthiodecanoic acid (prepared by the procedures described in Examples 1 and 3) using the procedure described in Example 25 to give the title compound.

IR (CHCl$_3$) 3320, 3000–2800, 1680 cm$^{-1}$.

$^1$H NMR (CDCl$_3$) δ10.10 (s, 1H); 9.11 (s, 1H); 8.68 (s, 1H); 8.51 (d, 1H, J=7.7 Hz); 7.82 (dd, 1H, J=1.2, 8.1 Hz); 7.67 (t, 1H, J=8.0 Hz); 3.50 (t, 1H, J=7.3 Hz); 2.60 (t, 2H, J=7.3 Hz); 2.05 (m, 1H); 1.82 (m, 1H); 1.59 (m, 4H); 1.24 (m, 16H); 0.85 (m, 6H).

Mass spectrum m/e (relative intensity): M$^+$495 (50), 415 (100). Anal. calc'd for C$_{25}$H$_{37}$N$_2$OSBr: C, 60.8; H, 7.6; N, 5.7. Found: C, 61.0; H, 7.5; N, 5.7.

EXAMPLE 258

N-(4-methylthioisoquinolin-5-yl)-2-hexylthiodecanamide

5-Amino-4-bromoisoquinoline (prepared according to the process described by Gordon et al., *J. Het. Chem.*, 4, 410 (1967)) was allowed to react with sodium thiomethoxide according to the procedure of Massie, *Iowa State Coll. J. Sci.*, 21, 41 (1946) (Ca. 41: 3044 g) to give 5-amino-4-methylthioisoquinoline. This material was coupled with 2-hexylthiodecanoic acid (prepared by the procedures described in Examples 1 and 3) using the procedure described in Example 25 to give the title compound.

IR (KBr) 3230, 3000–2800, 1660 cm$^{-1}$.

$^1$H NMR (CDCl$_3$) δ11.65 (s, 1H); 9.12 (s, 1H); 8.84 (d, 1H, J=7.8 Hz); 8.63 (s, 1H); 7.76 (dd, 1H, J=1.2, 8.1 Hz); 7.64 (t, 1H, J=8.0 Hz); 3.44 (t, 1H, J=7.5 Hz); 2.65 (m, 2H); 2.53 (s, 3H); 2.03 (m, 1H); 1.83 (m, 1H); 1.59 (m, 4H); 1.24 (m, 16H); 0.84 (m, 6H).

Mass spectrum m/e (relative intensity): M$^+$461.3 (100). Anal. calc'd for C$_{26}$H$_{40}$N$_2$OS$_2$: C, 67.8; H, 8.8; N, 6.1. Found: C, 68.0; H, 8.9; N, 6.0.

EXAMPLE 259

N-(4-bromoisoquinolin-5-yl)-cis-9-octadecenamide

5-Amino-4-bromoisoquinoline (prepared according to the process described by Gordon et al., *J. Het. Chem.*, 4, 410 (1967)) was coupled with oleoyl chloride using the procedure described in Example 4, to give the title compound.

IR (CHCl$_3$) 3420, 3000–2800, 1695 cm$^{-1}$.

$^1$H NMR (CDCl$_3$) δ9.10 (s, 1H); 9.04 (s, 1H); 8.65 (s, 1H); 8.42 (d, 1H, J=7.3 Hz); 7.80 (d, 1H, J=8.0 Hz); 7.65 (t, 1H, J=7.9 Hz); 5.33 (m, 2H); 2.49 (t, 2H, J=7.3 Hz); 2.00 (m, 3H); 1.80 (m, 2H); 1.25 (m, 21H); 0.86 (m, 3H).

Mass spectrum m/e (relative intensity): M$^+$489.3 (37), 461.3 (14), 407.3 (100). Anal. calc'd for C$_{27}$H$_{40}$N$_2$OBr: C, 66.8; H, 8.1; N, 5.8. Found: C, 67.3; H, 8.4; N, 5.6.

EXAMPLE 260

N-(4-dimethylamino-6-hexylaminopyrimidin-5-yl)-2-hexylaminodecanamide

5-Amino-4-(dimethyl)amino-6-chloropyrimidine (prepared as described in Example 257) was coupled with 2-bromodecanoic acid using the procedure described in Example 249, followed by the addition of n-hexylamine as described in Example 250 to give the title compound.

IR (CHCl$_3$) 3280, 3000–2700, 1660, 1600 cm$^{-1}$.

$^1$H NMR (CDCl$_3$) δ8.86 (s, 1H); 8.20 (s, 1H); 5.47 (t, 1H, J=5.0 Hz); 3.40 (m, 2H); 3.18 (m, 1H); 2.88 (s, 6H); 2.66 (m, 2H); 1.85 (m, 1H); 1.44 (m, 31H); 0.86 (m, 8H).

Mass spectrum m/e (relative intensity): M$^+$491.5 (100). Anal. calc'd for C$_{28}$H$_{54}$N$_6$O: C, 68.5; H, 11.1; N, 17.1. Found: C, 68.8; H, 11.3; N, 17.5.

EXAMPLE 261

(2S)-Methyl-2hexylthiodecanoate (2R)-Methyl-2-hydroxydecanoate (202.3 g, 1.00 mol) was dissolved of in 5 L of dry acetonitrile. The vessel was flushed with nitrogen and cooled to an internal temperature of −25° C. Triflic anhydride (185 mL, 310 g, 1.10 mol) was added slowly followed by triethylamine (TEA) (150 mL, 111 g, 1,10 mol) at such a rate that the internal temperature stayed below −20° C. The reaction remained clear and colorless; rapid addition of TEA will cause coloring. The reaction was stirred for fifteen minutes after the TEA addition. Then layer chromatography revealed (eluting with 10:1 hexane/ethyl acetate, developing with PMA and heat) that the starting material (R$_f$ 0.2) was gone.

Hexanethiol (193 mL, 162 g, 1.30 mol) was added rapidly followed by slow addition of TEA (181 mL, 131 g, 1.30 mol). The reaction was warmed to room temperature and stirred for on hour. TLC (eluting with 10:1 hexanes to ethyl acetate revealed (2S)-methyl-2-hexylthiodecanoate at R$_f$ 0.5. The acetonnitrile was azeotroped with ethy acetate. The ethyl acetate was washed with 3 L of water and then with 1 L of brine. The organic layer was dried with MgSO$_4$ and concentrated to an oil. The oil was filtered through silica gel [Kieselgel 60 (trademark) (230–400 mesh), 15 g silica/g crude product], eluted with hexane and flushed with 30:1 hexane/ethyl acetate to give (2S)-methyl-2-hexythiodecanoate (295 g, 0.97 mol, 97%) as a colorless oil.

[α]$_D$=−72.5° (c=1, MeOH).

$^1$H NMR 3.71 (s, 3H), 3.21 (dd, 1H, J=7, 8 Hz), 2.55 (m, 2H), 1.88–1.15 (m, 22H), 0.95 (m,6H); $^{13}$C NMR 173.46, 52.05, 46.64, 31.81, 31.46, 31.37,31.30, 29.30, 29.17, 28.51, 27.38, 22.63, 22.50, 14.06,13.99.

Anal. Calcd. for C$_{17}$H$_{34}$O$_2$S: C, 67.50; H, 11.33. Found: C, 67.60; H, 11.45%.

EXAMPLE 262

(2S)-2-Hexylthiodecanoic acid

To a 12 L flask equipped with a condenser and overhead stirrer was added (2S)-methyl-2-hexylthiodecanoate (302.5 g, 1.00 mol), and 3 L of dry acetonitrile. To this solution was added sodium iodide (600 g, 4.00 mol) and iodine (25.4 g, 0.10 mol) followed by chlorotrimethylsilane (543 g, 635 ml, 5.00 mol). The reaction was heated to an internal temperature of 55° C. After 12 hours, an additional portion of chlorotrimethylsilane (130 g, 152 mL, 1.20 mol) was added and heating continued for 8 hours. The reaction was colled to 0° C., 6 L of hexane was added to separate. The top hexane layer was separated and set aside. The combined $CH_cCN$/water layers were extracted with hexane (2×6L). The combined hexane layers were washed with 1 L of water, 0.1M $Na_2S_2O_3$ (2× 3 L) and once with 3 L of 1:1 brine/water. The combined hexane extracts were dried with $MgSO_4$, filtered and concentrated to give (2S)-2-hexlythiodecanoic acid (260 g, 0.90 mol, 90%) a colorless oil.

$[\alpha]_D$=−59.40° (c=1, MeOH.

$^1$H NMR δ3,19 (m, 1H), 2.63 (m, 2H), 1.95–1.18 (m, 22H), 0.95 (m, 6H).

(2S)-2-Hexylthiodecanoic acid was purified by formation of the dicyclohexylamine salt. (2S)-2-hexylthiodecanoic acid (0.30 gm, 1.05 mmol) was dissolved in 5 ml of $C_3CN$ and to this solution was added dicylohexyl amine (0.19 gm, 1.05 mmol) at room temperature. After stirring for 1 hour the salts were collected by filtration and recrystallized in 5–10 ml of $C_3CN$. Dicyclohexyl-ammonium (2S)-2-hexylthiodecanoate was collected by filtration (0.420 gm, 0.89 mmol, 85%).

M.p. 84°–85° C. The salt was cleaved by stirring in 1N HCl and hexane for 1 hour. The (2S)-2-hexylthiodecanoic acid was recovered by extraction as above.

EXAMPLE 263

(2S)-N-(6-Methylthioquinolin-5-yl)-2-hexylthiodecanoicamide (2S)-2-hexylthiodecanoic acid (Example 16) (0.89 g, 3.08 mmol) was dissolved in 15 ml of methylene chloride and cooled to 0° C. A catalytic amount of dimethylformamide (DMF) (0.012 ml, 0.15 mmol) was added followed by oxalyl chlorid (0.32 ml, 3.70 mmol). The reaction was allowed to warm to room temperature and stirred for 1–1.5 hours. N-6-Methylthio-5-quinolinamine (0.616 g, 3.24 mmol) was dissolved in 2 ml of pyridine and added dropwise to the reaction. The reaction was stirred at room temperature for 3 hours. Ethyl acetate (35 ml) was added and the organic phase was washed with saturated $NaHCO_3$ (2×10 ml) followed by water (2×10 ml). The ethyl acetate extracts were dried and concentrated to give crude (2S)-N-(6-methylthioquinolin-5-yl)-2-hexylthiodecanoic amide (2.22 g recovered). (2S)-N-(6-Methylthioquinolin-5-yl)-2-hexylthiodecanoicamide was recrystallized from acetonitrile (6 ml) to give the pure title compound (1.02 g, 2.2 mmol, 72%) as a white solid.

M.P. 113.5°–114.5°, $[\alpha]_D$=−73.0° (c=0–7, MeOH; $[\alpha]_D$=−51.6° (C=0.5, $CHCl_3$).

IR ($CHCl_3Y$) 3652, 3304, 2921, 2851, 1674, 1584, 1566, 1468, 1376, 1311, 1170, 969, 866, 823 cm$^{-1}$; $^{13}$C NMR 171.96, 149.75, 146.71, 134.26, 131.36, 129.51, 128.99, 126.89, 125.63, 121.69, 51.08, 33.08, 32.27, 31.87, 31.43, 29.42, 29.30, 29.25, 28.65, 27.78, 22.68, 22.55, 15.73, 14.12, 14.03.

Anal. Calcd for $c_{26}H_{40}N_2OS_2$: C, 67.78; H, 8.75; Bm 6.08. Found C, 67.71; H, 8.82; N, 6.03%.

$^1$H NMR 8.84 (dd, 1H, J=2.5, 4.2 Hz), 8.61 (s, 1H), 8.04 (t, 2H), J=8.87 Hz, 7.66 (d, 1H, J=8.7 Hz), 7.39 (dd, 1H, J=8.5, 8.7 Hz) 3.52 (dd, 1H, J=6.2, 8.1 Hz) 2.79 (t, 2H, J=7.3 Hz), 2.55 (s, 3H), 2.12 (m, 1H), 1.85 (m, 1H), 1.65–1.29 (m, 20H), 0.85 (m, 6 h),

EXAMPLE 264

(2)-N-(6-Methylthioqulnolin-5-yl)-2-hexylthiodecanoamide

N-6-Methylthio-5-quinolinamine (0.61 g, 3.23 mmol) was dissolved in 20 ml of methylene chloride. A solution of $AlMe_3$ (0.23ml, 6.46 mmol of 2.0M solution in hexane) was added dropwise. The reaction mixture turned bright red and was stirred at room temperature for 20 minutes. (2S)-methyl-2-hexylthiodecanoate was added in 10 ml of methylene chloride and the reaction heated to a bath temperature of 55° C. After 20 hours the reaction was cooled, poured into a saturated aqueous solution of $NaHCO_3$ and extracted with ethyl acetate (2×60 ml). The organix phase was washed with $NaHCO_3$ followed by brine, dried over $MgSO_4$ and concentrated to give yellow solids (1.50 gm, 3.25 mmol, 100%). The solids were recrystallized from 10 ml of acetonitrile to yield (2S)-N-(6-methylthioquinolin-5-yl)-2-hexythiodecanoamide as a white solid (0.58 gm, 1.26 mmol, 39%).

$[\alpha]_D$=−51.74° (c=0.31, $CHCl_3$).

M.p. 101°–102° C.

Exact mass (EI) calculated for $C_{26}H_{40}N_2S_2O$: 460.2573. Found: 460.1575.

EXAMPLE 265

(2S]-N-2,4[(Methylthio)-6-methyl-3-pyridinyl]-2-phenylthiodecanoamide

N-2,4-(Methylthio)-6-methyl-3pyridinamine (0.117 gm, 0.58 mmol) was dissolved in 3 ml of methylene chloride and treated with $AlMe_3$ (0.65 ml, 1.28 mmol of 2.0M solution in hexane). This solution was heated to a bath temperature of 50°–55° C. and stirred for 1–1.5 hours. Methyl 2-phenylthiodecanoate was added to the reaction in 1 ml of methylene chloride. Heating was continued for 5 hours; then the reaction was allowed to stir at room temperature for 48 hours. The reaction was slowly poured into saturated $NaHCO_3$ (5 ml) and extracted with ethyl acetate 2×10 ml). The combined organic layers were washed with $NaHCO_3$ (2×5 ml), brined and dried over $MgSO_4$. Following concentration of the solvent, the crude oil was recrystallized from 1.5 ml of acetonitrile to give (2S)-N-2,4-[(Methylthio)-6-methyl-3-pyridinyl]2-phenylthiodecanamide (0.104 gm, 0.22 mmol, 39%) as a white solid.

M.p. 102°–104° C.

EXAMPLE 266

(2R)-N-(6-Methylthioquinolin-5-yl)-2-hydroxydecanoamide (2R)-2Hydroxydecanoic acid (2.3 gm, 12.24 mmol) was dissolved in 70 ml of methylene chloride and [FILL IN NAME] TMSCI (3.42 ml, 26.9 mmol) and catalytic DMPA were added to the reaction. Pyridine (2.18 ml, 26.9 mmol) was added slowly and the reaction was cooled to 0° C. and 0.4 ml of DMF added followed by oxalyl chloride (1.28 ml, 14.67 mmol). The reaction was allowed to warm slowly to room temperature over 1.5 hours. The amine (2.33 gm, 12.24 mmol) was dissolved in 15 ml of pyridine and added to the reaction. Stirring was continued at room temperature for 6 hours. The reaction was poured into a saturated solution of NaHCO₃ (50 ml) and extracted with ethyl acetate (2×100 ml). The organic layers were washed with saturated NaHCOs (2×50 ml) and brine. The combined ethyl acetate layers were dried (MgSO₄) and concentrated to give an orange oil (6 gm). This material was dissolved in 75 ml of THF at room temperature and NBu₄NF-3H₂O (4.64 fm, 14.7 mmol) added and the reaction stirred for 4 hours. The reaction was poured into saturate NaHCO₃ (50 ml) and extracted with ethyl acetate (2×100 ml). The organic phase was washed with brine, dried (MgSO₄) and concentrated to a waxy solid (6 gm). The solid was recrystallized from ethy acetate (50 ml) to give (2R)-N-(-methylthioquinolin-5-yl)-2-hydroxydecanoamide (3.53 gm, 9.79 mmol, 80%) as a beige solid.

[α]_D=+3.49° (C=0.41, MeOh).

M.p. 119°–120° C.

EXAMPLE 267

(2S)-N-(6-Methylthioquinolin-5-yl)-hexylthiodecanoamide (2R)-N-(6-Methylthioquinolin-5-yl)-2-hydroxydecanoamide (0.55 gm, 1.5 mmol) was dissolved in 10 ml of methylene chloride, cooled to 0° C. and treated with catalytic DMAP followed by TEA (0.25 ml, 1.8 mmol) and MsCl (0.14 ml, 1.8 mmol). The reaction was stirred for 2 hours and then poured into saturated NaHCO₃ (5 ml) and extracted with ethyl acetate (10 ml). The organic layer was washed with brine, dried (MgSO₄) and concentrated to a foam. The material was purified by silica gel chromatography using 80% ethyl acetate to hexane as the eluent. (2R)-N-(6-Methlythioquinolin-5-yl)-2-methanesulfonate decanoamide was obtained (0.341 gm, 0.78 mmol, 52%).

¹H NMR δ8.68 (d, 1H, J=2.8 Hz), 8.54 (s, 1H), 7.95 (d, 1H, J=8.4 Hz), 7.21 (m, 1H), 5.11 (t, 1H, J=6.6 Hz), 3.05 (s, 3H), 2.33 (s, 3H), 1.97–1.21 (m, 14H), 0.83 (t, 3H, J=6.63 Hz).

Hexanehtiol (0.077 ml, 0.54 mmol) was dissolved in 2 ml of THF and treated with KOtBu ((0.025 gm, 0.22 mmol) and the reaction stirred at rt for 30 minutes. To the solution was added (2R)-N-(6-methlythioquinolin-5-yl)-2-methanesulfonatedecanoamide (0.08 gm, 0.18 mmol) in 1 ml of THF and the reaction of THF and the reaction stirred at room temperature for 1 hour. The reaction was poured into saturate NaHCO₃ (5 ml) and extracted with ethyl acetate (2×10 ml). The organic layer was washed with brine, dried (MgSO₄) and concentrated to give (2S-N-(6-methylthioquinolin-5-yl)-2-hexylthiodecanoamide as a white solid (0.68 gm, 0.147 mmol, 82%).

[α]_D=−17.74° (C=0.45, MeOH.

M.p. 86°–88° C.

EXAMPLE 268

(2S)-N-(6-Methylthioquinolin-5-yl)-2-phenylthiodecanoamide

Thiophenol (0.15 ml, 1.46 mmol) was dissolved in 5 ml of THF and cooled to 0° C. To this solution was added potassium t-butoxide (KOtBu) (0.084 gm, 0.75 mmol) and the slurry was stirred for 30 minutes. (2R)-N-(6-Methylthioquinolin-5-yl)-2-methanesulfonatedecanoamide (0.218 gm, 0.49 mmol) was dissolved in 2 ml of THF and added to the thiol solution. The reaction was allowed to slowly warm to room temperature and stirred for 2 hours. The reaction was poured into saturated NaHCO₃ and extracted with ethyl acetate. The organic layer was washed with brine, dried and concentrated to a crude oil. The oil was purified by silica gel chromatography using 50% hexane/ ethyl acetate as the eluent to yield (2S)-N-(6-methylthioquinolin-5-yl)-2-phenylthiodecanoamide as a white solid (0.14 gm, 0.31 mmol, 63%).

M.p. 126°–128° C.

EXAMPLE 269

(2S)-N-(6-Methylthioquinolin-5-yl)-2-phenylthiodecanoamide (2R)-N-(6-Methylthioquinolin-5-yl)-2-methanesulfonatedecanoamide (0.29 gm, 0.66 mmol) and thiophenyl (0.13 ml, 1.26 mmol) were dissolved in 6 ml of acetonitrile. To this solution was added tetramethyl quanidine (0.091 ml, 0.73 mmol) and the reaction stirred at room temperature for 2 hours. The reaction was poured into NaHCO₃ (ml) and extracted with ethyl acetate (2×10 ml). The organic layers were washed with brine, dried (MGSO₄) and concentrated to yiedl a crude solid that was crystallized from 10 ml of acetonitrile to give (2S)-N-(6-methylthioquinolin-5-yl)-2-phenylthiodecanoamide as a white solid (0.168 gm, 0.37 mmol, 56%).

M.p. 128°–129° C.

HRMS calc'd for C₂₆H₃₂ON₂A₂, 452.1949. Found, 452.1970.

We claim:

1. A compound of the formula

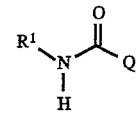

I wherein Q is —CR²R³R⁴ or —NR¹⁷TR¹⁸;
R¹ is

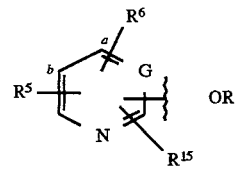

XXVI

R², R³ and R⁴ may be the same or different, and (a) are selected from the group consisting of hydrogen, (C₁–C₆) alkyl, A, XR¹⁰, phenyl-(C₁–C₇) alkyl, and (C₅–C₆) cycloalkyl-(C₁–C₆) alkyl, with the proviso that at least one of R², R³ and R⁴must be A, and with the proviso that when R¹ is is NR¹⁹R²⁰, (C₁–C₆)alkylthio, (C₅–C₇)cycloalkylthio, phenyl (C₁–C₆)alkylthio, phenylthio or heteroalkylthio, either at least one of R², R³ and R⁴ must be XR¹⁰, or two of R², R³ and R⁴must be A; or (b) R² and R³ together with the carbon to which they are attached form a cyclic or bicyclic system selected from the group consisting of (C₃–C₇) cycloalkyl, (C₃–C₇) cycloalkenyl, (C₆–C₁₄) bicycloalkyl, (C₆–C₁₄) bicycloalkenyl, and aryl-fused systems containing 8 to 15 carbon atoms, one ring of any of said aryl-fused systems being aromatic and the ring containing the carbon to which R² and R³ are attached being non-aromatic, one of the carbons of said aromatic ring being optionally replaced by sulfur or oxygen, one or more carbons of said non-aromatic ring being optionally replaced by sulfur or oxygen, one or two carbons of said cycloalkyl or bicycloalkyl groups being optionally replaced by sulfur or oxygen, and said cyclic or bicyclic system being optionally substituted with one to five substituents independently selected from the group consisting of phenyl, substituted phenyl, ($C_1$–$C_6$) alkyl and A, with the proviso that one and only one of said substituents is A, and one and only one of said substituents is phenyl or substituted phenyl, said substituted phenyl being substituted with one or more substituents independently selected from the group consisting of ($C_1$–$C_6$) alkyl, ($C_1$–$C_6$) alkylthio, halogen and trifluoromethyl; and $R^4$ is hydrogen, $XR^{10}$ or A; with the proviso that when $R^1$ is a group of the formula XXVI wherein G is nitrogen and wherein neither $R^5$, $R^6$ nor $R^{15}$ is $NR^{19}R^{20}$, ($C_1$–$C_6$)alkylthio, ($C_5$–$C_7$) cycloalkylthio, phenyl($C_1$–$C_6$) alkylthio, phenylthio or heteroalkylthio $R^2$ and $R^3$ together with the carbon to which they are attached, do not form a ($C_3$–$C_7$) cycloalkyl ring containing only carbon atoms;

A is a hydrocarbon containing 4 to 16 carbons and 0, 1 or 2 double bonds;

X is O, S, SO, $SO_2$, NH, $NR^{23}CO$ or $NSO_2R^{24}$, wherein $R^{23}$ is hydrogen or ($C_1$–$C_6$)alkyl and $R^{24}$ is ($C_1$–$C_6$) alkyl, phenyl or ($C_1$–$C_3$) alkyl-phenyl; $R^5$, $R^6$, and $R^{15}$ are each independently selected from the group consisting of hydrogen, halogen, ($C_1$–$C_6$) alkyl, ($C_1$–$C_6$) haloalkyl, ($C_1$–$C_6$) alkoxy, ($C_1$–$C_6$) alkylthio, ($C_3$–$C_7$) cycloalkylthio, phenyl ($C_1$–$C_6$) alkylthio, substituted phenylthio, heteroarylthio, heteroaryloxy, and $NR^{19}R^{20}$, wherein $R^{19}$ and $R^{20}$ are the same or different and are selected from the group consisting of hydrogen, ($C_1$–$C_6$) alkyl, phenyl, substituted phenyl, ($C_1$–$C_6$) acyl, aroyl, and substituted aroyl, wherein said substituted phenyl and substituted aroyl groups are substituted with one or more substituents independently selected from the group consisting of ($C_1$–$C_6$) alkyl, ($C_1$–$C_6$) alkoxy, ($C_1$–$C_6$) alkylthio, halogen and trifluoromethyl, or $R^{19}$ and $R^{20}$, together with the nitrogen to which they are attached, form a piperidine or morpholine ring;

$R^{10}$ is selected from the group consisting of ($C_4$–$C_{12}$) cycloalkyl, ($C_4$–$C_{12}$) straight or branched alkyl, ($C_4$–$C_{12}$) cycloalkyl-($C_1$–$C_6$) alkyl, phenyl-($C_1$–$C_6$) alkyl, substituted phenyl-($C_1$–$C_6$) alkyl, ($C_1$–$C_6$) alkylphenyl, ($C_1$–$C_6$) alkyl-substituted phenyl, substituted thiazoles, substituted benzothiazoles, and substituted pyridines; wherein the substituents on the substituted phenyl, substituted thiazoles, substituted benzothiazoles and substituted pyridines are selected from the group consisting of ($C_1$–$C_6$) alkoxy, ($C_1$–$C_6$) alkylthio, ($C_1$–$C_6$) alkyl, halo and trifluoromethyl;

G is selected from the group consisting of nitrogen and carbon, and with the proviso that when G is nitrogen, the group XXVI is attached to the nitrogen of formula I at the 4 or 5 position of the pyrimidine ring (designated by a and b);

and $R^{17}$ and $R^{18}$ are each independently selected from the group consisting of ($C_4$–$C_{12}$) straight or branched alkyl, phenyl-($C_1$–$C_6$) alkyl, and ($C_1$–$C_6$) alkylphenyl-($C_1$–$C_6$) alkyl;

or a pharmaceutically acceptable salt of said compound.

2. A compound according to claim 1, said compound being selected from the group consisting of:

(2S)-N-[2,4-bis(methylthio)-6-methylpyridin-3-yl]-2-hexylthiodecanoic amide;

(2S)-N-[2-methyl-4,6-bis(methylthio)pyrimidin-5-yl]-2-hexylthiodecanoic amide;

N'-[2,4-bis(methylthio)-6-methylpyridin-3-yl]-N-[4-(3-methylbutyl)benzyl]-N-cycloheptylurea;

N'-[2,4-bis(methylthio)-6-methylpyridin-3-yl]-N-[4-(3-methylbutyl)benzyl]-N-heptylurea;

N'-[4,6-bis(methylthio)-2-methylpyrimidin-5-yl]-N-[4-(3-methylbutyl)benzyl]-N-cycloheptylurea;

N'-[4,6-bis(methylthio)-2-methylpyrimidin-5-yl]-N-[4-(3-methylbutyl)benzyl]-N-heptylurea;

N-[4,6-bis(methylthio)-2-methylpyrimidin-5-yl]-4,5-dimethyl-trans-2-heptylcyclohex-4-ene-carboxamide;

N-[4,6-bis(methylthio)-2-methylpyrimidin-5-yl]-2-heptylnonanoic amide;

N-[4,6-bis(methylthio)-2-methylpyrimidin-5-yl] pentadecanoic amide;

N-[2,4-bis(methylthio)-6-methylpyridin-3-yl-] pentadecanoic amide;

N-[2,4-bis(methylthio)-6-methylpyridin-3-yl]-(Z)-9-octadecenoic amide;

N-[4,6-bis(methylthio)-2-methylpyrimidin-5-yl]-(Z)-9-octadecenoic amide;

N-[4,6-bis(methylthio)-2-methylpyrimidin-5-yl]-trans-3-nonyl-1,2,3,4-tetrahydro-2-naphthoic amide;

N-[4,6-bis(methylthio)pyrimidin-5-yl]-trans-3-nonyl-1,2,3,4-tetrahydro-2-naphthoic amide.

3. A pharmaceutical composition for inhibiting acyl coenzyme A: cholesterol acyltransferase, inhibiting intestinal absorption of cholesterol, reversing or slowing the development of atherosclerosis, or lowering the concentration of serum cholesterol in a mammal, comprising an amount of a compound according to claim 1 that is effective in inhibiting acyl coenzyme A: cholesterol acyltransferase or intestinal absorption of cholesterol, or is effective in reversing or slowing the development of atherosclerosis or lowering the concentration of serum cholesterol, and a pharmaceutically acceptable carrier.

4. The compound according to claim 1 comprising at least one radiolabel.

5. The compound of claim 4 wherein said radiolabel is selected from tritium, and carbon-14.

6. The compound according to claim 5 wherein said radiolabel is tritium.

7. The compound according to claim 5 wherein said radiolabel is carbon-14.

* * * * *